US012161853B2

(12) United States Patent
Crête et al.

(10) Patent No.: US 12,161,853 B2
(45) Date of Patent: Dec. 10, 2024

(54) IMPLANTABLE MEDICAL DEVICES AND RELATED METHODS THEREOF

(71) Applicant: Puzzle Medical Devices Inc., Montreal (CA)

(72) Inventors: Yves-Antoine Crête, Montreal (CA); François Trudeau, Quebec (CA); Philippe Cormier, Montreal (CA); Maxime Rochon, Québec (CA); Gabriel Georges, Québec (CA); Dany Fillion, Saint-Basile-le-Grand (CA)

(73) Assignee: Puzzle Medical Devices Inc., Montreal (CA)

( * ) Notice: Subject to any disclaimer, the term of this patent is extended or adjusted under 35 U.S.C. 154(b) by 0 days.

(21) Appl. No.: 18/592,095

(22) Filed: Feb. 29, 2024

(65) Prior Publication Data
US 2024/0198078 A1   Jun. 20, 2024

Related U.S. Application Data

(63) Continuation of application No. PCT/CA2023/051450, filed on Oct. 31, 2023.
(Continued)

(51) Int. Cl.
*A61M 60/135* (2021.01)
*A61M 60/13* (2021.01)
(Continued)

(52) U.S. Cl.
CPC .......... *A61M 60/13* (2021.01); *A61M 60/135* (2021.01); *A61M 60/157* (2021.01);
(Continued)

(58) Field of Classification Search
CPC .. A61M 60/13; A61M 60/135; A61M 60/865; A61M 60/8661; A61M 60/88;
(Continued)

(56) References Cited

U.S. PATENT DOCUMENTS

| 4,625,712 A | 12/1986 | Wampler |
| 4,646,719 A | 3/1987 | Neuman et al. |

(Continued)

FOREIGN PATENT DOCUMENTS

| CA | 2701810 A1 | 4/2009 |
| CA | 3014105 A1 | 8/2017 |

(Continued)

OTHER PUBLICATIONS

Extended European Search Report for European Application No. EP21736214.4 dated Jan. 3, 2024, 9 pages.
(Continued)

*Primary Examiner* — Lindsey G Wehrheim

(57) ABSTRACT

An implantable medical device includes a functional unit, an introducer unit for introducing and/or navigating the functional unit in a lumen of body conduit(s) of a subject, and an elongated operable element connectable to a controller for operating the functional unit though the elongated operable element in a lumen of body conduit(s) of the subject. The functional unit, introducer unit, and elongated operable element may be in a slidable relationship for assembling and unassembling the implantable medical device in vivo. The implantable medical device is implantable, explantable, and operable in a lumen of body conduit(s) of a subject according to related methods.

23 Claims, 52 Drawing Sheets

Related U.S. Application Data

(60) Provisional application No. 63/421,366, filed on Nov. 1, 2022.

(51) Int. Cl.
*A61M 60/157* (2021.01)
*A61M 60/861* (2021.01)
*A61M 60/865* (2021.01)
*A61M 60/88* (2021.01)

(52) U.S. Cl.
CPC ........ *A61M 60/861* (2021.01); *A61M 60/865* (2021.01); *A61M 60/88* (2021.01); *A61M 2205/10* (2013.01); *A61M 2210/12* (2013.01)

(58) Field of Classification Search
CPC ............ A61M 60/157; A61M 2205/10; A61M 2210/12
See application file for complete search history.

(56) References Cited

U.S. PATENT DOCUMENTS

| | | | |
|---|---|---|---|
| 4,753,221 A | 6/1988 | Kensey et al. | |
| 4,957,504 A | 9/1990 | Chardack | |
| 4,964,864 A | 10/1990 | Summers et al. | |
| 5,112,349 A | 5/1992 | Summers et al. | |
| 5,749,855 A | 5/1998 | Reitan | |
| 5,888,241 A | 3/1999 | Jarvik | |
| 5,957,672 A | 9/1999 | Aber | |
| 6,015,272 A | 1/2000 | Antaki et al. | |
| 6,050,987 A | 4/2000 | Rosenbaum | |
| 6,176,848 B1 * | 1/2001 | Rau | A61M 60/13 600/16 |
| 6,210,318 B1 | 4/2001 | Lederman | |
| 6,245,007 B1 | 6/2001 | Bedingham et al. | |
| 6,527,800 B1 | 3/2003 | McGuckin, Jr. et al. | |
| 6,669,624 B2 | 12/2003 | Frazier | |
| 6,827,733 B2 | 12/2004 | Boneau | |
| 6,942,611 B2 | 9/2005 | Siess | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,070,555 B2 | 7/2006 | Siess | |
| 7,144,364 B2 | 12/2006 | Barbut et al. | |
| 7,393,181 B2 | 7/2008 | McBride et al. | |
| 7,479,102 B2 | 1/2009 | Jarvik | |
| 7,762,977 B2 | 7/2010 | Porter et al. | |
| 7,841,976 B2 | 11/2010 | McBride et al. | |
| 7,909,862 B2 | 3/2011 | Garrison et al. | |
| 7,914,436 B1 | 3/2011 | Kung | |
| 7,918,880 B2 | 4/2011 | Austin | |
| 7,993,259 B2 | 8/2011 | Kang et al. | |
| 7,998,190 B2 | 8/2011 | Gharib et al. | |
| 7,998,954 B2 | 8/2011 | Otsubo et al. | |
| 8,012,079 B2 | 9/2011 | Delgado, III | |
| 8,075,472 B2 | 12/2011 | Zilbershlag et al. | |
| 8,157,758 B2 | 4/2012 | Pecor et al. | |
| 8,308,798 B2 | 11/2012 | Pintor et al. | |
| 8,333,687 B2 | 12/2012 | Farnan et al. | |
| 8,343,029 B2 | 1/2013 | Farnan et al. | |
| 8,394,010 B2 | 3/2013 | Farnan | |
| 8,439,859 B2 | 5/2013 | Pfeffer et al. | |
| 8,449,443 B2 | 5/2013 | Rodefeld et al. | |
| 8,489,190 B2 | 7/2013 | Pfeffer et al. | |
| 8,579,858 B2 | 11/2013 | Reitan et al. | |
| 8,585,572 B2 | 11/2013 | Mehmanesh | |
| 8,617,239 B2 | 12/2013 | Reitan | |
| 8,690,749 B1 | 4/2014 | Nunez | |
| 8,727,959 B2 | 5/2014 | Reitan et al. | |
| 8,734,331 B2 | 5/2014 | Evans et al. | |
| 8,777,832 B1 | 7/2014 | Wang et al. | |
| 8,784,291 B2 | 7/2014 | Farnan et al. | |
| 8,814,933 B2 | 8/2014 | Siess | |
| 8,821,366 B2 | 9/2014 | Farnan et al. | |
| 9,022,916 B2 | 5/2015 | Farnan et al. | |
| 9,211,367 B2 | 12/2015 | Farnan et al. | |
| 9,216,298 B2 | 12/2015 | Jacobson | |
| 9,217,442 B2 | 12/2015 | Wiessler et al. | |
| 9,314,559 B2 | 4/2016 | Smith et al. | |
| 9,328,741 B2 | 5/2016 | Liebing | |
| 9,339,597 B2 | 5/2016 | Khanal et al. | |
| 9,375,580 B2 | 6/2016 | Bonner et al. | |
| 9,416,791 B2 | 8/2016 | Toellner | |
| 9,421,311 B2 | 8/2016 | Tanner et al. | |
| 9,446,179 B2 | 9/2016 | Keenan et al. | |
| 9,572,915 B2 | 2/2017 | Heuring et al. | |
| 9,616,159 B2 | 4/2017 | Anderson et al. | |
| 9,744,281 B2 | 8/2017 | Siegenthaler | |
| 9,808,633 B2 | 11/2017 | Bonner et al. | |
| 9,861,729 B2 | 1/2018 | Morello et al. | |
| 9,872,947 B2 | 1/2018 | Keenan et al. | |
| 9,878,079 B2 | 1/2018 | Pfeffer et al. | |
| D811,588 S | 2/2018 | Kaiser et al. | |
| 9,889,242 B2 | 2/2018 | Pfeffer et al. | |
| D826,401 S | 8/2018 | Epple | |
| 10,039,873 B2 | 8/2018 | Siegenthaler | |
| 10,137,232 B2 | 11/2018 | Yomtov et al. | |
| 10,143,788 B2 | 12/2018 | Rudser et al. | |
| 10,179,197 B2 | 1/2019 | Kaiser et al. | |
| 10,183,104 B2 | 1/2019 | Anderson et al. | |
| 10,279,094 B2 | 5/2019 | Williams et al. | |
| 10,293,090 B2 | 5/2019 | Bonde et al. | |
| D855,175 S | 7/2019 | Epple | |
| 10,413,648 B2 | 9/2019 | Delgado, III | |
| 10,426,880 B2 | 10/2019 | Kushwaha et al. | |
| 10,443,738 B2 | 10/2019 | Durst et al. | |
| 10,449,276 B2 | 10/2019 | Pfeffer et al. | |
| 10,478,538 B2 | 11/2019 | Scheckel et al. | |
| 10,478,539 B2 | 11/2019 | Pfeffer et al. | |
| 10,500,323 B2 | 12/2019 | Heuring et al. | |
| 10,596,019 B2 | 3/2020 | Melsheimer et al. | |
| 10,722,631 B2 | 7/2020 | Salahieh et al. | |
| 10,799,624 B2 | 10/2020 | Pfeffer et al. | |
| 10,898,626 B2 | 1/2021 | Siegenthaler | |
| 10,980,927 B2 | 4/2021 | Pfeffer et al. | |
| 11,103,690 B2 | 8/2021 | Epple | |
| 11,123,539 B2 | 9/2021 | Pfeffer et al. | |
| 11,129,978 B2 | 9/2021 | Pfeffer et al. | |
| 11,154,704 B2 | 10/2021 | Farnan et al. | |
| 11,167,124 B2 | 11/2021 | Pfeffer et al. | |
| 11,179,557 B2 * | 11/2021 | Georges | A61M 60/13 |
| 11,202,902 B2 | 12/2021 | Najar | |
| 11,235,137 B2 | 2/2022 | Salys | |
| 11,235,138 B2 | 2/2022 | Groß-Hardt et al. | |
| 11,241,569 B2 | 2/2022 | Delgado, III | |
| 11,318,017 B2 | 5/2022 | Besselink | |
| 11,324,940 B2 | 5/2022 | Earles et al. | |
| 11,331,465 B2 | 5/2022 | Epple | |
| 11,351,359 B2 | 6/2022 | Clifton et al. | |
| 11,452,859 B2 | 9/2022 | Earles et al. | |
| 11,471,665 B2 | 10/2022 | Clifton et al. | |
| 11,690,997 B2 | 7/2023 | Georges et al. | |
| 12,053,623 B2 * | 8/2024 | Georges | A61M 60/178 |
| 2005/0220636 A1 | 10/2005 | Henein et al. | |
| 2006/0036127 A1 | 2/2006 | Delgado | |
| 2007/0156006 A1 | 7/2007 | Smith et al. | |
| 2007/0213690 A1 | 9/2007 | Phillips et al. | |
| 2007/0250120 A1 | 10/2007 | Flach et al. | |
| 2008/0004652 A1 | 1/2008 | Abboud et al. | |
| 2008/0132748 A1 | 6/2008 | Shifflette | |
| 2008/0154328 A1 | 6/2008 | Thompson et al. | |
| 2009/0112312 A1 | 4/2009 | LaRose et al. | |
| 2009/0247945 A1 | 10/2009 | Levit et al. | |
| 2010/0249489 A1 | 9/2010 | Jarvik | |
| 2010/0268017 A1 | 10/2010 | Siess | |
| 2011/0004046 A1 | 1/2011 | Campbell et al. | |
| 2011/0106120 A1 | 5/2011 | Haselby et al. | |
| 2012/0041255 A1 | 2/2012 | Delgado, III | |
| 2012/0046515 A1 * | 2/2012 | Woo | A61M 60/216 600/16 |
| 2012/0053670 A1 | 3/2012 | Purdy | |
| 2012/0101455 A1 | 4/2012 | Liebing | |
| 2012/0172654 A1 | 7/2012 | Bates | |

(56) References Cited

U.S. PATENT DOCUMENTS

| | | |
|---|---|---|
| 2012/0172655 A1 | 7/2012 | Campbell et al. |
| 2012/0178985 A1 | 7/2012 | Walters et al. |
| 2012/0178986 A1 | 7/2012 | Campbell et al. |
| 2012/0203328 A1 | 8/2012 | Yribarren |
| 2012/0226309 A1 | 9/2012 | Jönsson |
| 2012/0253387 A1 | 10/2012 | Teichman et al. |
| 2012/0310036 A1 | 12/2012 | Peters et al. |
| 2013/0138205 A1 | 5/2013 | Kushwaha et al. |
| 2013/0204362 A1 | 8/2013 | Toellner et al. |
| 2013/0253344 A1 | 9/2013 | Griswold et al. |
| 2013/0253347 A1 | 9/2013 | Griswold et al. |
| 2014/0031607 A1 | 1/2014 | Zilbershlag et al. |
| 2014/0066979 A1 | 3/2014 | Jonsson |
| 2014/0275726 A1 | 9/2014 | Zeng |
| 2015/0250935 A1 | 9/2015 | Anderson et al. |
| 2015/0306291 A1 | 10/2015 | Bonde et al. |
| 2016/0022890 A1 | 1/2016 | Schwammenthal et al. |
| 2016/0089482 A1 | 3/2016 | Siegenthaler |
| 2016/0206798 A1 | 7/2016 | Williams et al. |
| 2016/0256620 A1 | 9/2016 | Scheckel et al. |
| 2016/0279310 A1 | 9/2016 | Scheckel et al. |
| 2017/0087288 A1 | 3/2017 | Gross-Hardt et al. |
| 2017/0119945 A1 | 5/2017 | Neumann |
| 2017/0173242 A1 | 6/2017 | Anderson et al. |
| 2017/0274128 A1 | 9/2017 | Tamburino et al. |
| 2017/0340789 A1 | 11/2017 | Bonde et al. |
| 2017/0340877 A1 | 11/2017 | Ollivier |
| 2018/0110909 A1 | 4/2018 | LaRose et al. |
| 2018/0193543 A1 | 7/2018 | Sun |
| 2018/0214141 A1 | 8/2018 | Mendez |
| 2018/0243551 A1 | 8/2018 | Nagaoka et al. |
| 2018/0250457 A1 | 9/2018 | Morello et al. |
| 2019/0046703 A1 | 2/2019 | Shambaugh et al. |
| 2019/0126014 A1 | 5/2019 | Kapur et al. |
| 2019/0358382 A1 | 11/2019 | Delgado, III |
| 2020/0023109 A1 | 1/2020 | Epple |
| 2020/0023158 A1 | 1/2020 | Epple |
| 2020/0054806 A1 | 2/2020 | Sun |
| 2020/0261633 A1 | 8/2020 | Spanier et al. |
| 2020/0316277 A1 | 10/2020 | Delgado, III |
| 2020/0330665 A1 | 10/2020 | Josephy et al. |
| 2020/0405926 A1 | 12/2020 | Alexander et al. |
| 2021/0008261 A1* | 1/2021 | Calomeni ........... A61M 60/174 |
| 2021/0008263 A1 | 1/2021 | Leonhardt |
| 2021/0077687 A1 | 3/2021 | Leonhardt |
| 2021/0106808 A1 | 4/2021 | Siegenthaler |
| 2021/0260360 A1 | 8/2021 | Georges et al. |
| 2022/0080183 A1 | 3/2022 | Earles et al. |
| 2022/0080184 A1 | 3/2022 | Clifton et al. |
| 2022/0134082 A1 | 5/2022 | Pfeffer et al. |
| 2022/0226634 A1 | 7/2022 | Groß-Hardt et al. |
| 2022/0257920 A1 | 8/2022 | Earles et al. |
| 2022/0296852 A1* | 9/2022 | Georges .................... A61F 2/90 |
| 2022/0296880 A1 | 9/2022 | Clifton et al. |
| 2022/0323744 A1 | 10/2022 | Georges et al. |
| 2022/0331576 A1 | 10/2022 | Leonhardt |
| 2023/0056440 A1* | 2/2023 | Georges ............... A61M 60/216 |
| 2023/0137466 A1* | 5/2023 | Georges ................ A61M 60/31 600/18 |
| 2023/0293880 A1* | 9/2023 | Georges .............. A61M 60/135 600/16 |
| 2024/0090882 A1* | 3/2024 | Georges .................... A61F 2/07 |

FOREIGN PATENT DOCUMENTS

| | | |
|---|---|---|
| CA | 3054771 A1 | 9/2018 |
| CN | 106456857 B | 11/2018 |
| CN | 112870547 A | 6/2021 |
| CN | 110049792 B | 1/2022 |
| DE | 19613565 C1 | 7/1997 |
| DE | 102004054714 A1 | 5/2006 |
| EP | 2860849 A1 | 4/2015 |
| EP | 3456367 A1 | 3/2019 |
| EP | 3539584 A1 | 9/2019 |
| EP | 2745805 B2 | 5/2022 |
| WO | WO-0227225 A1 | 4/2002 |
| WO | WO-2008017289 A2 | 2/2008 |
| WO | WO-2008027366 A2 | 3/2008 |
| WO | WO-2012094641 A2 | 7/2012 |
| WO | WO-2013062859 A1 | 5/2013 |
| WO | WO-2014070472 A1 | 5/2014 |
| WO | WO-2015109028 A1 | 7/2015 |
| WO | WO-2015148821 A1 | 10/2015 |
| WO | WO-2015177793 A2 | 11/2015 |
| WO | WO-2016185473 A1 | 11/2016 |
| WO | WO-2017185082 A1 | 10/2017 |
| WO | WO-2017217946 A1 | 12/2017 |
| WO | WO-2018096531 A1 | 5/2018 |
| WO | WO-2018129177 A1 | 7/2018 |
| WO | WO-2018158635 A1 | 9/2018 |
| WO | WO-2018226991 A1 | 12/2018 |
| WO | WO-2019083989 A1 | 5/2019 |
| WO | WO-2019094963 A1 | 5/2019 |
| WO | WO-2019152875 A1 | 8/2019 |
| WO | WO-2019183247 A1 | 9/2019 |
| WO | WO-2019191851 A1 | 10/2019 |
| WO | WO-2020036886 A1 | 2/2020 |
| WO | WO-2020198765 A2 | 10/2020 |
| WO | WO-2021062565 A2 | 4/2021 |
| WO | WO-2021062566 A1 | 4/2021 |
| WO | WO-2021117021 A1 | 6/2021 |
| WO | WO-2021138673 A1 | 7/2021 |
| WO | WO-2021234638 A1 | 11/2021 |
| WO | WO-2022094690 A1 | 5/2022 |
| WO | WO-2022096941 A1 | 5/2022 |
| WO | WO-2023178431 A1 | 9/2023 |
| WO | WO-2024092349 A1 | 5/2024 |

OTHER PUBLICATIONS

Extended European Search Report for European Application No. EP23166411.1 dated Oct. 6, 2023, 10 pages.

International Preliminary Report on Patentability issued in PCT/CA2019/050421, dated Oct. 6, 2020, 9 pages.

International Preliminary Report on Patentability issued in PCT/CA2020/051673, dated Apr. 5, 2022, 7 pages.

International Preliminary Report on Patentability issued in PCT/CA2020/051677, dated Apr. 5, 2022, 7 pages.

International Preliminary Report on Patentability issued in PCT/ZA2020/050022, dated Sep. 28, 2021, 5 pages.

International Search Report and Written Opinion for International Application No. PCT/CA2023/050378 dated Jun. 9, 2023, 8 pages.

International Search Report and Written Opinion for International Application No. PCT/CA2023/051450 dated Jan. 16, 2024, 9 pages.

International Search Report and Written Opinion for PCT/ZA2020/050022, dated Sep. 24, 2020, 6 pages.

International Search Report and Written Opinion issued in PCT/CA2019/050421 dated Jul. 8, 2019, 12 pages.

International Search Report and Written Opinion issued in PCT/CA2020/051673 dated Mar. 26, 2021, 12 pages.

International Search Report and Written Opinion issued in PCT/CA2020/051677, dated Mar. 15, 2021, 11 pages.

International Search Report and Written Opinion issued in PCT/CA2021/050469 dated Jul. 28, 2021, 10 pages.

International Search Report and Written Opinion issued in PCT/IB2020/061913 dated Mar. 19, 2021, 11 pages.

International Search Report and Written Opinion issued in PCT/IB2021/052925 dated Jul. 28, 2021, 14 pages.

International Search Report and Written Opinion issued in PCT/IB2021/054395 dated Aug. 12, 2021, 9 pages.

International Search Report and Written Opinion issued in PCT/US2021/012083 dated Mar. 31, 2021, 7 pages.

Lo Coco, V. et al. "Right ventricular failure after left ventricular assistance device implantation: a review of the literature," J. Thorac. Dis., Feb. 2021, 13(2):1256-1269.

Non-Final Office Action for U.S. Appl. No. 17/316,090 dated Jan. 31, 2024, 15 pages.

Notice of Allowance for U.S. Appl. No. 17/752,378 dated Feb. 16, 2023, 12 pages.

(56) References Cited

OTHER PUBLICATIONS

Notice of Allowance issued in U.S. Appl. No. 17/047,598 dated May 3, 2021, 7 pages.
Office Action for Japanese Application No. JP20210560164 mailed Feb. 27, 2024, 9 pages.
Rhee and Blackshear, "Left Ventricular Assist Using a Jet Pump," ASAIO Trans., Jul.-Sep. 1990, 36(3):M515-M518.
Rogers, T. et al. NIH, National Heart, Lung, and Blood Institute "First in Man Testing of a Dedicated Closure Device for Transcaval Access for Transcatheter Aortic Valve Replacement," NCT03432494, Publication Date Unknown, 16 pages.
Supplemental International Search Report issued in PCT/ZA2020/050022, dated Jul. 13, 2021, 8 pages.
Office Action for Canadian Patent Application No. CA3164739 dated Mar. 4, 2024, 5 pages.
International Preliminary Report on Patentability issued in PCT/US2021/012083, dated Jul. 14, 2022, 7 pages.
Search Report for Japanese Application No. JP2021-560164 dated Feb. 21, 2024, 40 pages with English Translation.
Notice of Allowance for U.S. Appl. No. 17/316,090 dated Mar. 25, 2024, 9 pages.
Office Action for Canadian Patent Application No. CA3135041 dated Mar. 8, 2024, 8 pages.

* cited by examiner

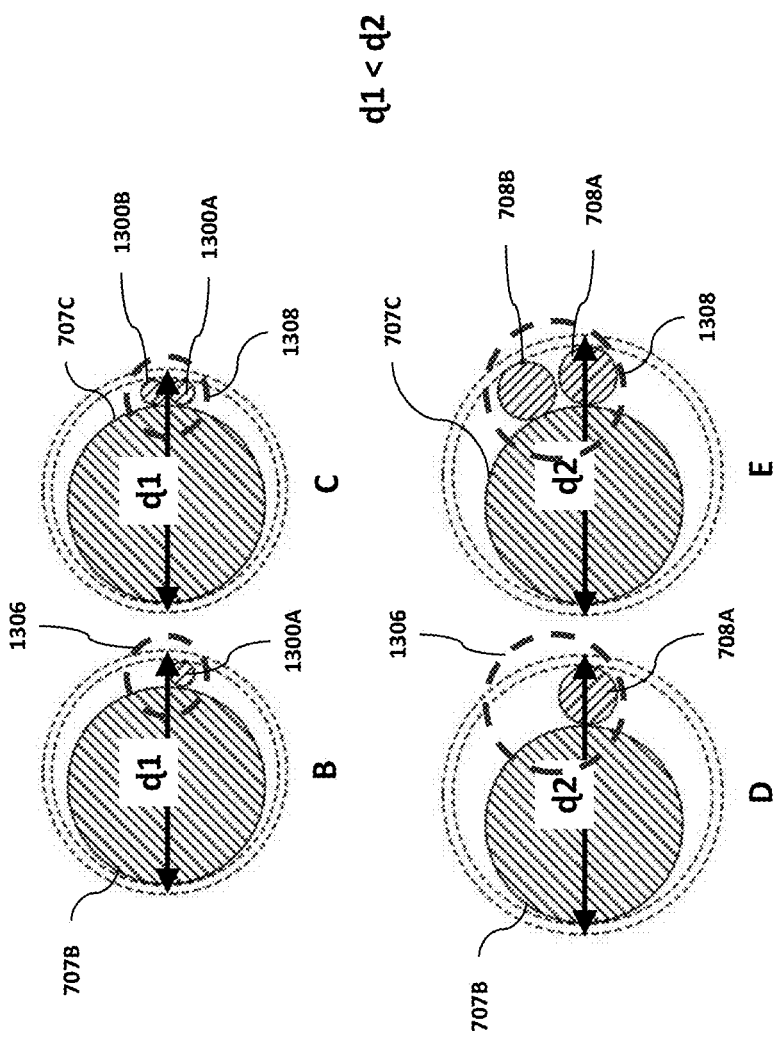
FIG. 14B-E

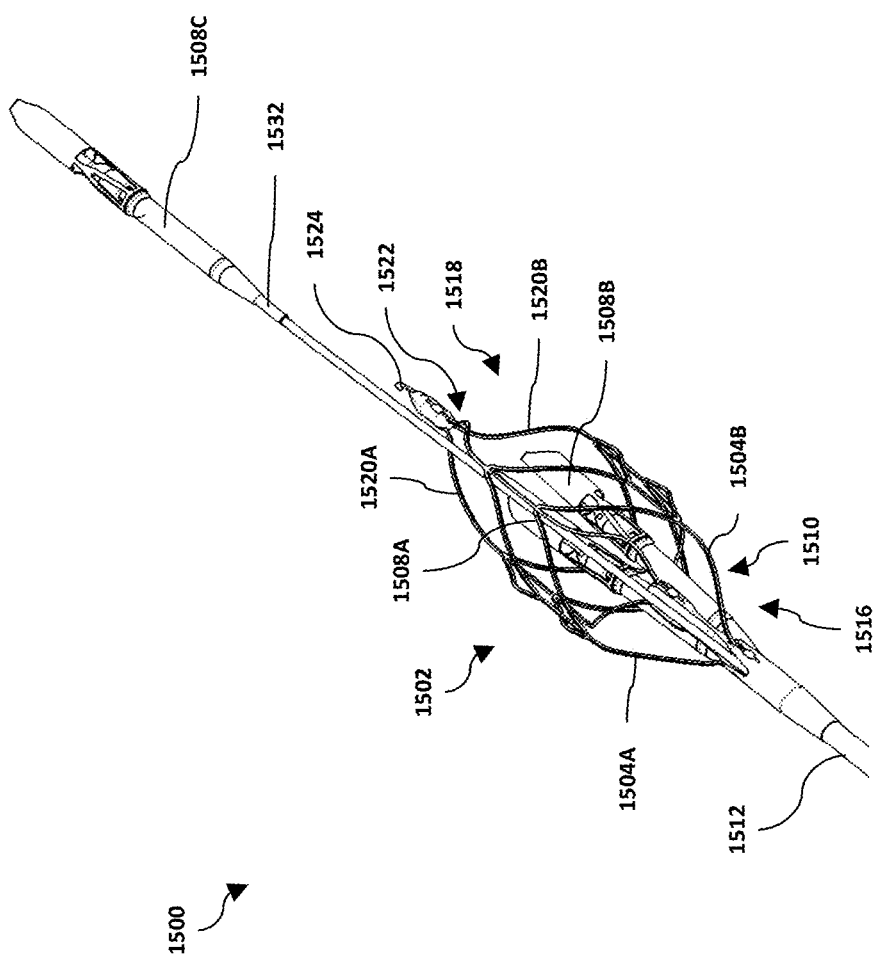

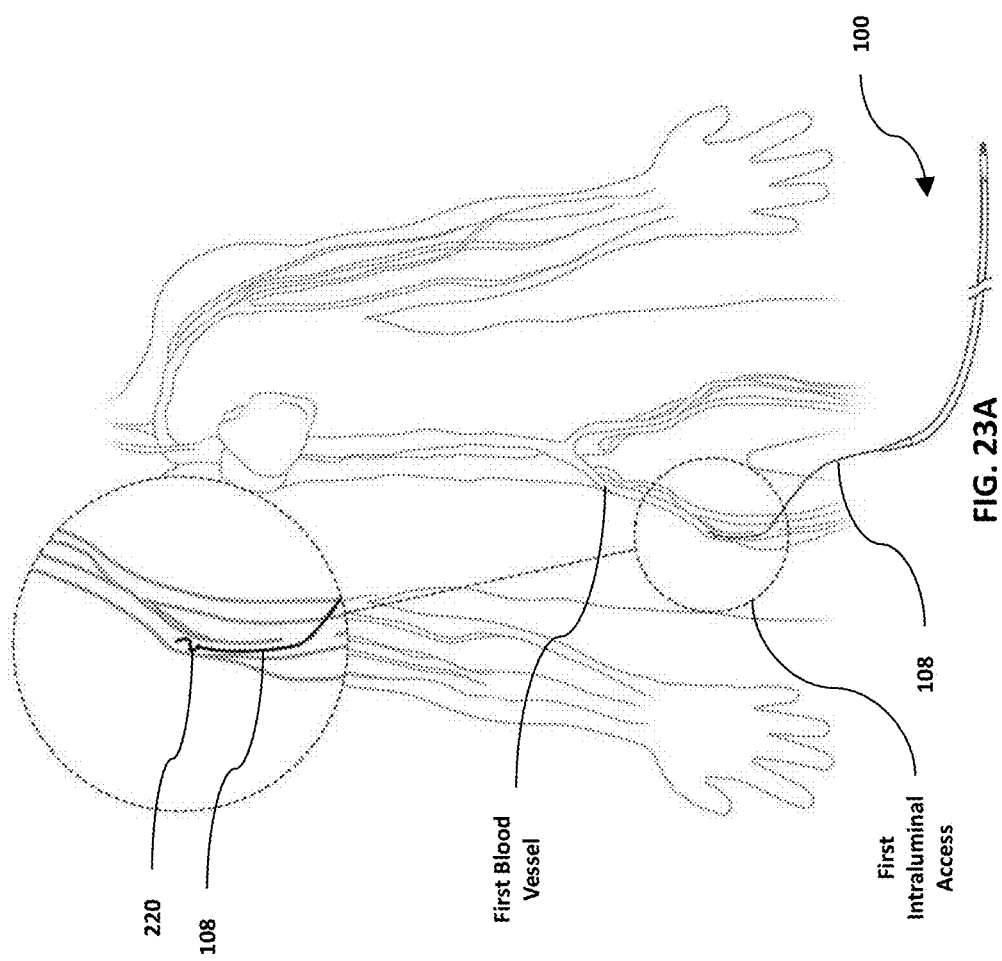

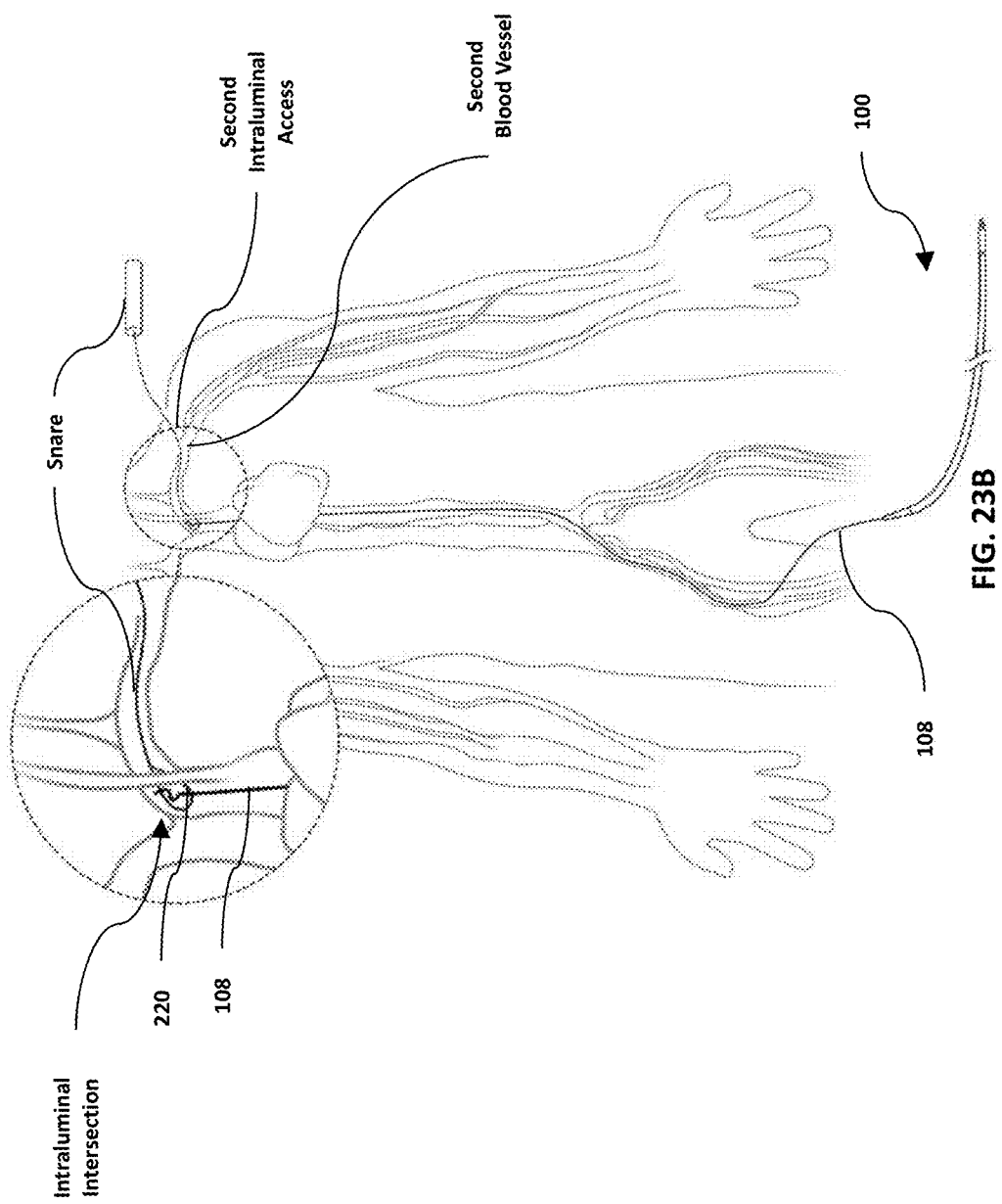

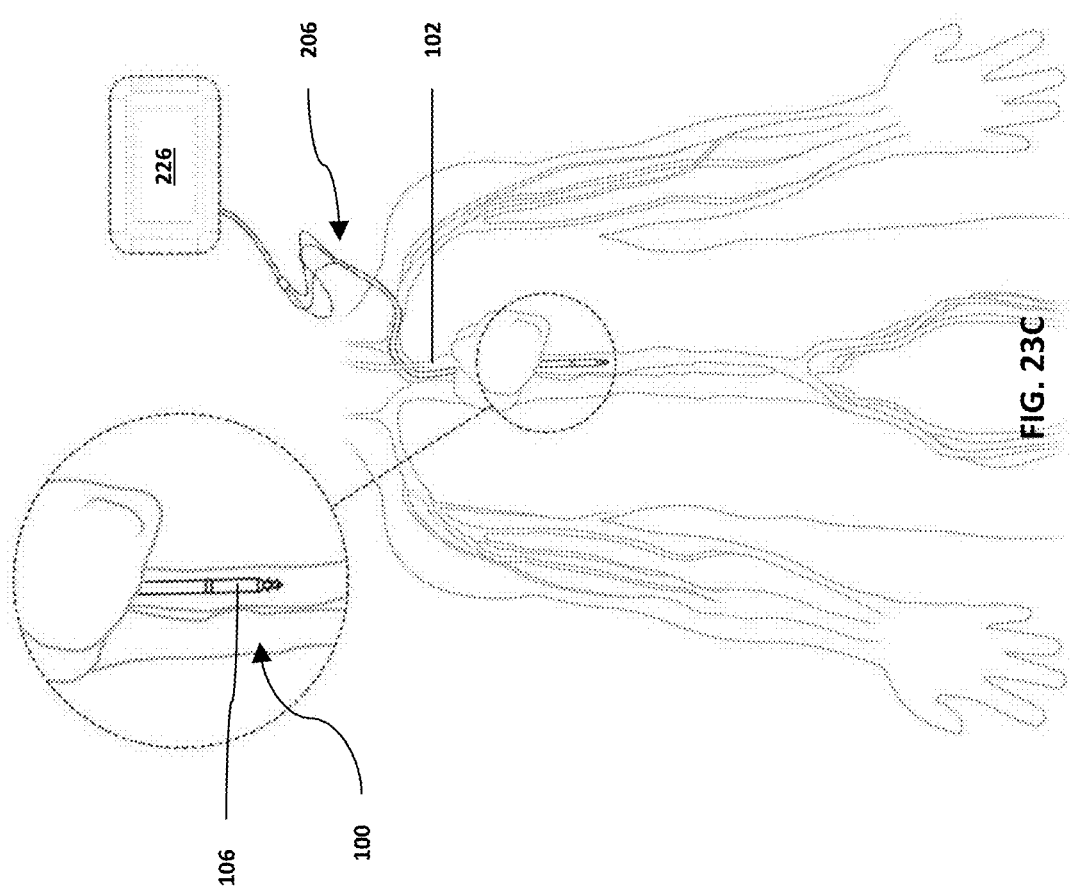

IMPLANTABLE MEDICAL DEVICES AND RELATED METHODS THEREOF

CROSS-REFERENCE(S) TO OTHER RELATED PATENT APPLICATION

The present patent application is a continuation of International Application No. PCT/CA2023/051450, filed Oct. 31, 2023, which claims the benefit of and priority to U.S. Provisional Patent Application No. 63/421,366, filed Nov. 1, 2022, the entire content of which, including all references incorporated by reference therein, if any, is incorporated herein by reference for all purpose as if fully set forth herein, except for any definition(s), subject matter disclaimer(s) or disavowal(s), and except to the extent that the incorporated material is inconsistent with the express disclosure herein, in which case the language in the present disclosure controls.

FIELD

The present disclosure generally relates to medical devices that are implantable in vivo by related methods.

BACKGROUND

Minimally invasive surgeries, such as transcatheter aortic valve replacement (TAVR) and transcatheter pacemaker implantation to name a few in the cardiovascular field, are attractive as they are less traumatizing for the subject's body than more invasive open surgeries.

Particularly, implantations of medical devices by minimally invasive surgeries require at least one relatively small body incision through which one or more medical devices are routed, notably by transcatheter procedure(s), to be implanted at one or more corresponding implantation sites in a subject's body. This body incision(s) is generally smaller in size as compared to the incision(s) performed during more invasive open surgeries where direct access to the implantation site(s) is usually required for implanting the medical device(s). As a consequence, the subject's recovery and hospitalization times, pain, and/or risk of infection are typically drastically reduced when medical devices are implanted by minimally invasive surgeries, as opposed to open surgeries. Not only implantation of medical devices by minimally invasive surgeries may improve overall patient outcomes, but may also reduce the economic burden normally associated with implantation of medical devices by open surgeries.

However, minimally invasive surgical implantations of medical devices depend for the most part on the implantation route(s) in the subject's body. In the context of minimally invasive surgical implantations in a subject's cardiovascular system, for example, one or more blood vessels may be so small in diameter that the implantable medical devices may be prevented from being appropriately introduced and appropriately routed in the lumen thereof up to an intraluminal implantation site. Additionally or alternatively, one or more blood vessels may be so tortuous in shape that the implantable medical devices may be prevented from being routed in the lumen thereof up to an intraluminal implantation site without traumatizing and/or damaging the blood vessel intima.

For minimally invasive surgical implantations of medical devices requiring a percutaneous transluminal access for a relatively long period of time, as the case may be for some cardiovascular implantations of medical devices, achieving an appropriate hemostasis at the site of the percutaneous transluminal access while ideally having a minimal impact on subject's mobility may be desirable.

There is therefore an on-going need for improvement in the field of medical devices that are implantable by minimally invasive surgeries.

SUMMARY

A first aspect of the present disclosure is directed to an implantable medical, including: a functional unit; and an introducer unit operatively connected to the functional unit for operating the functional unit, the introducer unit being configured for introducing the functional unit in the lumen of the body conduit and for implanting the implantable medical device partially inside the body conduit and partially outside the body conduit.

A second aspect of the present disclosure is directed to an implantable medical, including: a functional unit having an elongated operable element connected thereto and extending therefrom; and an introducer unit having a body defining a longitudinal guide hole that extends at least partially therealong for slidably receiving the elongated operable element therein, the introducer unit being configured for slidably assembling with the functional unit in the lumen of the body conduit for implanting the implantable medical device partially inside the body conduit and partially outside the body conduit.

A third aspect of the present disclosure is directed to a method of implanting an implantable medical device, the method including: introducing the implantable medical device in a lumen of a body conduit through a first intraluminal access; advancing the implantable medical device in the lumen of the body conduit to a second intraluminal access; exiting an end portion of the implantable medical device through the second intraluminal access; and operating the implantable medical device via the end portion.

A fourth aspect of the present disclosure is directed to a method of explanting an implantable medical device, the method including: obtaining a first body conduit intraluminal access on a side of the implantable medical device intraluminally implanted in a body conduit and having an end portion thereof partially positioned through a second body conduit intraluminal access located on an opposite side of the implantable medical device; and retrieving the implantable medical device from the body conduit through the first body conduit intraluminal access.

An aspect of the present disclosure is directed to an implantable medical device, including: a functional unit having an elongated operable element connected thereto and extending therefrom; and an introducer unit slidably receiving the elongated operable element therethrough such that an intermediate portion of the elongated operable element is disposed between the functional unit and the introducer unit, the introducer unit being configured to introduce and/or navigate the functional unit intraluminally, the intermediate portion being configured to hinge so that the functional unit and the introducer unit may hinge relative to each other intraluminally.

An aspect of the present disclosure is directed to a medical device assembly, including: a sheath configured to be introduced in an intraluminal access of a subject's body; and an implantable medical device including a taper shape for dilating an intraluminal access when introduced therethrough, the implantable medical device being releasably engageable to the sheath so as to be intraluminally deliverable while the sheath is introduced in the intraluminal access of a subject's body for implanting the implantable medical device without leaving the sheath afterward.

DEFINITIONS

As intended herein, the expression "body conduit" refers to any physiological structure of a subject's body that defines an inner space, such as blood vessels, lymphatic vessels, hollow organ, and the like.

The terms "operation", "operated", "operating", and the like encompass operating, controlling, powering, and corresponding actions when used in the context of using a medical device.

The terms "elongated operable element" and corresponding structures encompass any elongated structure capable of slidably moving a functional unit or a functional element of an implantable medical device and/or capable of transferring power to a functional unit or a functional element of an implantable medical device.

BRIEF DESCRIPTION OF THE DRAWINGS

In order that the present disclosure be readily understood, at least some selected embodiments thereof are illustrated by way of example(s) in the accompanying drawings. Accordingly, the accompanying drawings are illustrative in nature only and are not intended to be construed and interpreted as limiting the extent of the subject matter protected by the claims.

It is noted that like reference numerals identify similar or equivalent elements and/or features throughout the drawings. If present in the claims, reference numerals are provided only to make claims easier to comprehend and are not intended to be construed and interpreted as limiting the extent of the subject matter protected by the claims. The elements and/or features illustrated throughout the drawings are not necessarily drawn to scale.

FIG. 14B is a transversal cross-section view taken along the plane XIV-B of FIG. 14A, FIG. 14C is a transversal cross-section view taken along the plane XIV-C of FIG. 14A, FIGS. 14D-E is for comparison purposes.

FIGS. 15-19 are a perspective views of the implantable medical device of FIG. 7 provided with another anchor, in accordance with an embodiment.

FIGS. 23A-C are schematic representations of the implantable medical of FIG. 7 being navigated in a lumen of a body conduit of a subject's body, in accordance with an embodiment.

DETAILED DESCRIPTION

Figure 1:
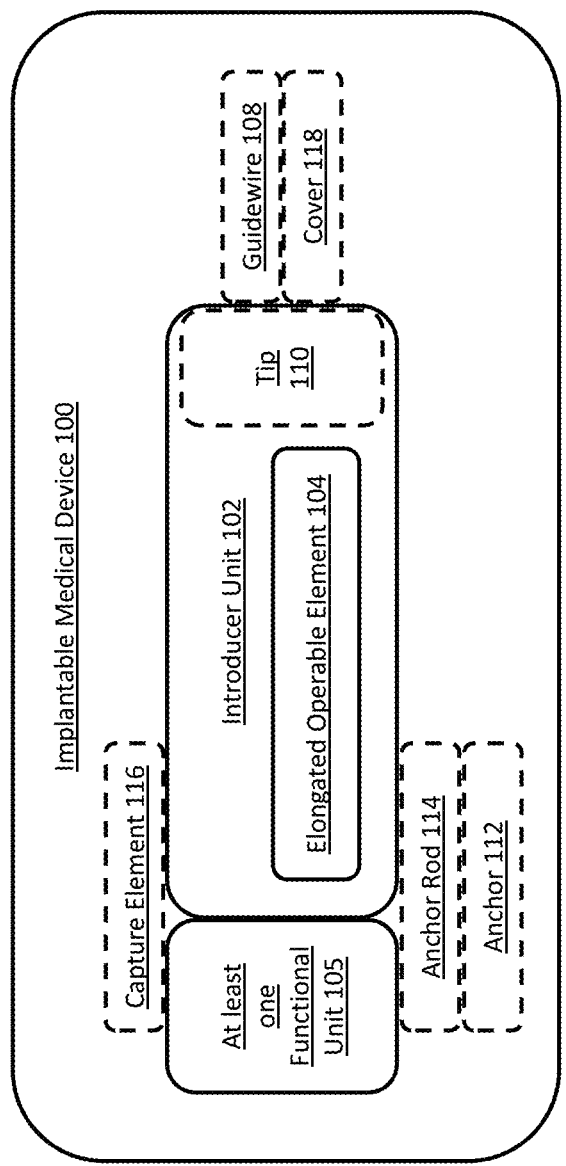
FIG. 1 is a schematic representation of an implantable medical device provided with an introducer unit having an elongated operable element and a functional unit in a non-slidable relationship with the introducer unit, in accordance with a first aspect of the present technology.

The subject matter of the present disclosure, along with any advantage thereof, is described and explained in the following detailed description with reference to the non-limiting aspect(s), embodiment(s), example(s), feature(s), element(s), and/or step(s) presented hereinafter and illustrated in the accompanying non-limiting drawings. Recognizing that these non-limiting aspect(s), embodiment(s), example(s), feature(s), element(s), and step(s) may vary, the skilled addressee shall readily recognize that any other variants thereof and any combination of these other variants, as the case may be, are contemplated without departing from the scope of the present disclosure, even if they are all not explicitly presented and stated herein.

Therefore, these non-limiting aspect(s), embodiment(s), example(s), feature(s), and/or element(s) is/are intended merely to facilitate an understanding of ways in which the claimed subject matter may be reduced to practice by the skilled addressee. Accordingly, these non-limiting aspect(s), embodiment(s), example(s), feature(s), and/or element(s) shall not to be construed as limiting the scope of the claimed subject matter, which is defined solely by the accompanying claims and applicable law.

The terminology used herein is only for the purpose of describing and explaining the claimed subject matter and is not intended to limit the scope thereof. Unless defined otherwise, all technical, engineering, scientific, and other relevant terminology used herein have the same meanings as commonly understood by the skilled addressee.

With the foregoing in mind, the present disclosure relates to medical devices that are implantable in and explantable from a lumen of a subject's body by minimally invasive surgeries. For example, the medical device disclosed herein may be implanted in and/or explanted from the lumen of blood vessels, lymphatic vessels, and hollow organs. As it will be appreciated hereinafter, the medical devices disclosed herein, along with their implantation and explanation modalities, are suited for introduction, navigation, and implantation in as well as explanation from lumen(s) of a subject's body that may typically be refractory due to size limitation or size incompatibility to the use of medical devices known in the art.

At a high level, the implantable medical devices disclosed herein include an introducer unit and a functional unit. The introducer unit and the functional unit may or may not be in a slidable relationship for assembling the introducer unit and the functional unit together and/or for unassembling the introducer unit and the functional unit from each other. The introducer unit is configured to introduce and/or navigate the functional unit in a lumen of one or more body conduits, such as blood vessels, for implanting the functional unit intraluminally inside the lumen of one or more body conduits. So implanted, the introducer unit is at least partially externalized from the body conduit for intraluminally operating the functional unit therethrough.

With reference to FIGS. 1-6, an implantable medical device 100 will be described, in accordance with a first aspect of the present disclosure.

FIG. 1 schematizes the implantable medical device 100, according to embodiments. The implantable medical device 100 includes an introducer unit 102 having an elongated operable element 104 integrated thereto and at least one functional unit 105 operatively connected to the elongated operable element 104 for operation. In the first aspect of the present disclosure, the introducer unit 102 and the functional unit 105 are physically coupled together in a non-slidable relationship and thus form an integral, one-piece device. The implantable medical device 100 may be deliverable in, implantable in, and retrievable from a lumen of body conduit(s). The introducer unit 102 may serve as a percutaneous dilator provided with the elongated operable element 104 integrated thereto, such that the functional unit 105 is implanted in vivo with the assistance of introducer unit 102 and is operated through the introducer unit 102 from outside a subject's body. The functional unit 105 is operable via the elongated operable element 104, such as by being electrically or mechanically operated, when the elongated operable element 104 is operatively connected to a controller (not shown). Such operation may produce a hemodynamic effect in a subject's body.

The introducer unit 102 is not only configured to introduce, guide, and navigate the functional unit 105 in a lumen of body conduit(s) for implanting the functional unit 105 to an intraluminal implantation site thereof, but also to operate the functional unit 105 intraluminally in the lumen through it by operative connection to a controller, which connection takes place extraluminally outside the lumen.

When the implantable medical device 100 is implanted in a lumen of body conduit(s), the introducer unit 102 is positioned partially extraluminally outside a lumen of body conduit(s) through an intraluminal access, while the functional unit 105 is positioned intraluminally in a lumen of the body conduit(s).

As schematically illustrated in FIG. 1, the implantable medical device 100 may further include, for example, a guidewire 108, a tip 110, an anchor 112, an anchor rod 114, a capture element 116, and a cover 118 (optional items are represented by dash lines in FIG. 1), as it will be described hereinafter. The implantable medical device 100 may also optionally include more than one functional unit 105.

Figure 2A:
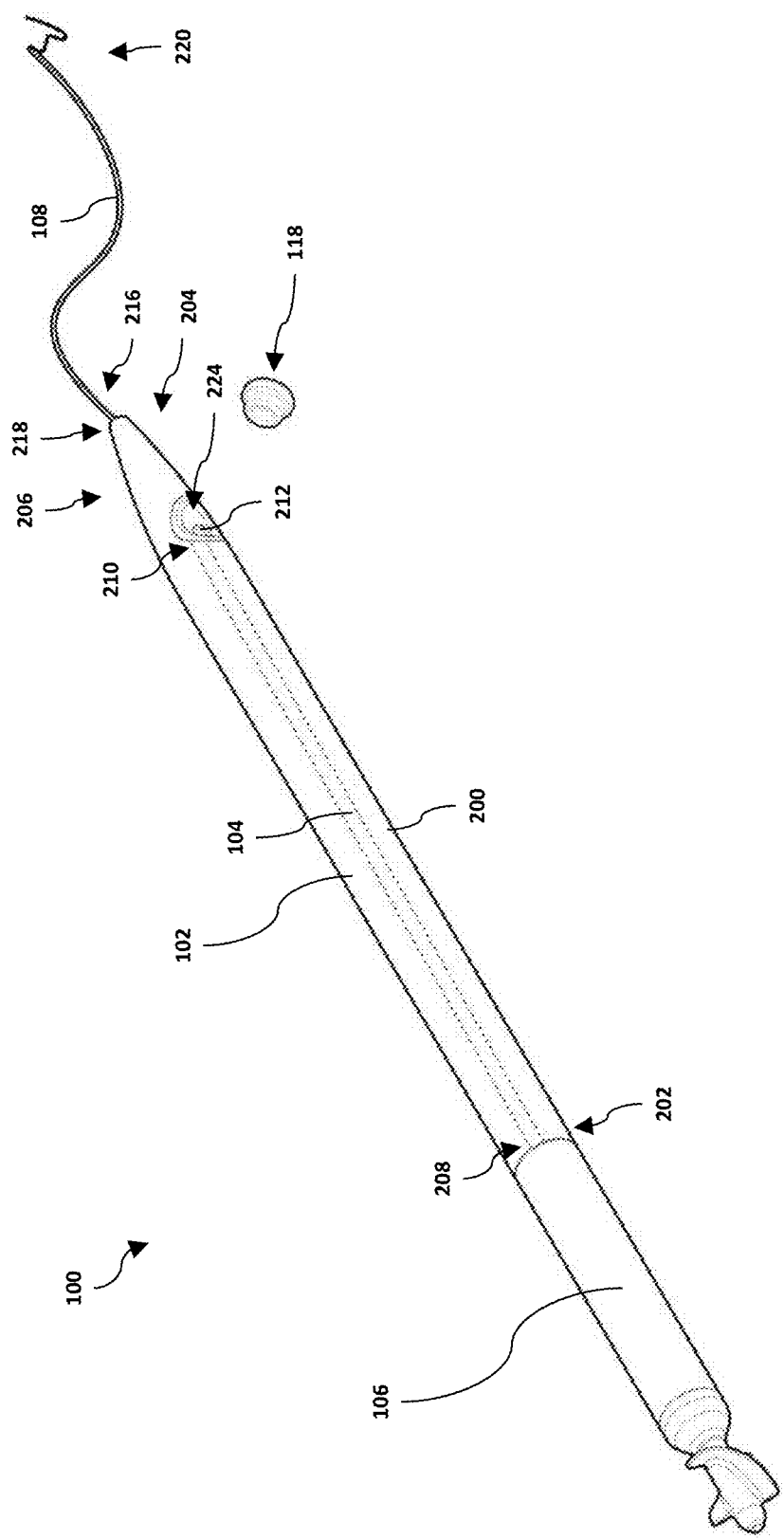
FIGS. 2A-B are perspective views of an implantable medical device that is non slidable, such as one of FIG. 1, in accordance with an embodiment.
Figure 2B:
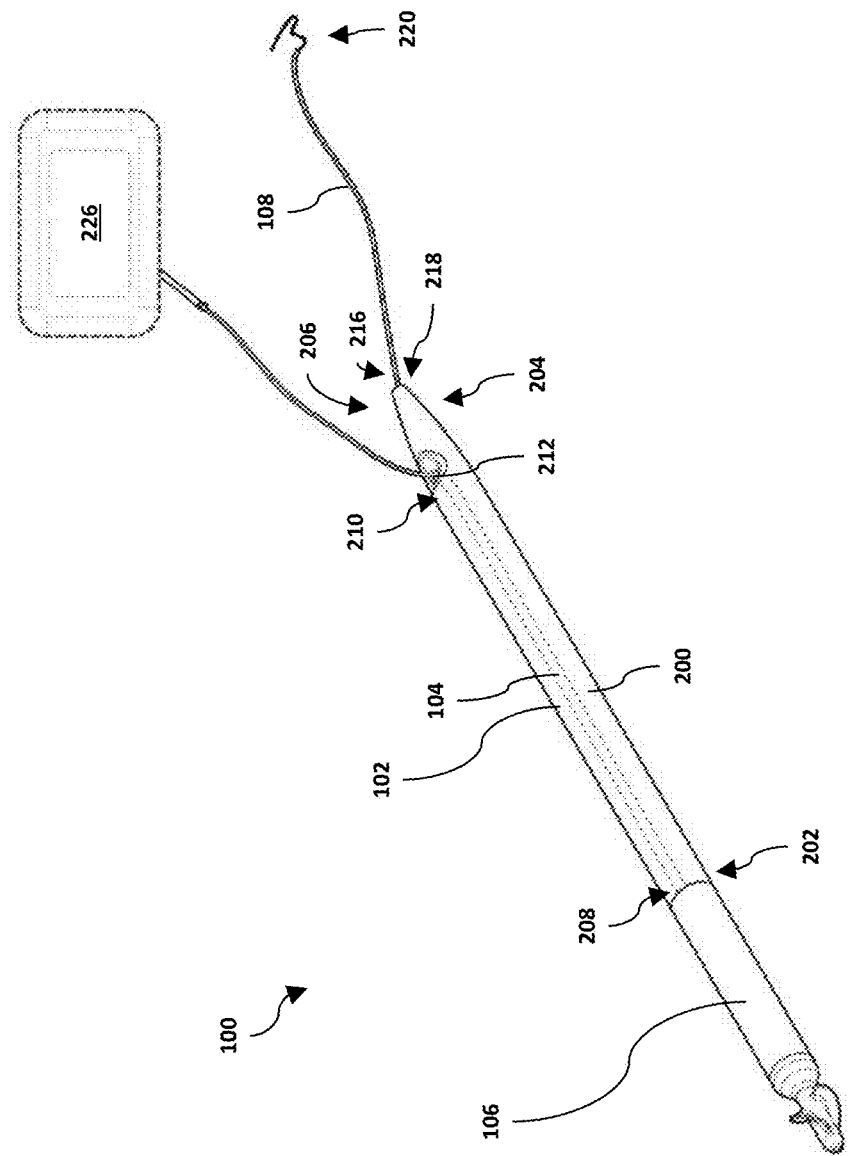

FIGS. 2A-B illustrate the implantable medical device 100 that includes the introducer unit 102 and a pump element 106 provided as the functional unit 105, according to embodiments. The introducer unit 102 has a body 200 extending between a proximal end portion 202, where the pump element 106 is physically coupled thereto, and a distal end portion 204, which corresponds to the distal end portion 206 of the implantable medical device 100. The pump element 106 may be physically coupled to the introducer unit 102 by being glued, fused, welded, and the like.

Although the proximal end portion 202 and the distal end portion 204 of the introducer unit 102 may be of any shape, the distal end portion 204 may be more specifically shaped to facilitate the introduction of the implantable medical device 100 through an intraluminal access of a body conduit. The distal end portion 204 may also be shaped to mitigate or prevent damage or injury to lumen walls, such as the intima in the case of a blood vessel, that may be caused by the introduction and navigation of the implantable medical device 100 in a lumen. Hence, the distal end portion 204 of the introducer unit 102 may be so shaped that its transverse cross-sectional size and/or shape progressively increases running from the distal end portion 204 towards the proximal end portion 206 of the introducer unit 102.

As illustrated in FIGS. 2A-B, for example, the distal end portion 204 of the introducer unit 102 is tapered and/or profiled in shape (referred herein to as "tapered"). However, the distal end portion 204 of the introducer unit 102 may have any other suitable shape, such as a rounded or convex shape, an ovaloid shape, a pyramid shape, a blunt shape with rounded edge(s), or any other shapes that is atraumatic for the lumen wall. In all cases, the distal end portion 204 of the introducer unit 102 may be void of sharp edge(s) and corresponding structure that could damage or injury, such as by unwanted abrasion, scratching, cutting, puncturing, rupture and/or dissection of, the lumen wall while the implantable medical device 100 is introduced and/or navigated therethrough. Regardless of its shape, the distal end portion 204 of the introducer unit 102 may be attachable to a wireline or other corresponding structure that may be pulled for introducing and/or navigating the implantable medical device 100 inside a lumen of body conduit(s). In this case, such an attachment is strong enough to sustain an appropriate pulling force without breaking in the context of a medical procedures.

When the implantable medical device 100 is used appropriately, the tapered shape of the distal end portion 204 may assist and/or facilitate the introduction of the introducer unit 102 through a lumen of body conduit(s) by gradually dilating the intraluminal access thereof, which may be a percutaneous intraluminal access, as the introducer unit 102 is being introduced therethrough. As a result, the intraluminal access becomes so sized and/or shaped to accept the passage of the pump element 106 therethrough.

Still referring to FIGS. 2A-B, the introducer unit 102 is provided with the elongated operable element 104 (shown in dash lines as a way to see through the introducer unit 102) operatively connected, at a proximal end portion 208 thereof, to the pump element 106 and removably operatively connectable, at a distal end portion 210 thereof, by a connector 212 to an optional controller 226 (illustrated in FIG. 2B), according to embodiments. The elongated operable element 104 extends at least partially along the introducer unit 102 and may be located anywhere, such as within the body 200 (as illustrated in FIGS. 2A-B) or at the surface of the body 200 of the introducer unit 102. The connector 212 is integrated to the distal end portion 204 of the introducer unit 102 and may be located on the periphery thereof, as illustrated in FIGS. 2A-B, or at the extremity thereof.

As illustrated, the elongated operable element 104 is an electrical conductor configured to transmit electricity from a controller, when connected thereto, to the pump element 106. Particularly, the electrical conductor operatively interconnects the pump element 106 to the controller 226 by a removable electric connection provided by the connector 212 such that the pump element 106 may be electrically operated by the controller from the distal end portion 206 of the implantable medical device 100.

Alternatively, the elongated operable element 104 may be a driving shaft configured to transmit torque from a controller, such as an actuator or a motor, to the pump element 106. In this case, the driving shaft may operate the pump element 106 or any other functional unit 105 in various ways, including by a rotary movement and/or a reciprocating movement.

Still alternatively, the implantable medical device 100 may be provided with a wireless module integrated to the introducer unit 102. The wireless module is operatively connected to the elongated operable element 104, which in this case may include electrical conductors, and is configured to wirelessly connect to a controller for operating the pump element 106.

To enable or facilitate intraluminal navigation, the introducer unit 102 and the elongated operable element 104 may be made of a bendable, flexible, and/or resilient material so as to accommodate or conform with various body conduit morphologies, but may still be rigid enough to be pushed through an intraluminal access. For example, the introducer unit 102 may be made of polymer, such as thermoplastic polyurethane, while the elongated operable element 104 may include electrical conductors or be a driveshaft made of suitable bendable, flexible, and/or resilient material.

As further illustrated in FIG. 2A, the implantable medical device 100 is provided with an optional cover 118, according to embodiments. Depending on the nature of the connector 212, such as when the electrical connector 212 is an electrical connector, it may be desirable to protect the connector 212 from environmental elements like blood to ensure proper connectivity. The cover 118 is removable from the implantable medical device 100 for operatively connecting the connector 212 to the controller 226. For example, the cover 118 may be removably attachable to a peripheral cavity 224 where the connector 212 is disposed (as illustrated) or may be removably attachable to the connector 212 directly. The removable attachment of the cover 118 to the implantable medical device 100 may be by interference fit, screwing, and the like.

Figure 3:
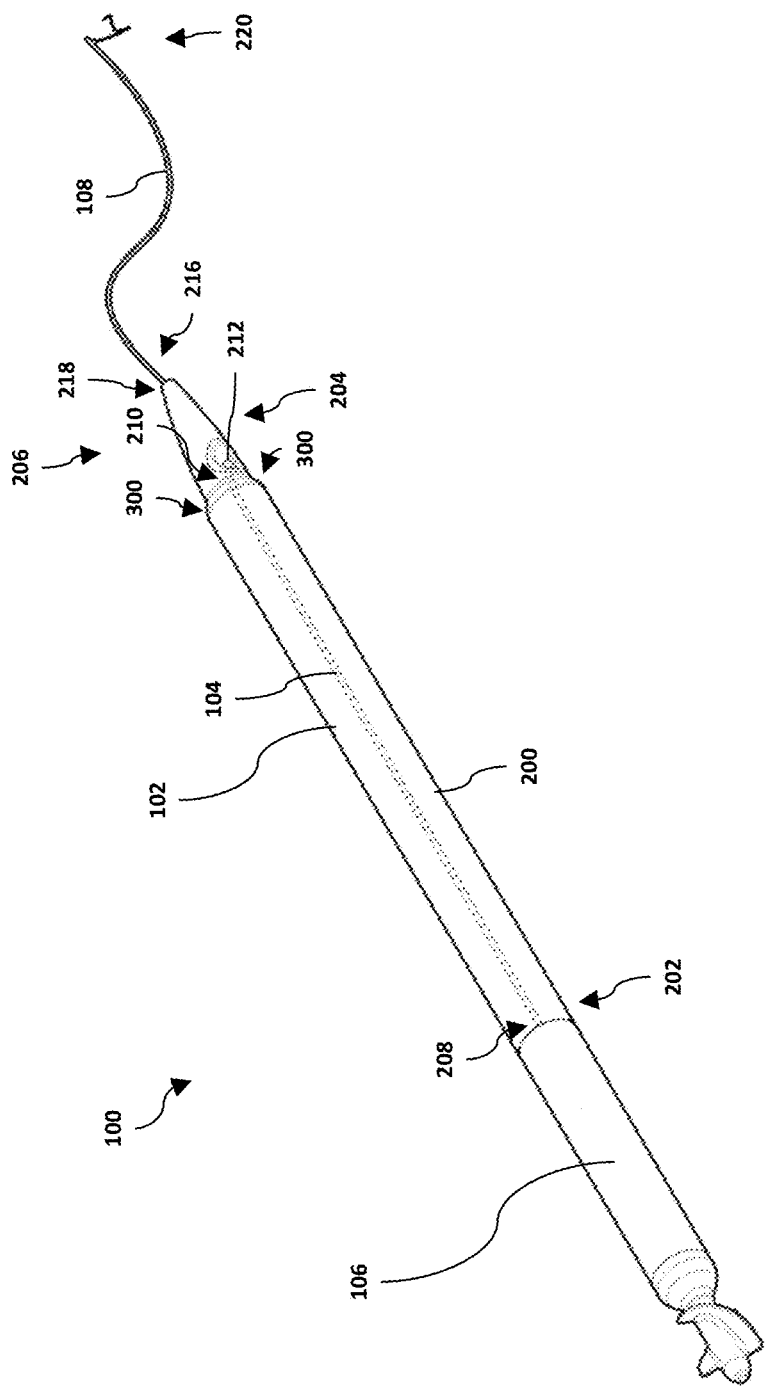
FIG. 3 is a perspective view of the implantable medical device of FIG. 1 provided with a bulge, in accordance with an embodiment.

FIG. 3 illustrates the introducer unit 102 provided with an optional bulge 300 on the distal end portion 204 thereof, according to embodiments. The cover 118 is omitted from FIG. 3 but may be present. Although illustrated as being located near the distal end portion 204 of the introducer unit 102, the bulge 300 may be anywhere along the length of the introducer unit 102, such as at an intermediate portion or near the proximal end portion 202 of the introducer unit 102. The bulge 300 is sized and shaped to disrupt the gradual transverse cross-sectional size increase of the tapered shape of the distal end portion 204. Particularly, the bulge 300 increases the transverse cross-sectional size of the introducer unit 102 more abruptly than the tapered shaped does. Also, the introducer unit 102 may include a plurality of bulges 300 spaced from each other along the length of the introducer unit 102. In this case, each one of the plurality of bulges 300 has a transverse cross-sectional size that increases relative to the preceding one when moving from the distal end portion 204 toward the proximal end portion 202 of the introducer unit 102.

In use, after having introduced the distal end portion 204 of the introducer unit 102 through an intraluminal access and possibly having achieved hemostasis, further introducing one or more bulges 300 through the intraluminal access may facilitates or improves hemostasis by further dilating the intraluminal access to provide a fluid-tight engagement. The difference in transverse cross-sectional size between the distal end portion 204 of the introducer unit 102 and the bulge(s) 300 may be about 0.5 Fr, 1.0 Fr, 1.5 Fr, or 2.0 Fr.

Figure 4A:
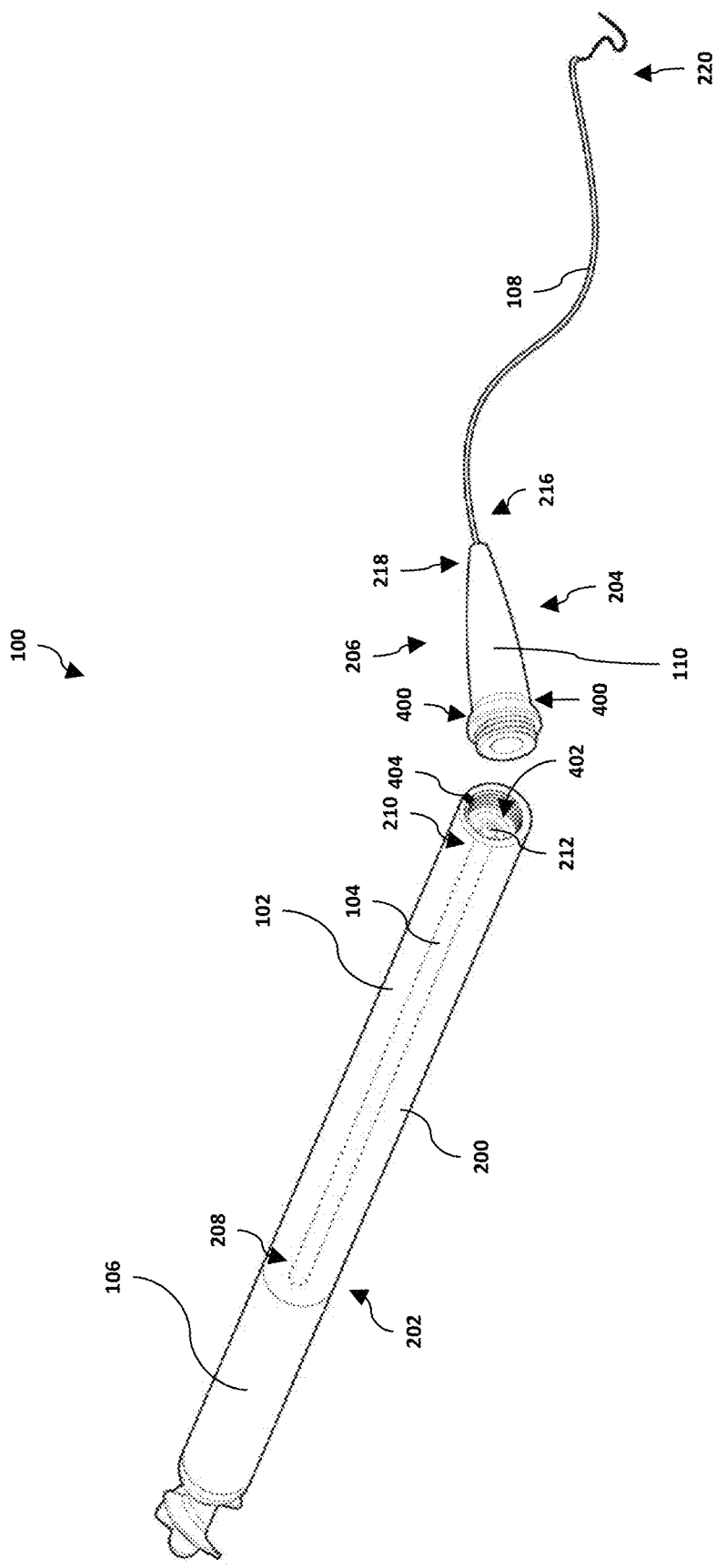
FIGS. 4A-B are a perspective views of the implantable medical of FIG. 1 provided with a tip that is removable, in accordance with an embodiment.
Figure 4B:
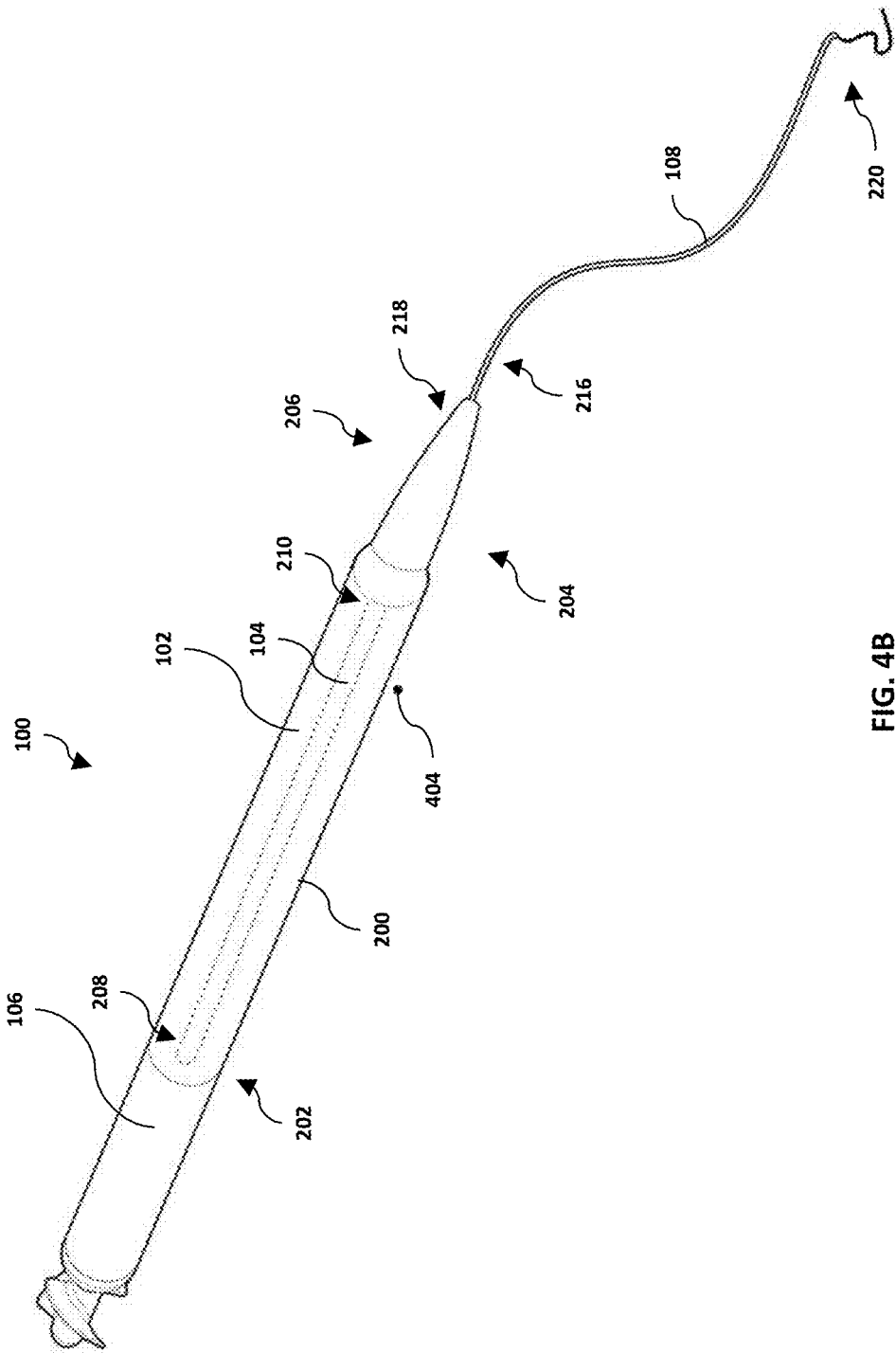

FIGS. 4A-B illustrate the implantable medical device 100 having the distal end portion 204 of the introducer unit 102 provided as an optional tip 110 that is removably attachable to the remainder of the introducer unit 102 and coupled to the guidewire 108, according to embodiments. The tip 110 has a tapered shape that is similar to the tapered shape of the distal end portion 204 of the introducer unit 102 of FIGS. 2A-B. As illustrated, the tip 110 also has an optional bulge 400 that is similar to the bulge 300 of the distal end portion 204 of the introducer unit 102 of FIG. 3. The tip 110 may be attachable to a wireline or other corresponding structure that may be pulled for introducing and/or navigating the implantable medical device 100 inside a lumen of body conduit(s). In this case, such an attachment is strong enough to sustain an appropriate pulling force without breaking in the context of a medical procedures.

As for the cover 118, the tip 110 is provided for protecting the connector 212 from environmental elements like blood when attached to the implantable medical device 100 and is removable therefrom for operatively connecting the connector 212 to the controller. For example, the tip 110 may be removably attachable to a distal cavity 402 where the connector 212 is disposed (as illustrated) or may be removably attachable to the connector 212 directly. The removable attachment of the tip 110 to the implantable medical device 100 may be by screwing (as illustrated), interference fit, and the like. The elongated operable element 104 (shown in dash lines in FIGS. 4A-B as a way to see through the introducer unit 102) is illustrated in FIGS. 4A-B as an electrical conductor configured to transmit electricity from a controller (not shown), when connected thereto, to the pump element 106.

The tip 110 being generally similar to the distal end portion 204 of the introducer unit 102, notably with respect to the tapered shape and bulge(s) thereof, the tip 110 will not be further described herein for the sake of brevity. It will therefore be appreciated that a similar description applies to the tip 110 and the distal end portion 204 of the introducer unit 102, with the necessary change(s), appreciable to the skilled addressee, having been made, if applicable.

As illustrated in FIG. 4A, the implantable medical device 100 provided with the optional locking mechanism 404 configured to lock the tip 110 in place on the introducer unit 102 for preventing unwanted detachment of the tip 110 therefrom, such as when applying a pulling force to the guidewire 108, according to embodiments. As illustrated, the locking mechanism 404 is integrated to the cavity 402 of the introducer unit 102; alternatively, the locking mechanism 404 may be integrated anywhere along the length of the introducer unit 702. The locking mechanism 404 may be useful when the tip 110 is removably attached to the introducer unit 102 by interference fit.

The locking mechanism 404 may include a set screw and other similar engagement structures provided to the introducer unit 102 that removably engages the tip 110 to lock it. Alternatively, the locking mechanism 404 may also include a first portion provided to the introducer unit 102 and a second portion provided to the tip 110. The first and second portions are configured to selectively engage each other to lock them together. In this case, the first portion may be a pin and other corresponding engagement structure, while the second portion may be an aperture and other corresponding engagement structure configured to cooperatively engage the first portion.

Figure 5A:
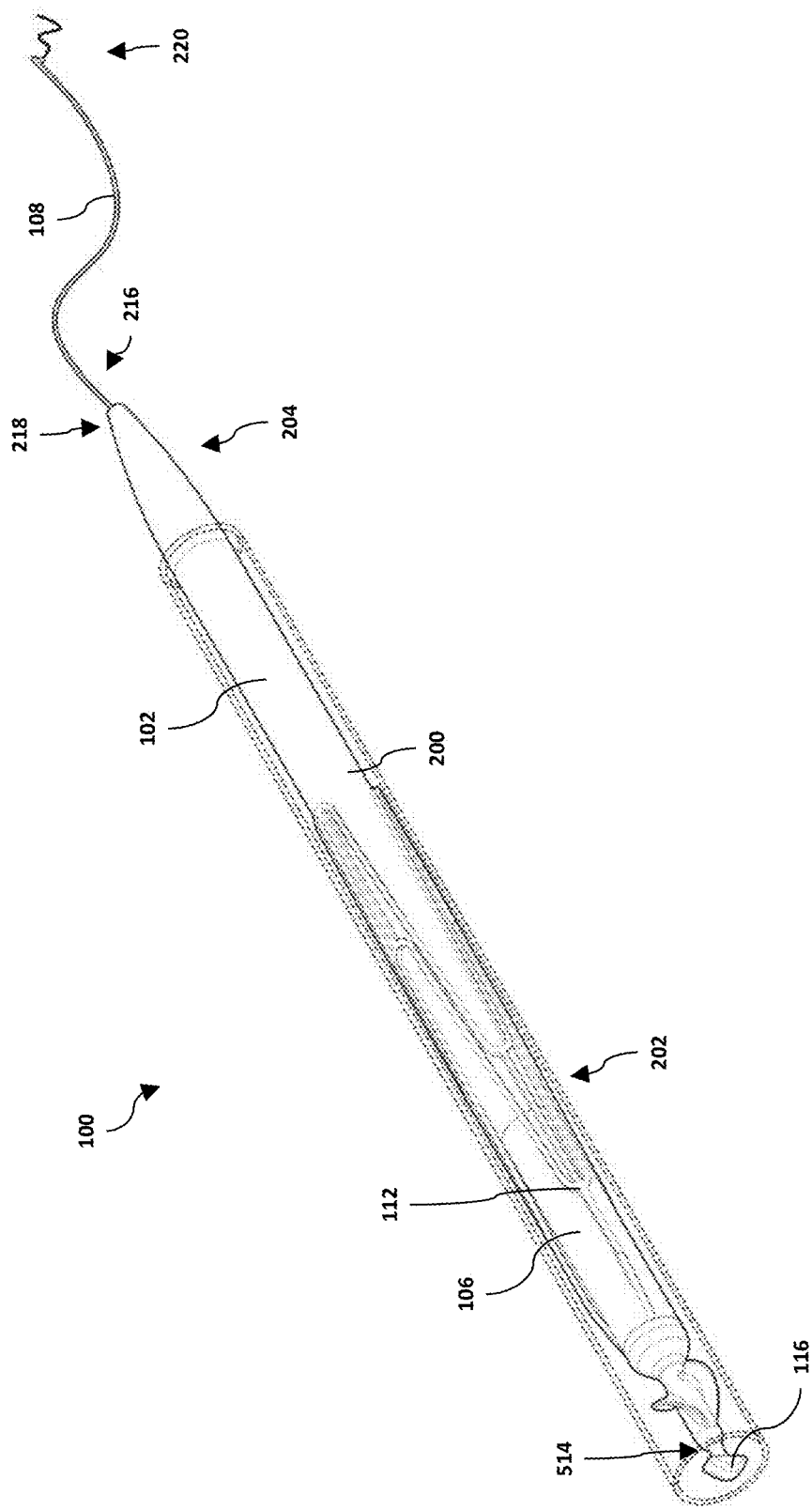
FIGS. 5A-D are a perspective views of the implantable medical of FIG. 1 provided with an anchor, in accordance with an embodiment.

FIGS. 5A-D illustrate the implantable medical device 100 provided with the optional anchor 112 having a contracted configuration (FIGS. 5A,C) and an expanded configuration (FIGS. 5B,D), according to embodiments. As illustrated in FIGS. 5A,C, the anchor 112 in the contracted configuration may be contained in a sheath (shown in dash lines as an optional component of the implantable medical device 100) for implanting and/or explanting the implantable medical device 100. Although the implantable medical device 100 is illustrated with the tip 110 in FIGS. 5A-D, the implantable medical device 100 may alternatively be provided with the cover 118.

The anchor 112 in the contracted configuration, either contained or not in a sheath, is introducible and navigable in a lumen of body conduit(s). The anchor 112 in the expanded configuration is configured to removably anchor the implantable medical device 100 in a lumen of body conduit(s) by removably engaging a lumen wall thereof. The anchor 112 is deployable in a lumen of body conduit(s), for example at an intraluminal implantation site thereof where the pump element 106 is desired to be immobilized for operation. Anchoring of the implantable medical device 100 allows not only the pump element 106 to remain in place at the intraluminal implantation site for producing an appropriate hemodynamic effect, but also the distal end portion 204 of the introducer unit 102 to remain appropriately in place through an intraluminal access, such as a percutaneous intraluminal access, for facilitating or helping preserving hemostasis.

Figure 5B:
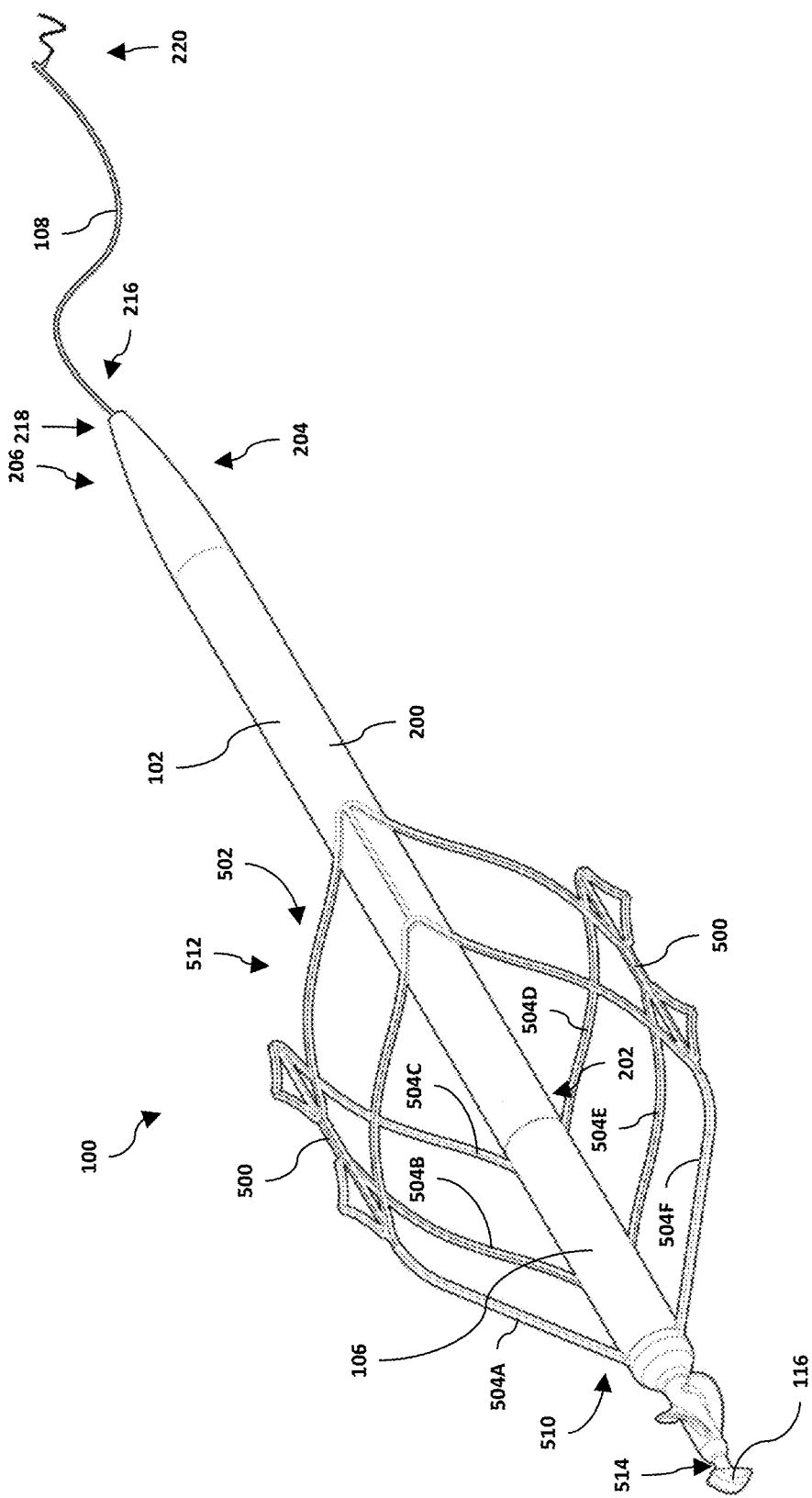

As best illustrated in FIG. 5B, the anchor 112 has a tubular wall 500 that defines a central opening 502 and includes at least one anchor arm, such as six anchor arms 504A-F as illustrated, linking the tubular wall 500 to the pump element 106 and positioning the pump element 106 and/or the introducer unit 102 at least partially within the central opening 500. Alternatively, the tubular wall 500 may be attached to the introducer unit 102 by at least one anchor arm, such as the anchor arms 504A-F, so as to position the pump element 106 and/or the introducer unit 102 at least partially within the central opening 502. As such, the anchor 112 may be generally structured as a stent-like structure, an array-like structure, and/or a scaffold-like structure.

Figure 5C:
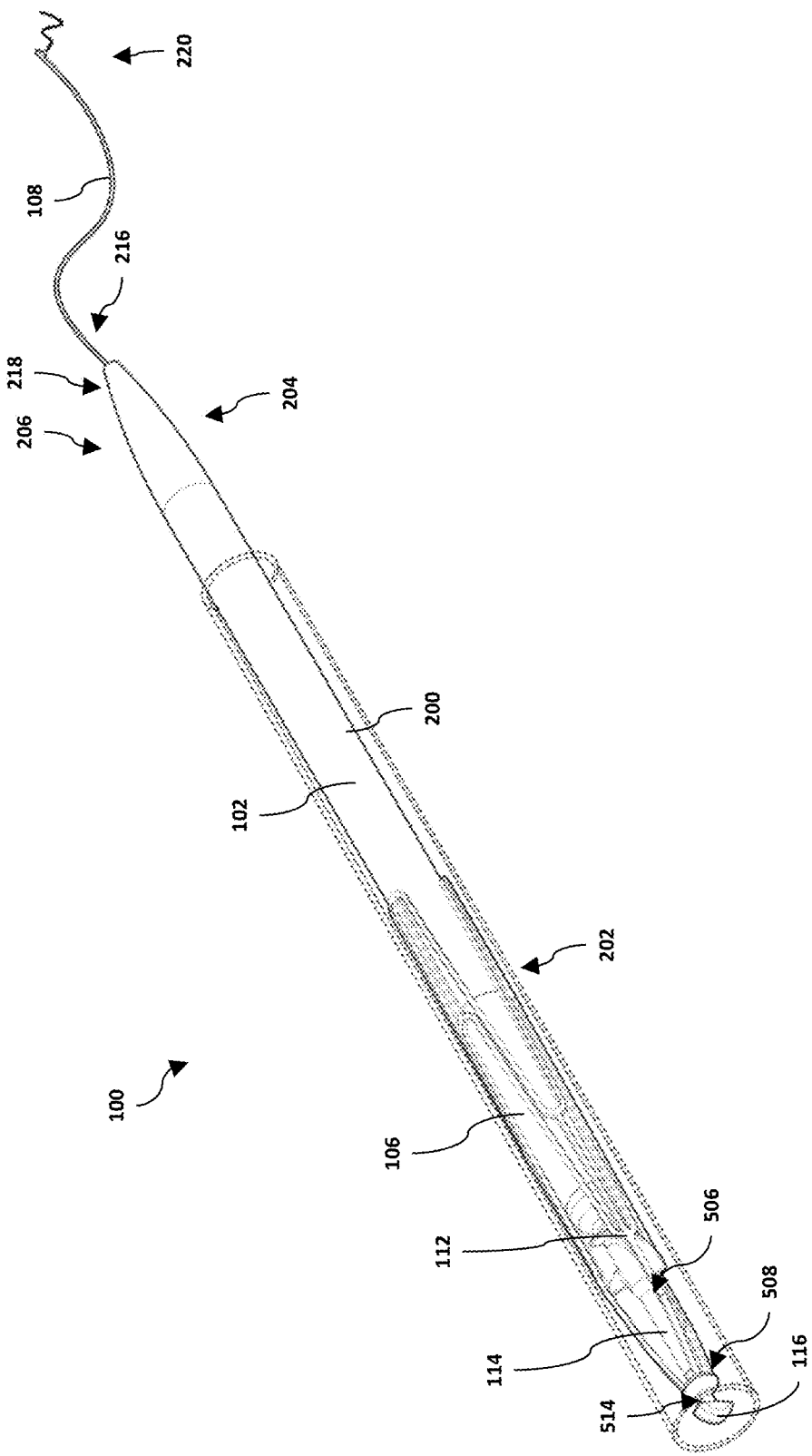
Figure 5D:
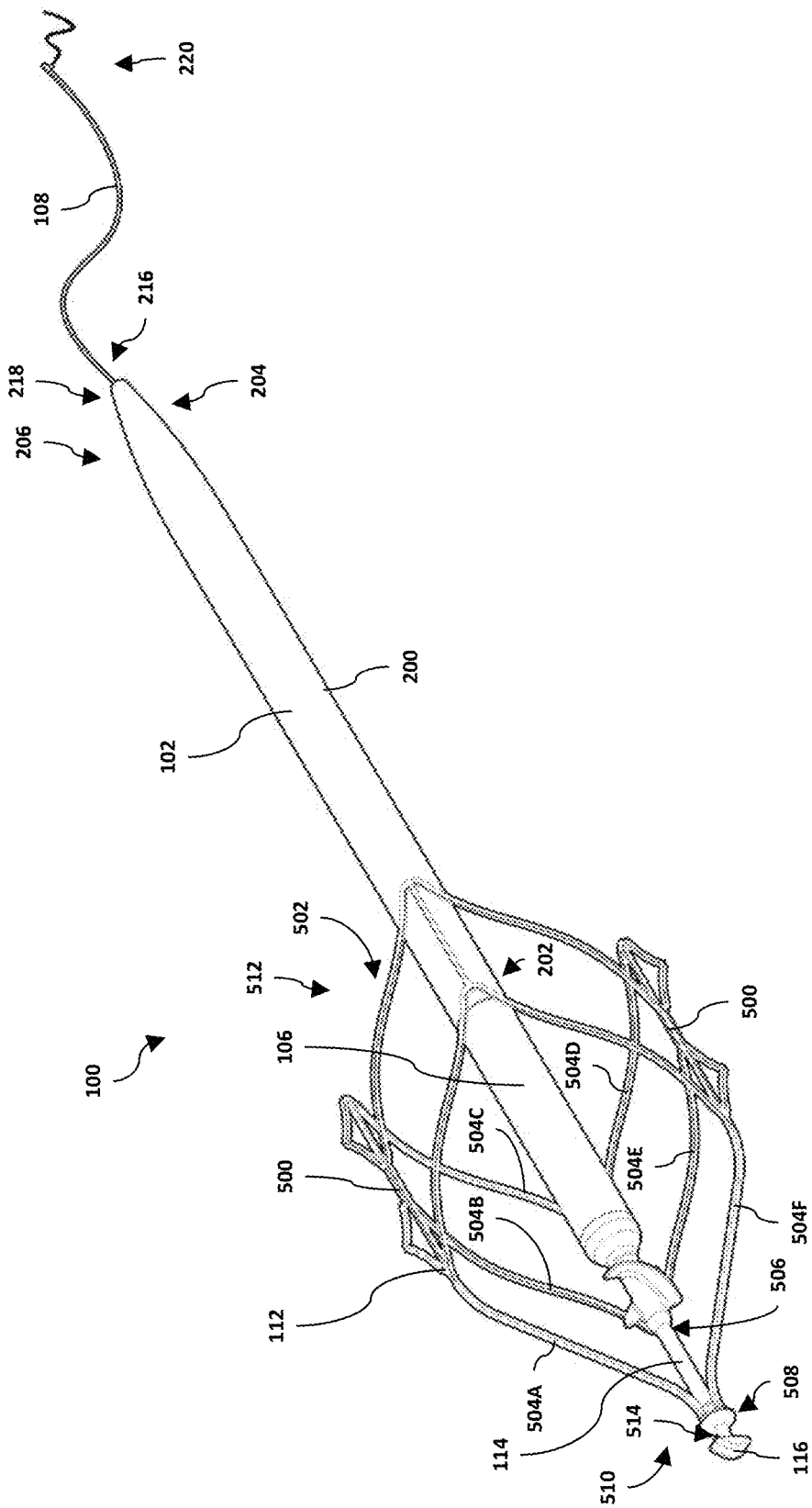

As illustrated in FIGS. 5C-D, the implantable medical device 100 is provided with the optional anchor rod 114 supporting the anchor 112, according to embodiments. The distal end portion 506 of the anchor rod 114 is attached to the pump element 106. At least one anchor arm, such as the anchor arms 502A,F as illustrated, links the proximal end portion 508 of the anchor rod 114, at least one anchor arm, such as the anchor arms 502B,E as illustrated, links the distal end portion 506 of the anchor rod 114, and at least one anchor arm, such as the anchor arms 502C, D as illustrated, links the pump element 106. Alternatively, at least one anchor arm, particularly three anchor arms 504, may only link the proximal end portion 508 of the anchor rod 114. Linked by one or more of the anchor arms 504A-F, the pump element 106 and/or the introducer unit 102 is/are at least partially positioned within the central opening 502 defined by the tubular wall 500.

As illustrated in FIGS. 5B,D, the anchor 112 is so sized and shaped that its transverse cross-sectional size progressively increases moving from a proximal end portion 510 thereof toward the distal end portion 512 thereof. Therefore, as illustrated, the anchor 112 is tapered and/or profiled in shape (referred herein to as "tapered"). Such tapered shape may be not limited to the shape illustrated in FIGS. 5B,D, since the anchor 112 may be void of the tubular wall 500 and only have three anchor arms 504, which in this case may include an atraumatic lumen wall engaging end portion.

The anchor 112 is convertible between the contracted configuration (as illustrated in FIGS. 5A,C) and an expanded configuration (as illustrated in FIGS. 5B,D). In the contracted configuration, the tubular wall 500 and the anchor arms 504A-F are radially disposed relatively close, as compared to the expanded configuration, to the pump element 106 and/or the introducer unit 102. In the expanded configuration, the tubular wall 500 and the anchor arms 504A-F are radially disposed relatively away, as compared to the contracted configuration, from the pump element 106 and/or the introducer unit 102, so as the anchor 112 can removably engage in use a lumen wall of body conduit(s) and thus removably anchor the implantable medical device 100 thereto.

The anchor 112 may be self-expandable (also referred herein to as a "self-expandable anchor") and thus may be overcomeably biased toward the expanded configuration. In this case, the self-expandable anchor 112 may be restrained in the contracted configuration by a sheath containing the implantable medical device 100 therein, as illustrated in FIGS. 5A-C. When self-expandable, the anchor 112 may be made of a material conferring such property, such as nitinol, stainless steel, polymers, plastics, and the like.

In use, the implantable medical device 100 contained in a sheath (i.e., "sheathed") is deliverable and/or implantable at an intraluminal implantation site in a lumen of body conduit(s) with the self-expandable anchor 112 restrained in the contracted configuration by the sheath, as illustrated in FIGS. 5A,C. After introduction of the sheath in the lumen of the body conduit(s) through an intraluminal access thereof, such as a percutaneous intraluminal access, and navigation of the sheath up to an intraluminal implantation site, the implantable medical device 100 is removed from the sheath for implantation (i.e., "unsheathed"), thereby releasing the restrain imposed on the self-expandable anchor 112 by the sheath and causing the self-expandable anchor 112 to autoconvert from the contracted configuration to the expanded configuration, as illustrated in FIGS. 5B,D.

Alternatively, the anchor 112 may be converted from the collapsed configuration to the expanded configuration in a lumen of body conduit(s) by a balloon catheter that is inserted in the central opening 500 and then inflated. In this case, the anchor 112 is not self-expandable, but malleable. Accordingly, the anchor 112 may be made of a material conferring such property, such as cobalt-chromium alloys, and the like.

In absence of the self-expandable anchor 112, the implantable medical device 100 may be deliverable and/or implantable in a lumen of body conduit(s) with or without the use of a sheath.

Still in use, the implantable medical device 100 is retrievable from an intraluminal implantation site in a lumen of body conduit(s) using a sheath. Introduced in a lumen of the body conduit(s) through a first intraluminal access, such as a percutaneous intraluminal access, and approaching the implantable medical device 100 from the impeller side end portion thereof (i.e. the proximal end portion of the implantable medical device 100), the sheath is gradually slid over the self-expandable anchor 112 in the expanded configuration. To maintain the implantable medical device 100 in place in the lumen, the distal end portion 206 of the implantable medical device 100 may be held and immobilized by an operator through a second intraluminal access, such as a percutaneous intraluminal access. Alternately, the distal end portion 206 of the implantable medical device 100 may be pushed toward the sheath by an operator through the second intraluminal access. As the sheath is slid over the expandable anchor 112, the sheath exerts pressure to the proximal end portion 510 of the self-expandable anchor 112, which as illustrated is tapered, causing the self-expandable anchor 112 to gradually convert from the expanded configuration to the contracted configuration. Then, the sheath containing the implantable medical device 100 (i.e., "sheathed") is removed from the lumen of the body conduit, thereby explanting the implantable medical device 100.

In absence of the self-expandable anchor 112, the implantable medical device 100 may be retrievable and/or explantable from a lumen of body conduit(s) with or without the use of a sheath.

Still referring to FIGS. 5A-D, the implantable medical device 100 is provided with an optional capture element 116 that is capturable in vivo by a tool, such as a snare and the like, to pull or maintain in place the implantable medical device 100 in a lumen of body conduit(s), according to embodiments. The capture element 116 may be located on the pump element 106 (as illustrated in FIGS. 5A-B) or on the proximal end portion 508 of the anchor rod 114 (as illustrated in FIGS. 5C-D), and is capturable in use from the proximal end portion 510 of the anchor 112.

The capture element 116 may have any size and shape enabling its intraluminal capture by a tool. For example, as illustrated in FIGS. 5A-D, the capture element 116 defines an annular recess 514 that a lasso of a snare may encircle to capture the capture element 116. Alternatively, the capture element 116 may be a hook that is intraluminally capturable by a snare or like tool, or a loop that is intraluminally capturable by a hook tool or like tool.

The capture element 116 may be used to explant the implantable medical device 100 from a lumen of body conduit(s). Particularly, in use, a sheath is introduced through a first intraluminal access, such as a percutaneous intraluminal access, in a lumen of body conduit(s) and is navigated therein to approach the self-expandable anchor 112 from the proximal end portion 510 thereof. A snare passing in the sheath captures the capture element 116. The snare is pulled such that the implantable medical device 100 is caused to enter the sheath. The sheath may be pushed through the first intraluminal access toward the implantable medical device 100 while the snare is or is not being pulled. The distal end portion 206 of the implantable medical device 100 may also be pushed through a second intraluminal access, such as a percutaneous intraluminal access, which receives the implantable medical device 100, toward the sheath while the snare is or is not being pulled. Then the sheath containing the implantable medical device 100 is removed from the lumen of the body conduit(s) to explant implantable medical device 100.

The capture element 116 may also be used to convert the self-expandable anchor 112 from the expanded configuration to the contracted configuration during explanation. Particularly, with the sheath abutted to the proximal end portion 510 of the self-expandable anchor 112 in the expanded configuration, the snare is pulled such that the sheath exerts a pressure on the proximal end portion 510 of the self-expandable anchor 112, which is of a tapered shape, causing the conversion of the self-expandable anchor 112 from the expanded configuration to the contracted configuration. As described hereinbefore, the sheath may be pushed through the first intraluminal access toward the implantable medical device 100 and/or the distal end portion 206 of the implantable medical device 100 may be pushed through a second intraluminal access for assisting the conversion while the snare is or is not being pulled.

The coaxial disposition of the capture element 116 relative to the implantable medical device 100 facilitates the sheathing of the implantable medical device 100 in the sheath and the conversion of the anchor 112 from the expanded configuration to the contracted configuration since pressure is applied uniformly to the proximal end portion 510 of the anchor 112 by the sheath.

The capture element 116 may be made of a radio-opaque material, such as nitinol, that is visible by medical imaging, such as by fluoroscopy, to assist in or facilitate the intraluminal capture of the capture element 116 by a tool. To facilitate the observation by medical imaging of a capture element 116 that may be disposed relatively close to an impeller, as illustrated in FIGS. 5A-B, the impeller may be made of a non-radio-opaque material.

Referring back to FIGS. 1 to 5, the implantable medical device 100 is provided with an optional guidewire 108 that is attachable to the implantable medical device 100 and pullable for moving the implantable medical device 100 in a lumen of body conduit(s), according to embodiments. As illustrated in FIGS. 2A-B to 5, the guidewire 108 has a proximal end portion 216 that is attached to the distal end portion 204 of the introducer unit 102, which may be the tip 110, for example on a tapered distalmost end portion 218 thereof. The attachment of the guidewire 108 to the introducer unit 102 or to the tip 110 may be rotatable and/or removable.

The distal end portion 220 of the guidewire 108 may also be capturable intraluminally by a tool, such as by a snare and the like, which may be pulled for introducing and/or navigating the implantable medical device 100 in a lumen of body conduit(s). Particularly, the distal end portion 220 of the guidewire 108 may be floppy. The distal end portion 220 of the guidewire 108 may be floppier than the proximal end portion 216 of the guidewire 108, that is the proximal end portion 216 may be stiffer than the distal end portion 220. Such stiffer properties may help routing the guidewire 108 in lumen(s) of body conduits by pushing on the proximal end portion 216 of the guidewire 108. Alternatively, the entire guidewire 108 may be floppy in nature. The floppy nature of the guidewire 108 enables a tool to capture it intraluminally by folding the floppy portion thereof back on itself at an inflexion point formed by the snare. So folded, the guidewire 108 and the tool can be moved along a lumen of body conduit(s) and through intraluminal accesses without significant resistance and/or damaging or injuring the lumen wall.

Alternatively, the distal end portion 220 of the guidewire 108 may be provided with a hook that is capturable intraluminally by a snare or like tool, or may be provided with a loop that is capturable by a tool equipped with a hook or similar like structure that can catch a loop.

The attachment between the guidewire 108 and the introducer unit 102, the guidewire 108 and the tip 110, and the tip 110 and the remainder of the introducer unit 102, as the case may be, is strong enough to sustain the appropriate pulling of the guidewire 108 without detaching the tip 110 and/or damaging the implantable medical device 100. Accordingly, such attachment, may be implemented by gluing, fusing, welding, or screwing the components together, or by implementing the locking mechanism 404, as the case may be.

The guidewire 108 may include an electrical conductor extending at least partially between the proximal end portion 216 and the distal end portion 220 thereof, which may or may not be floppy, according to embodiments. The electrical conductor is electrically connected, at proximal end portion 216, to the elongated operable element 104, which in this case is also an electrical conductor, as described hereinbefore. The guidewire 108 integrates, at the distal end portion 220, an electrical connector that is removably connectable to a controller for operating the pump element 106.

In use, the distal end portion 220 of the guidewire 108 is introduced through a first intraluminal access, such as a first percutaneous access, and the guidewire 108 is routed in a lumen of body conduit(s). The distal end portion 220 of the guidewire 108 is captured by a tool, such as a snare, routed through a second intraluminal access, such as a second percutaneous access. The snare capturing the guidewire 108 is then pulled to move the guidewire 108 along a lumen of body conduit(s) up to the second intraluminal access and passed therethrough. Doing so, depending on the length of the guidewire 108, the implantable medical device 100 may be introduced in the first intraluminal access and/or navigated in the lumen of the body conduit(s) where the guidewire 108 was initially routed. While the guidewire 108 is pulled, the proximal end portion 202 of the introducer unit 102 me be pushed to assist or facilitate introduction and/or movement.

In some circumstances, it may be desirable to pull the guidewire 108 to advance the implantable medical device 100 in a lumen of body conduit(s) since only pushing on the implantable medical device 100 causes the implantable medical device 100 to go in unwanted directions. Advantageously, the integration of the guidewire 108 to the implantable medical device 100 enables the implantable medical device 100 to be introduced and navigated in a lumen of body conduit(s) that would not be possible in absence of the guidewire 108. Indeed, depending on their morphology, body conduit(s) may be so tortuous that one or more acute angles may prevent appropriate introduction and/or navigation of other implantable medical devices therein without damaging or injuring the lumen wall. Particularly, other implantable medical devices may be so sized, shaped, and/or stiff in nature that they cannot pass through such acute angles. On the other hand, being appropriately sized and generally smaller and more flexible than at least some implantable medical devices, the guidewire 108 can pass through theses acute angles. Such a situation is illustrated in FIGS. 23A-C and 25A-J and will be described in further detail hereinafter. When routed in a lumen of body conduit(s), the guidewire 108 may be advantageously pulled to assist or facilitate the introduction and/or navigation of the implantable medical device 100, while, optionally, the implantable medical devices is being pushed simultaneously. The combined pulling and pushing actions may enable a smoother medical procedure that is less traumatizing to the lumen wall.

The guidewire 108 enables the implantable medical device 100 to be pulled intraluminally in a direction, whereas the implantable medical device 100 may be pulled in an opposite direction via the capture element 116, which altogether may be desirable to appropriately position the implantable medical device 100 intraluminally, depending on the medical procedure performed.

The connection between the guidewire 108 and the implantable medical device 100 is also advantageously stronger than the typical attachment between tools like snares and implantable medical devices. Such stronger connection enables the implantable medical device 100 to sustain an appropriate pulling force in the context of a medical procedure without breaking. This is not necessarily the case for typical attachment between snares and implantable medical devices.

It will be appreciated that these advantages are present whether the implantable medical device 100 is pulled by the guidewire 108 or by the distal end portion 206 of the implantable medical device 100 by a tool, such as a snare.

Figure 6:
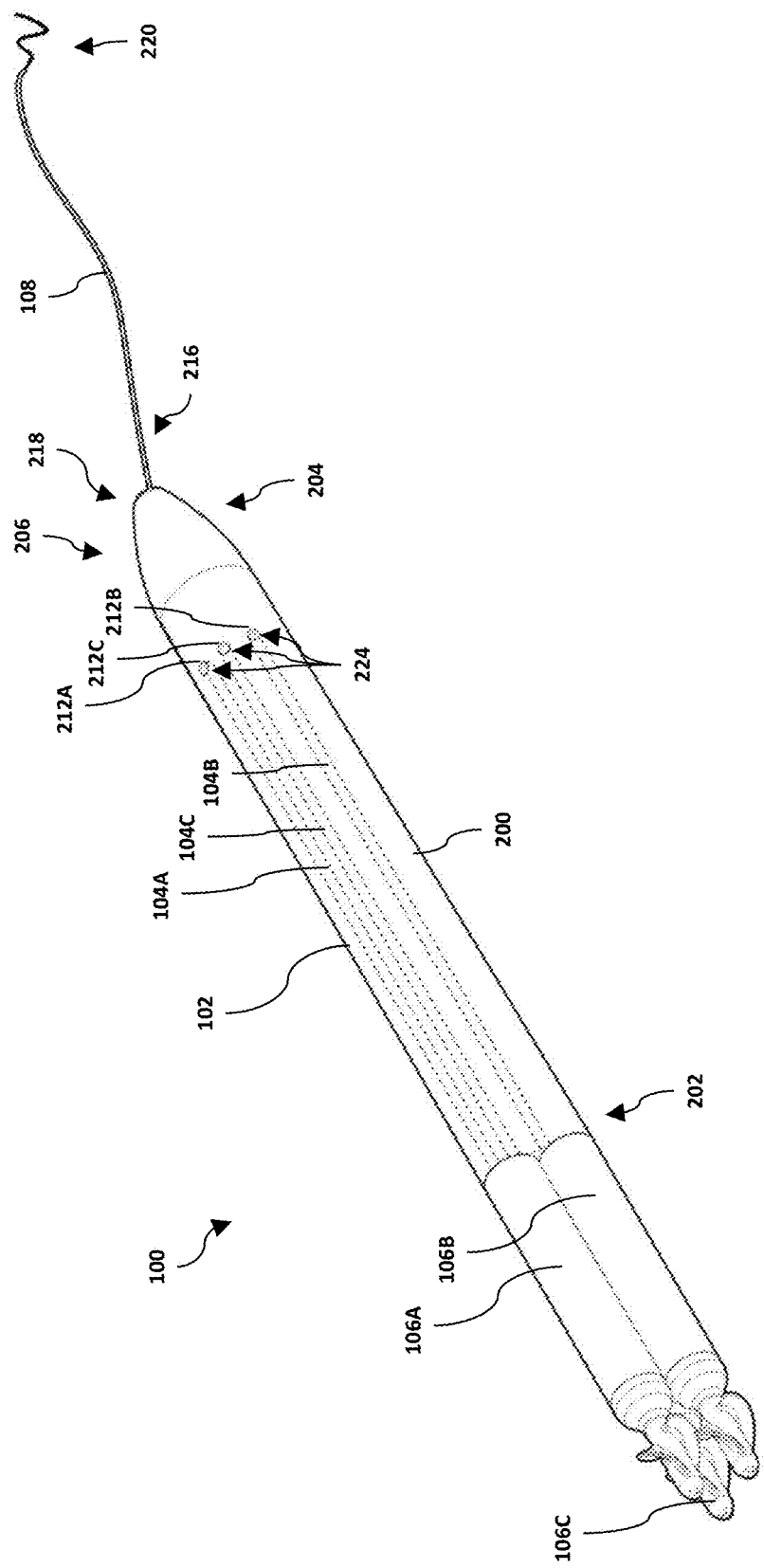
FIG. 6 is a perspective view of the implantable medical device of FIG. 1 provided with a plurality of pump elements, in accordance with an embodiment.

FIG. 6 illustrates the implantable medical device 100 that includes an optional plurality of pump elements 106, three pump elements 106A-C as illustrated, provided as functional units 105, according to embodiments. Each one of the pump elements 106A-C is coupled to the proximal end portion 202 of the introducer unit 102 and is arranged generally in parallel relative to each other and also to the introducer unit 102. The introducer unit 102 is provided with a corresponding optional plurality of elongated operable elements, three elongated operable elements 104A-C as illustrated (shown in dash lines as a way to see through the introducer unit 102). Each one of the elongated operable elements 104A-C extends at least partially along the introducer unit 102 and is operatively connected, at a respective proximal end portion thereof, to a corresponding one of the three pump elements 106A-C, and is operatively connectable, at a respective distal end portion thereof, to at least one controller (not shown) by a respective connectors 212A-C. Each one of the connectors 212A-C is disposed in a respective peripheral cavity 224, as illustrated, and may be provided with corresponding optional covers. Alternatively, the connectors 212A-C may be disposed in a single, common peripheral cavity and be provided with an optional cover.

The pump elements 106A-C may be longitudinally offset relative to each other so that each one of the impeller end portions of the pump elements 106A-C are longitudinally positioned differently. Additionally or alternatively, the pump elements 106A-C may or not be arranged parallel relative to each other so that each one of the impeller end portions of the pump elements 106A-C are spaced apart by a greater distance than a distance between each one of the introducer unit contacting end portions of the pump elements 106A-C. Depending of the pump elements 106A-C, such positioning and spacing may improve the pumps' performance, including better fluid outflow and reduced fluid shear stress, which in the latter case may lead to hemolysis and/or thrombogenesis for blood.

The pump elements 106A-C and the introducer unit 102 may have a same transverse cross-sectional size, as illustrated in FIG. 6. Alternatively, the pump elements 106A-C may have a transverse cross-sectional size that is larger than a transverse cross-sectional size of the introducer unit 102, as described for and illustrated in FIG. 13B for the implantable medical device 700 in the assembled configuration.

The implantable medical device 100 of FIG. 6 may also be provided with the optional tip 110 and optional locking mechanism 404, the optional anchor 112, the optional anchor rod 114, one or more optional capture elements 116, and the optional guidewire 108. When provided with the anchor 112, the pump elements 106A-C may be longitudinally received at least partially in the central opening 502 of the anchor 112, and the at least one of the anchor arms 504A-F may link the anchor 112 to one or more of the pump elements 106A-C and/or to the introducer unit 102. When provided with the anchor rod 114, the pump elements 106A-C may be disposed about the anchor rod 114. When provided, the capture element 116 may be present on one or more pump elements 106A-C.

The implantable medical device 100 provided with the plurality of pump elements 106A-C being similar to the implantable medical device 100 provided with a single pump element 106, the description of the implantable medical device 100 provided with the plurality of pump elements 106A-C will not be further described herein for the sake of brevity. It will therefore be appreciated that the description of the implantable medical device 100 provided with a single pump element 106 applies to the implantable medical device 100 provided with the plurality of pump elements 106A-C, with the necessary change(s), appreciable to the skilled addressee, having been made, if applicable.

With reference now to FIGS. 7 to 14A-D, an implantable medical device 700 will be described, in accordance with a second aspect of the present disclosure.

Figure 7:
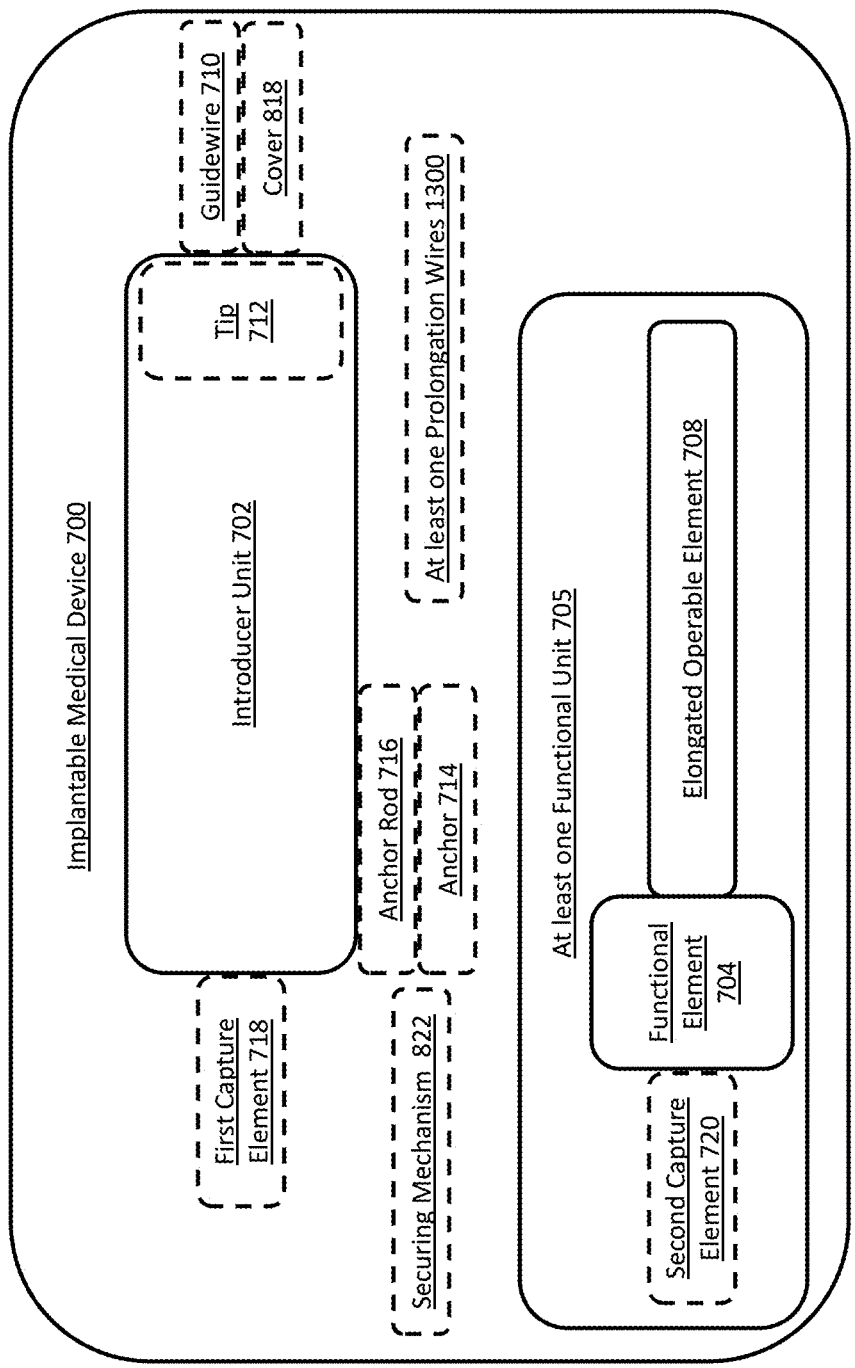
FIG. 7 is a schematic representation of an implantable medical device provided with an introducer unit and a functional unit having an elongated operable element in a slidable relationship with the introducer unit, in accordance with a second aspect of the present technology.

FIG. 7 schematizes the implantable medical device 700, according to embodiments. The implantable medical device 700 includes an introducer unit 702 and at least one functional unit 705 having a functional element 704 and an elongated operable element 708 operatively connected to the functional element 704 for operation. In the second aspect of the present disclosure, the introducer unit 702 and the functional unit 705 are in a slidable relationship and form two distinct, separate devices working together.

Particularly, the introducer unit 702 and the functional element 704 may be assembled together and may also be unassembled from each other by a relative sliding movement between the introducer unit 702 and the elongated operable element 708. The implantable medical device 700 may be deliverable in and retrievable from a lumen of body conduit(s) when the introducer unit 702 and the functional element 704 are unassembled form each other. The implantable medical device 700 may be implanted in a lumen of body conduit(s) when the introducer unit 702 and the functional element 704 are assembled together or when the introducer unit 702 and the functional element 704 are unassembled from each other. The introducer unit 702 may serve as a percutaneous dilator that slidably receives the elongated operable element 708 of the functional unit 705 therethrough, such that the functional unit 705 is implanted in vivo with the assistance of introducer unit 702 and is operated through the elongated operable element 708 from outside a subject's body. The functional unit 705 is operable via the elongated operable element 708, such as by being electrically or mechanically operated, when the elongated operable element 708 is operatively connected to a controller (not shown). Such operation may produce a hemodynamic effect in a subject's body.

The introducer unit 702 is configured not only to be introduced, guided, and navigated in a lumen of body conduit(s), but also to route the elongated operable element 708 of the functional unit 705 along the lumen of body conduit(s) for implanting the functional unit 705 to an intraluminal implantation site thereof through their slidable relationship. As such, the functional unit 705 is operated in the lumen via the elongated operable element 708 that is slidably received thought the introducer unit 702 and operatively connected to a controller outside the lumen.

When the implantable medical device 700 is implanted in a lumen of body conduit(s) with the introducer unit 702 and the functional unit 705 assembled together, the introducer unit 702 is positioned partially extraluminally outside a lumen of body conduit(s) through an intraluminal access, while the functional unit 705 is positioned intraluminally in a lumen of the body conduit(s).

As schematically illustrated in FIG. 7, the implantable medical device 700 may further include, for example, a guidewire 710, a tip 712, an anchor 714, an anchor rod 716, a first capture element 718, a second capture element 720, a cover 818, and a securing mechanism 824 (optional items are represented by dash lines in FIG. 7), as it will be described hereinafter. The implantable medical device 700 may also optionally include more than one functional unit 705.

Figure 8A:
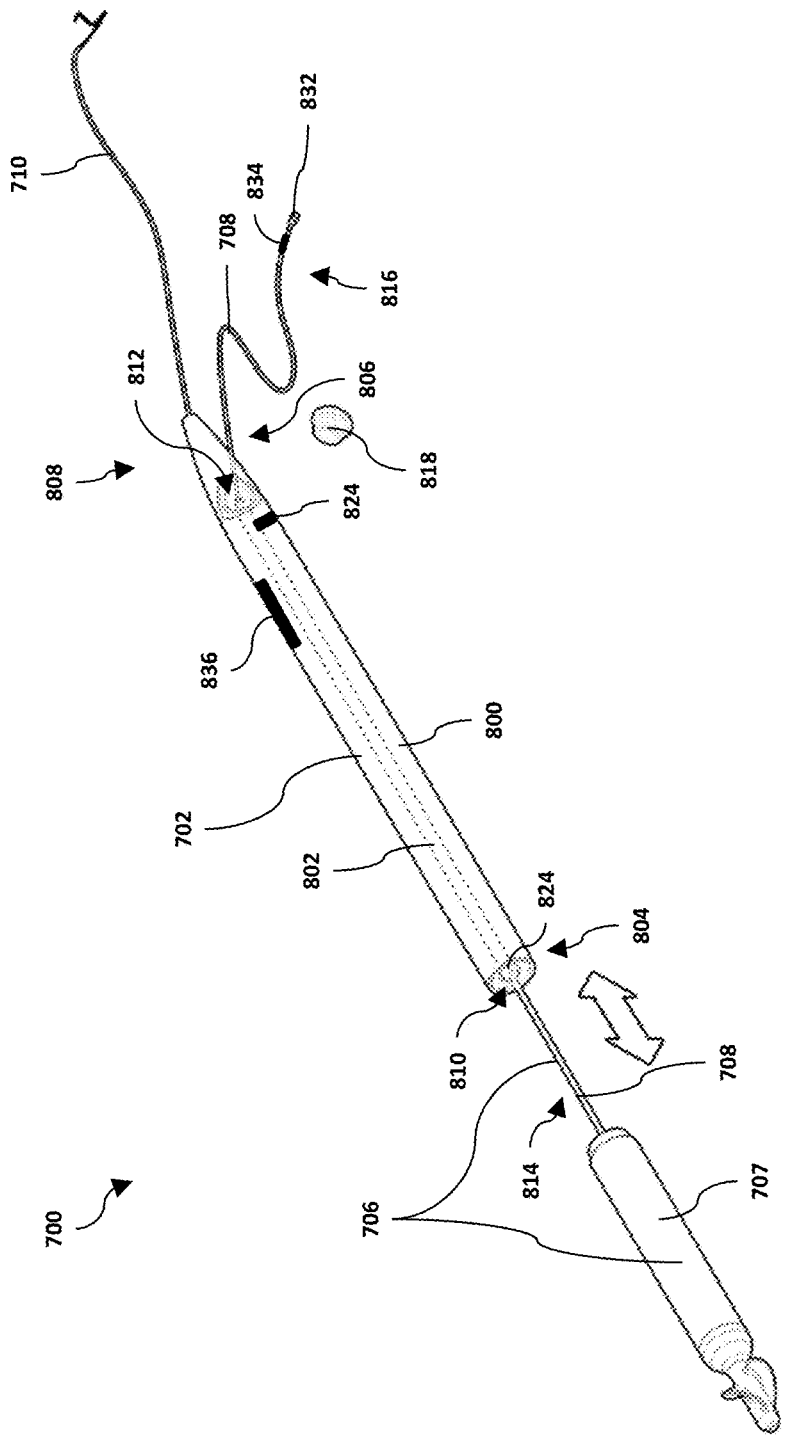
FIGS. 8A-C are perspective views of an implantable medical device that is slidable, such as one of FIG. 7, in accordance with an embodiment.
Figure 8B:
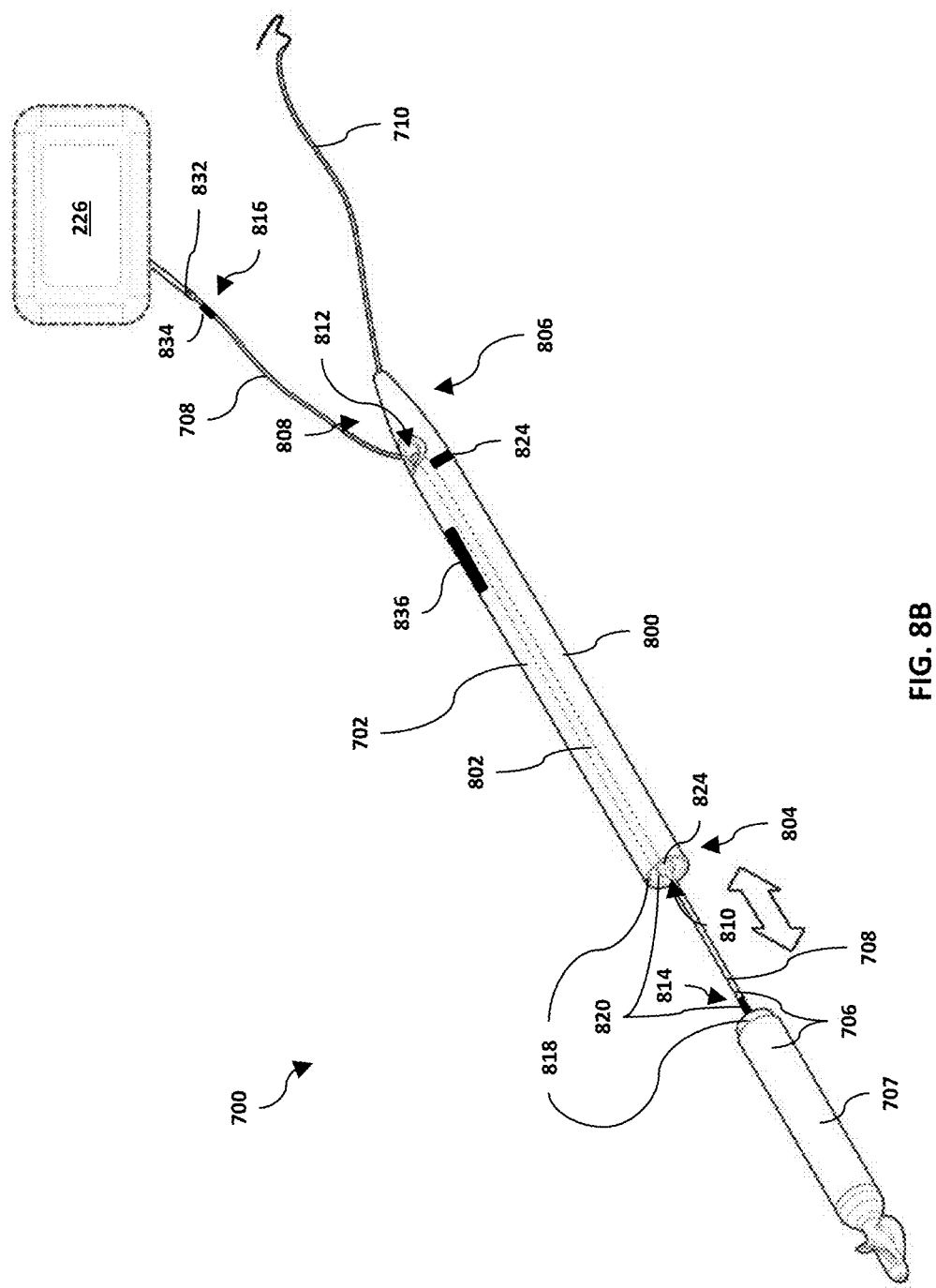
Figure 8C:
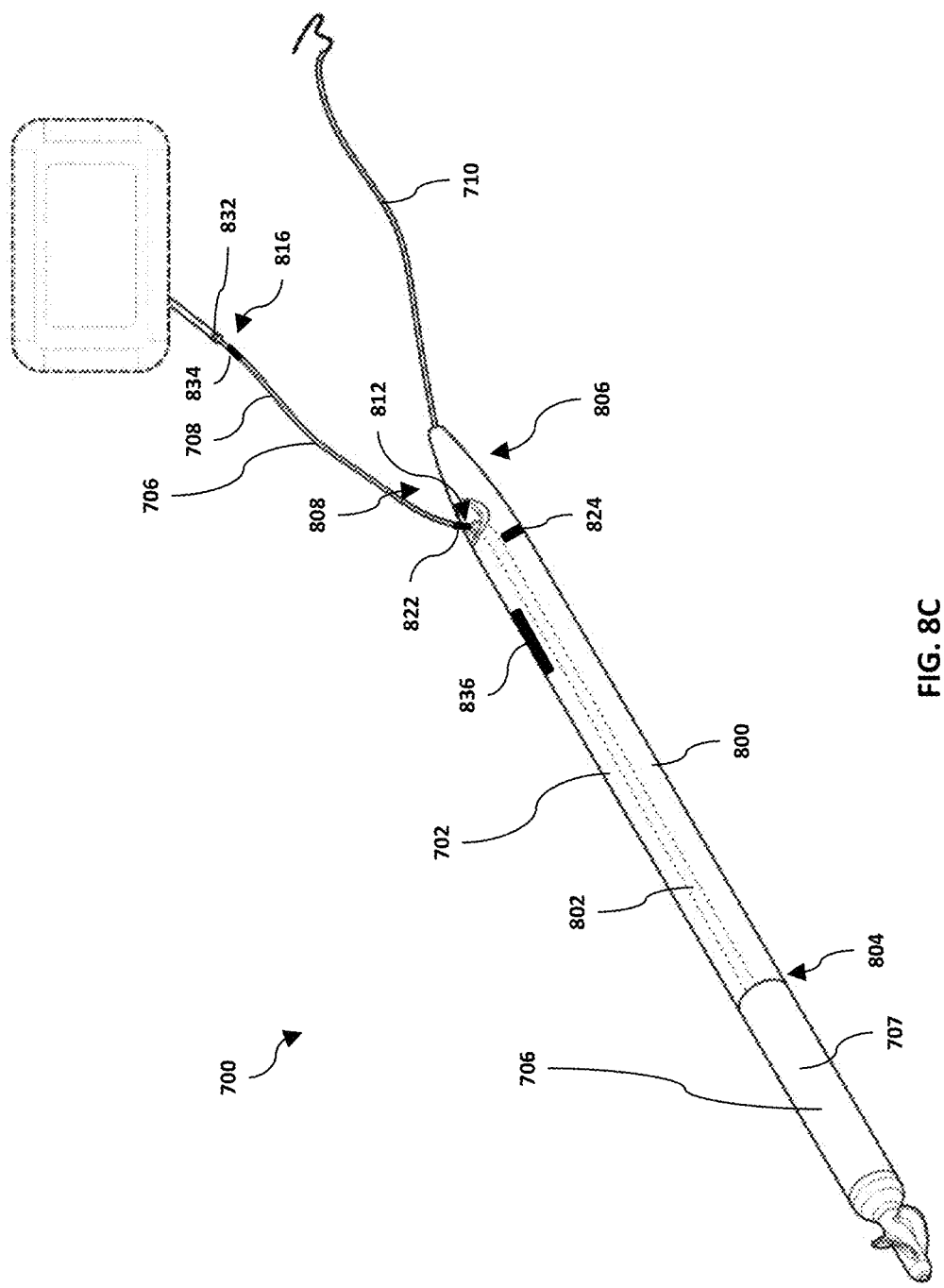

FIGS. 8A-C illustrate the implantable medical device 700 that includes the introducer unit 702 and a pump unit 706 provided as the functional unit 705, according to embodiments. The introducer unit 702 has a body 800 defining a longitudinal guide hole 802 (shown in dash lines as a way to see through the introducer unit 702 in FIGS. 8A,C). The pump unit 706 has a pump element 707, provided as the functional element 704, and the elongated operable element 708 operatively connected to the pump element 707. The elongated operable element 708 of the pump unit 706 is slidably receivable in the longitudinal guide hole 802 of the introducer unit 702 to move the pump element 707. As illustrated in FIGS. 8A-B, the elongated operable element 708 is slidably received in the longitudinal guide hole 802, and the relative slidable movement between the elongated operable element 708 and the introducer unit 702 is represented by a double-headed arrow.

The longitudinal guide hole 802 extends at least partially between a proximal end portion 804 (which is where the introducer unit 702 contacts to the pump element 707 when assembled together) and a distal end portion 806 of the introducer unit 702 (which corresponds to the distal end portion 808 of the implantable medical device 700). The longitudinal guide hole 802 has a proximal opening 810 positioned at the proximal end portion 804 of the introducer unit 702 and a distal opening 812 positioned at the distal end portion 806 of the introducer unit 702. The positioning of the distal opening 812 relative to the introducer unit 702 enables the elongated operable element 708 to freely slidably move inside the longitudinal guide hole 802 and inside a lumen of body conduit(s) without possibly damaging or injuring the lumen wall adjacent to the distal end portion 806 of the introducer unit 702.

Received in the longitudinal guide hole 802, the elongated operable element 708 extends at least partially along the introducer unit 702 and projects its proximal end portion 814 proximally outwardly from the proximal opening 810 (e.g., when the implantable medical device 700 is in unassembled as illustrated) and its distal end portion 816 distally outwardly from the distal opening 812. The proximal opening 810 of the longitudinal guide hole 802 may include an optional sealing element 824 that provides a fluid-tight engagement between the proximal opening 810 of the introducer unit 702 and the elongated operable element 708, preventing fluid, such as blood, from entering and contaminating the longitudinal guide hole 802. When present, fluid like blood may cause the elongated operable element 708 to malfunction and thus may affect the sliding thereof responsible for assembling and unassembling the implantable medical device 700.

Connected to the proximal end portion 814 of the elongated operable element 708, the pump element 707 is positioned on the proximal end portion 804 of the introducer unit 702 when the elongated operable element 708 is received in the longitudinal guide hole 802.

Referring to FIGS. 8A-C, in use, the relative sliding movement between the elongated operable element 708 of the pump unit 706 and the introducer unit 702 moves the pump element 707 closer to or away from the proximal end portion 804 of the introducer unit 702. Particularly, a pulling force applied to the distal end portion 816 of the elongated operable element 708 moves the pump element 707 closer to the proximal end portion 804 of the introducer unit 702. A pushing force applied to the distal end portion 816 of the elongated operable element 708 moves the pump element 707 away from the proximal end portion 804 of the introducer unit 702. Alternatively or additionally, a pushing force may be applied to the distal end portion 806 of the introducer unit 702 to move the proximal end portion 804 of the introducer unit 702 closer to the pump element 707. Still alternatively or additionally, a pulling force may be applied to the distal end portion 806 of the introducer unit 702 to move the proximal end portion 804 of the introducer unit 702 away from the pump element 707. Although not illustrated as such in FIGS. 8A-C for the sake of clarity, it will be appreciated that the relative slidable movement between the elongated operable element 708 and the introducer unit 702 to correspondingly move the pump element 707 may of course take place in a lumen of body conduit(s), for example by an operator manipulating the distal end portion 816 of the elongated operable element 708.

The relative slidable movement between the elongated operable element 708 and the introducer unit 702 to move the pump element 707 causes the implantable medical device 700 to arrange or rearrange between an unassembled configuration (illustrated in FIGS. 8A-B; also referred herein to as an "un-immobilized configuration" and an "undocked configuration") and an assembled configuration (illustrated in FIG. 8C; also referred herein to as an "immobilized configuration" and a "docked configuration"). Typically, a sheath is used to deliver the implantable medical device 700 in the unassembled configuration at an intraluminal implantation site in a lumen of body conduit(s) for implantation purpose, and to retrieve the implantable medical device 700 in the unassembled configuration from an intraluminal implantation site in a lumen of body conduit(s) for explanation purpose. The implantable medical device 700 may be implanted at the intraluminal implantation site in the assembled configuration or in the unassembled configuration, and may be operated in either the assembled configuration or the unassembled configuration to produce a hemodynamic effect.

In the unassembled configuration, as illustrated in FIG. 8A-B, the introducer unit 702 and the pump element 707 are slid away relative to each other such as to be physically separated by a portion of the elongated operable element 708 therebetween. Particularly, the pump element 707 may be positioned away and spaced apart from the proximal end portion 804 of the introducer unit 702, with the proximal end portion 814 of the elongated operable element 708 being disposed at least partially between the pump element 707 and the proximal end portion 804 of the introducer unit 702.

Figure 9A:
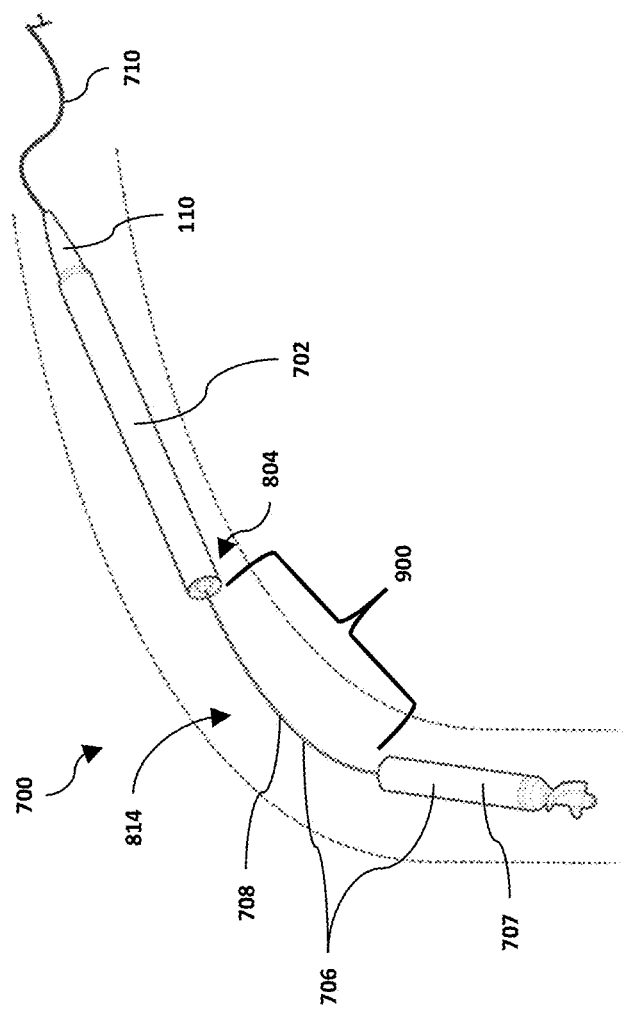
FIGS. 9A and 9B are perspective views of the implantable medical device of FIG. 7 being navigated in a lumen of body conduit.

Advantageously, as illustrated in FIG. 9A, the proximal end portion 814 of the elongated operable element 708 that is disposed at least partially between the proximal end portion 804 of the introducer unit 702 and the pump element 707 may have a intermediate portion 900 thereof that serves as a hinge between the pump element 707 and the introducer unit 702. Particularly, as illustrated in FIG. 9A, when the implantable medical device 700 in the unassembled configuration is passed along an acute lumen angle or a tortuous lumen segment of a body conduit (shown in dash lines in FIG. 9A), the intermediate portion 900 hinges so as the introducer unit 702 and the pump element 707 hinge relative to each other and are separately able to pass therethrough. As illustrated, the elongated operable element 708 is retained in a distal cavity 402 (not shown) that is covered by the tip 110. When the implantable medical device 100 is moved along the body conduit, such as by pulling on the guidewire, the retained elongated operable element 708 carries the pump element 707.

Figure 9B:
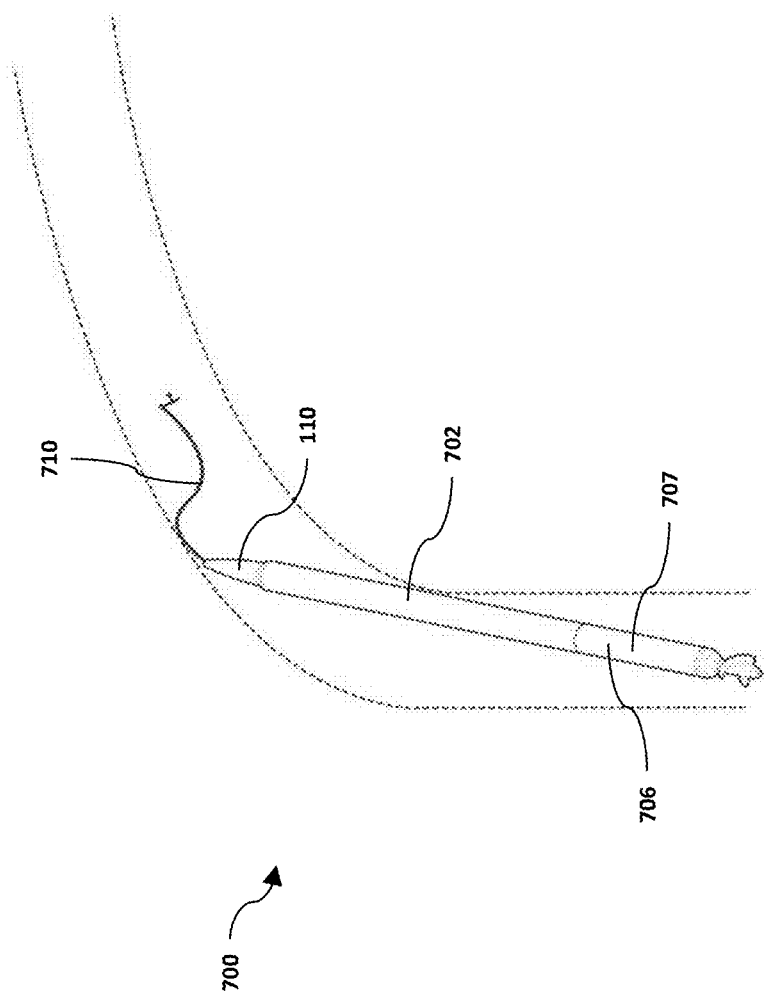

By way of comparison, as illustrated in FIG. 9B, the implantable medical device 700 in the assembled configuration may be too lengthy to be able to pass the acute lumen angle or a tortuous lumen segment of a body conduit (shown in dash lines in FIG. 9B). In other words, in the embodiments exemplified in FIGS. 9A-B, the implantable medical device 700 in the unassembled configuration is able to pass through the acute lumen angle or a tortuous lumen segment of a body conduit (i.e., as illustrated in FIG. 9A), whereas the implantable medical device 700 in the assembled configuration is unable to pass at the same place due to its overall longer length (i.e., as illustrated in FIG. 9B). Such limitation in terms of intraluminal navigation may also be encountered by implantable medical devices known in the art that are too lengthy and/or not assemblable and/or unassemblable. Hence, in the unassembled configuration, the overall length of the implantable medical device 700 is split into smaller length fractions corresponding to the respective individual lengths of the introducer unit 702 and the pump element 707 to enable introduction and/or navigation of the implantable medical device 700 through acute lumen angle or a tortuous lumen segment of body conduit(s).

In the assembled configuration, referring back to FIG. 8C, the introducer unit 702 and the pump element 707 may contact and/or engage each other so as not to be necessarily separated by a portion of the elongated operable element 708 therebetween. Particularly, the pump element 707 may be positioned close enough to contact and/or engage the proximal end portion 804 of the introducer unit 702, while the distal end portion 816 of the elongated operable element 708 is disposed on the distal end portion 806 of the introducer unit 702. The introducer unit 702 and the pump element 707 may removably assemble together (i.e., the introducer unit 702 and the pump element 707 may be assembled and unassembled) or may be non-removably assembled together (i.e., when assembled together, the introducer unit 702 and the pump element 707 cannot be unassembled from each other) in various ways, as described hereinafter.

Although the proximal end portion 804 and the distal end portion 806 of the introducer unit 702 may be of any shape, the distal end portion 806 may be shaped to facilitate introduction of the implantable medical device 702 through an intraluminal access, such as a percutaneous intraluminal access, of a body conduit and to mitigate or prevent damage or injury to the lumen walls. As illustrated in FIGS. 8A-C, for example, the distal end portion 806 of the introducer unit 702 is tapered.

The distal end portion 806 of the introducer unit 702 being generally similar to the distal end portion 204 of the introducer unit 102, notably with respect to the tapered shape and bulge(s) thereof, the distal end portion 806 of the introducer unit 702 will not be further described herein for the sake of brevity. It will therefore be appreciated that a similar description applies to the distal end portion 806 of the introducer unit 702 and the distal end portion 204 of the introducer unit 102, with the necessary change(s), appreciable to the skilled addressee, having been made, if applicable.

For its part, the proximal end portion 804 of the introducer unit 702 may be configured to contact and/or engage the pump unit 706, including the pump element 707 and/or the proximal end portion 814 of the elongated operable element 708, for assembling the pump element 707 to the proximal end portion 804 of the introducer unit 702. Particularly, as illustrated in FIG. 8B, the implantable medical device 700 may be provided with an optional first connector 818 configured to removably or non-removably connect the pump element 707 and the introducer unit 702 together. The implantable medical device 700 may also be provided with an optional second connector 820 configured to removably or non-removably connect the elongated operable element 708 and the introducer unit 702 together. The connectors 818, 820 may be implemented as an interference fit, a latch-type connector, and the like. In absence of the first and second connectors 826, 828, the simple action of bringing the pump element 707 in close proximity to the proximal end portion 804 of the introducer unit 702 to eventually abut to the proximal end portion 804 may be sufficient for assembling or immobilizing the pump element 707 and the introducer unit 702 together.

As illustrated in FIG. 8C, the elongated operable element 708 may be provided with an indicator 830, such as visual marker. The indicator 822 is only visible when the elongated operable element 708 is appropriately pulled though the introducer unit 702 for indicating to a user that the pump unit 706 and the introducer unit 702 are appropriately assembled together.

FIGS. 8A-C further illustrate the implantable medical device 700 provided with an optional securing mechanism 824 configured to secure the elongated operable element 708 in place to the introducer unit 702, according to embodiments. As illustrated, the securing mechanism 824 is integrated to the distal end portion 806 of the introducer unit 702; alternatively, the securing mechanism 824 may be integrated anywhere along the length of the introducer unit 702.

As illustrated in FIGS. 8A-B, the securing mechanism 824 is in an unsecured configuration and thus does not secure the elongated operable element 708, such that the elongated operable element 708 can slide freely in the longitudinal guide hole 802 to move the pump element 707 relative to the introducer unit 702—the implantable medical device 700 can arrange between the unassembled configuration and the assembled configuration. As illustrated in FIG. 8C, the securing mechanism 824 is in a secured configuration and thus secures the elongated operable element 708, such that the elongated operable element 708 cannot slide in the longitudinal guide hole 802 and thus the pump element 707 is maintained assembled or immobilized to the introducer unit 702—the implantable medical device 700 cannot arrange between the unassembled configuration and the assembled configuration. The securing mechanism 824 may adjusted in the unsecured configuration and the secured configuration when the implantable medical device 100 is in the unassembled configuration and the assembled configuration.

The securing mechanism 824 may include a mechanism provided to the introducer unit 702 that frictionally engages at least a portion of the elongated operable element 708 to secure it. In this case, the securing mechanism 824 may be a pressure element, as illustrated in FIGS. 8A-C. Alternatively, the securing mechanism 824 may include a first portion provided to the introducer unit 702 and a second portion provided to the elongated operable element 708. The first and second portions are configured to selectively engage each other to secure them together. In this case, the first portion may be a pin and other similar engagement structures, while the second portion may be a notch, a groove and other similar engagement structures configured to cooperatively engage the first portion.

Still referring to FIGS. 8A-C, in the second aspect of the present disclosure, the elongated operable element 708 may be used not only to move the pump element 707, but also to operate the pump 70, according to embodiments. For example, as illustrated in FIG. 8B, the elongated operable element 708 includes an electrical conductor (also referred herein to as "elongated electrical element"), and may thus be an electrical cable or an electrical wire, that is configured to transmit electricity from a controller 226 (shown In dash lines as an optional component of the implantable medical device 700) to the pump element 707, according to embodiments. Particularly, the proximal end portion 814 of the elongated operable element 708 is operatively connected to the pump element 707, while the distal end portion 816 of the elongated operable element 708 is removably operatively connectable to the controller 226 by a connector 832 (also referred herein to as an "electrical connector").

The connector 832 may be configured to be receivable in the longitudinal guide hole 802 such that the elongated operable element 708 may be completely slid in and out of the longitudinal guide hole 802. Alternatively, the connector 832 may be configured to abut the distal opening 812 of the longitudinal guide hole 802 of the introducer unit 702 to prevent the distal end portion 816 of the elongated operable element 708 from being completely moved inside the longitudinal guide hole 802. Still alternatively, the distal end portion 816 of the elongated operable element 708 may have an optional stop element 834 sized and shaped to abut the distal opening 812 of the longitudinal guide hole 802 of the introducer unit 702 to prevent the distal end portion 816 of the elongated operable element 708 from being completely moved inside the longitudinal guide hole 802. The stop element 834 may be disposed anywhere along the elongated operate element 708.

Alternatively, the elongated operable element 708 may be a driving shaft (not shown) configured to transmit torque from a controller, such as an actuator or a motor, to the pump element 707. In this case, the driving shaft may operate the pump element 707 or any other functional unit 705 in various ways, including by a rotary movement and/or a reciprocating movement.

Still alternatively, the implantable medical device 100 may be provided with a wireless module 836 integrated to the introducer unit 702, inside the body 800 thereof. The wireless module 836 may be operatively connected to the elongated operable element 708, which in this case may include an electrical conductor. The wireless module 836 may be operatively connected to the pump element 707 directly and, in this case, the elongated operable element 708 is not necessarily required to be configured to operate the pump element 707, such as by including an electrical conductor, as described in before. In each case, the wireless module 836 is configured to wirelessly connect to a wireless controller (not shown) to operate the pump element 707.

To enable or facilitate intraluminal navigation, the introducer unit 702 and the elongated operable element 708, such as in the case of the elongated electrical element, may be made a bendable, flexible, and/or resilient material so as to accommodate or conform with various body conduit morphologies, but may still be rigid enough to be pushed through an intraluminal access. For example, the introducer unit 102 may be made of polymer, such as thermoplastic polyurethane, while the elongated operable element 708 may be made of suitable bendable, flexible, and/or resilient material.

As further illustrated in FIG. 8A, the implantable medical device 100 is provided with the optional cover 818, according to embodiments. Depending on the nature of the connector 832, such as when the electrical connector 832 is an electrical connector, it may be desirable to protect the connector 832 from environmental elements, such as a fluid like blood, to ensure proper operation. The cover 818 is removable from the implantable medical device 700 for operatively connecting the connector 832 to the controller 226, as illustrated in FIG. 8B. For example, the cover 818 may be removably attachable to a peripheral cavity where the connector 832 is disposed (as illustrated) or may be removably attachable to the connector 832 directly. The removable attachment of the cover 818 to the implantable medical device 100 may be by interference fit, screwing, and the like.

Figure 10:
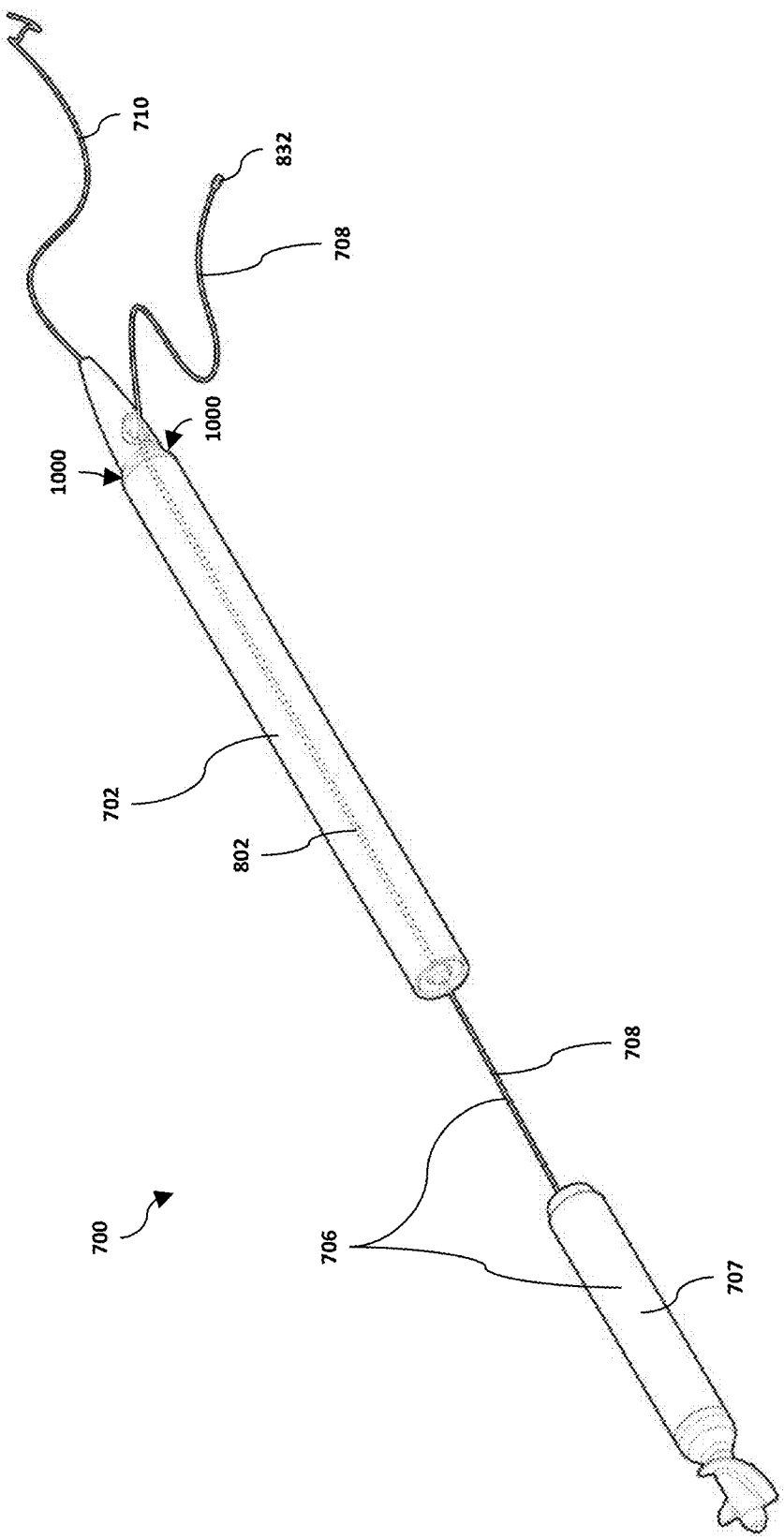
FIG. 10 is a perspective view of the implantable medical device of FIG. 7 provided with a bulge, in accordance with an embodiment.

FIG. 10, as well as FIGS. 9A-B, 11A-B, illustrate the introducer unit 702 provided with an optional bulge 1000, according to embodiments. The cover 818 is omitted from FIG. 10 but may be present.

The bulge 1000 being similar to the bulge 300, the bulge 1000 will not be described herein for the sake of brevity. It will therefore be appreciated that a similar description applies to the bulge 1000 and the bulge 300, with the necessary change(s), appreciable to the skilled addressee, having been made, if applicable.

Figure 11A:
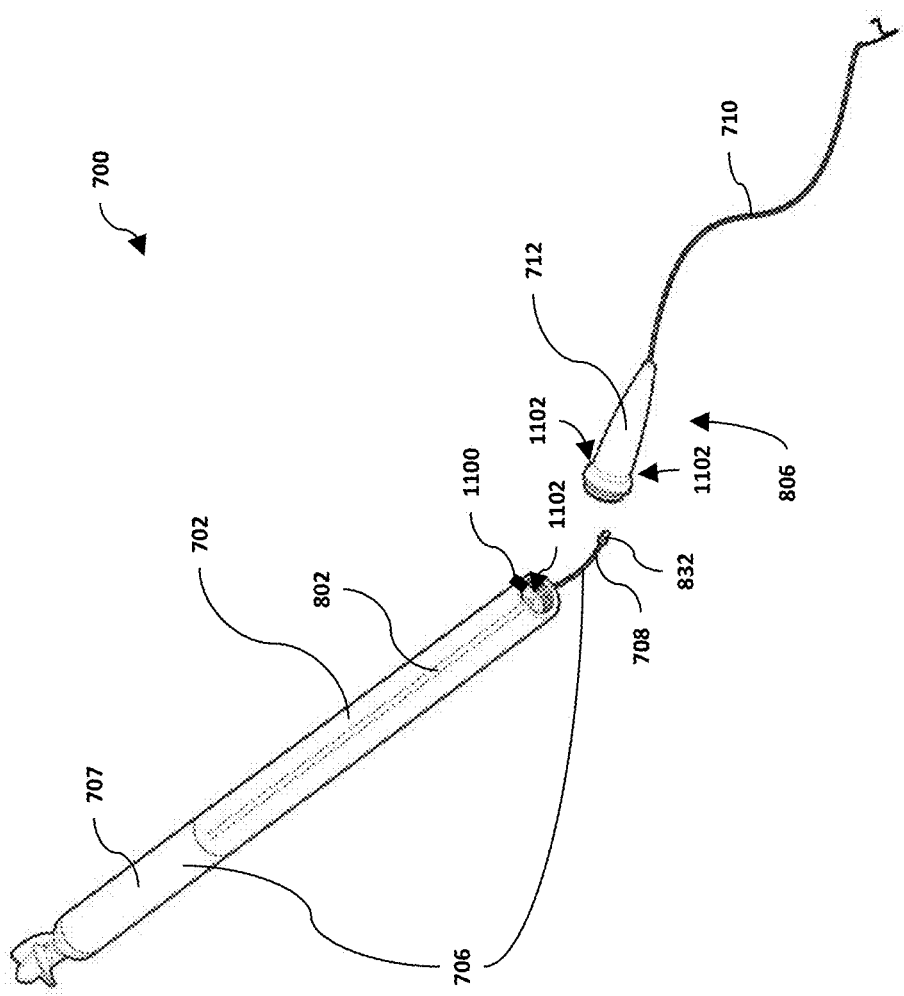
FIGS. 11A-B are a perspective views of the implantable medical of FIG. 7 provided with a tip that is removable, in accordance with an embodiment.
Figure 11B:
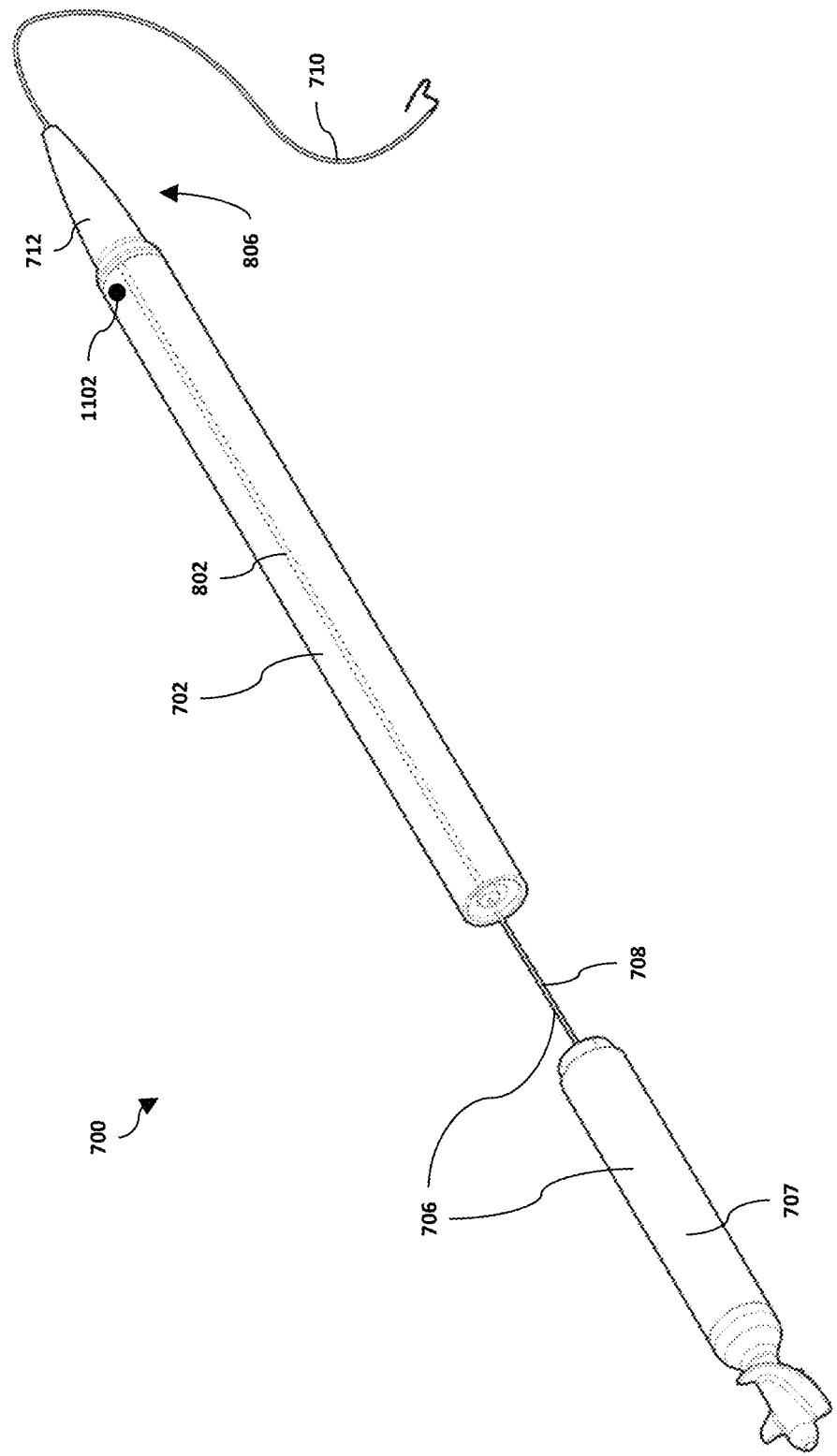

FIGS. 11A-B illustrate the implantable medical device 700 having the distal end portion 806 of the introducer unit 702 provided as the optional tip 712 that is removably attachable to the remainder of the introducer unit 702 and coupled to the guidewire 710, according to embodiments. FIG. 11A illustrates implantable medical device 700 in the assembled configuration with the tip 712 detached from the introducer unit 702. FIG. 11B illustrates implantable medical device 700 in the unassembled configuration with the tip 712 attached to the introducer unit 702. Further illustrated is an optional locking mechanism 1100 for locking the tip 712 to the introducer unit 702.

As illustrated, the tip 712 is removably attachable to a distal cavity 1102 where the elongated operable element 708 projects outwardly therefrom. The elongated operable element 708 is slidable relative to the cavity 1104, such that the connector 832 is itself movable in and out the cavity 1102.

As illustrated, the tip 712 also has an optional bulge 1102 that is similar to the bulges 300 and 1000.

The tip 712 being generally similar to the distal end portion 806 of the introducer unit 702, notably regarding the tapered shape and bulge(s) thereof, the tip 712 will not be further described herein for the sake of brevity. It will therefore be appreciated that a similar description applies to the tip 712 and the distal end portion 806 of the introducer unit 702, with the necessary change(s), appreciable to the skilled addressee, having been made, if applicable.

FIGS. 12A-D illustrate the implantable medical device 700 provided with the optional anchor 714 having a contracted configuration (FIGS. 12A,C) and an expanded configuration (FIGS. 12B,D), according to embodiments. The cover 818 is omitted from FIG. 12A-D but may be present. Although the implantable medical device 700 of FIG. 12A-D may be provided with the cover 818, the implantable medical device 100 may alternatively be provided with the tip 712.

Figure 12A:
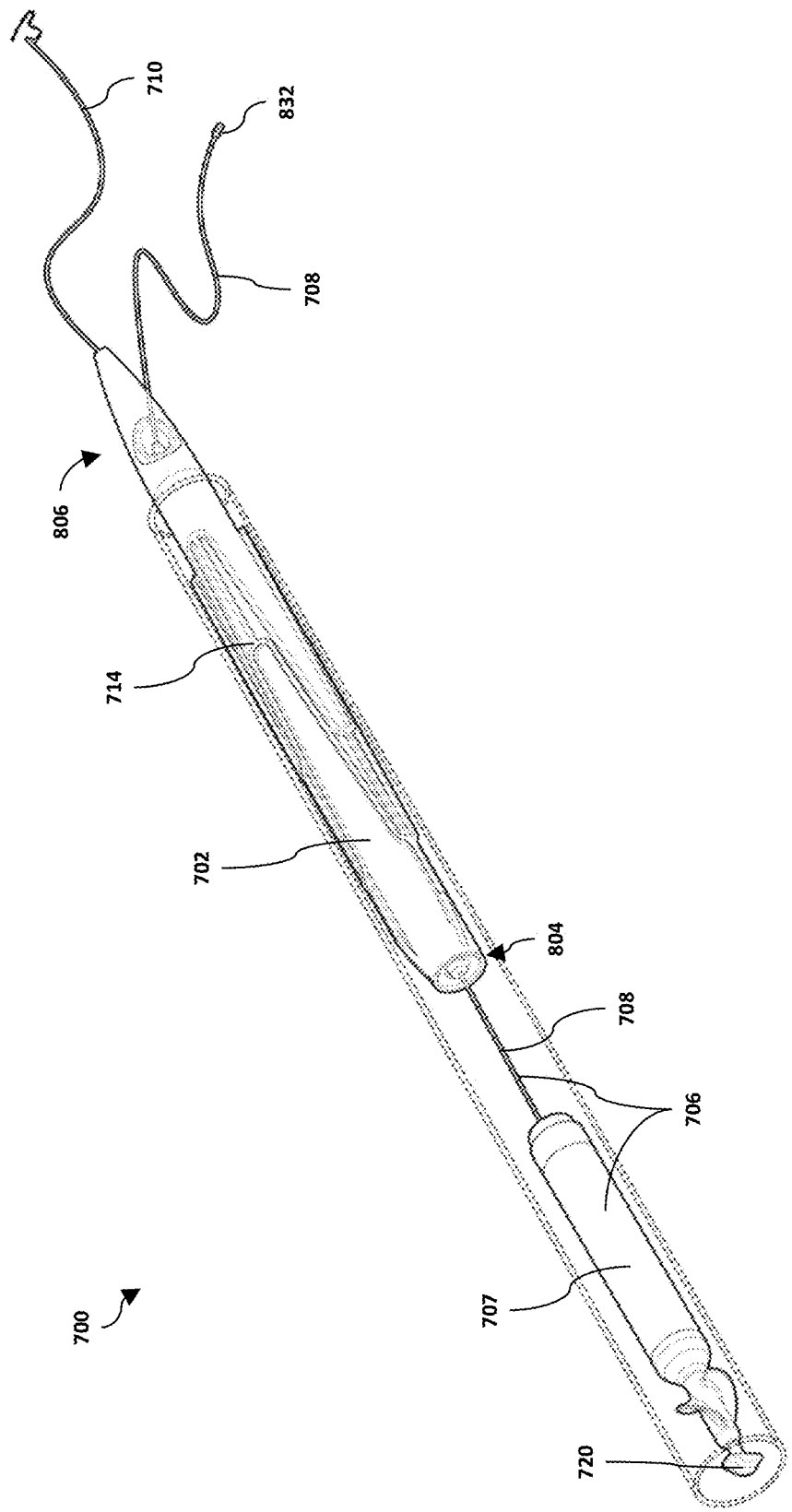
FIGS. 12A-D are a perspective views of the implantable medical of FIG. 7 provided with an anchor, in accordance with an embodiment.
Figure 12B:
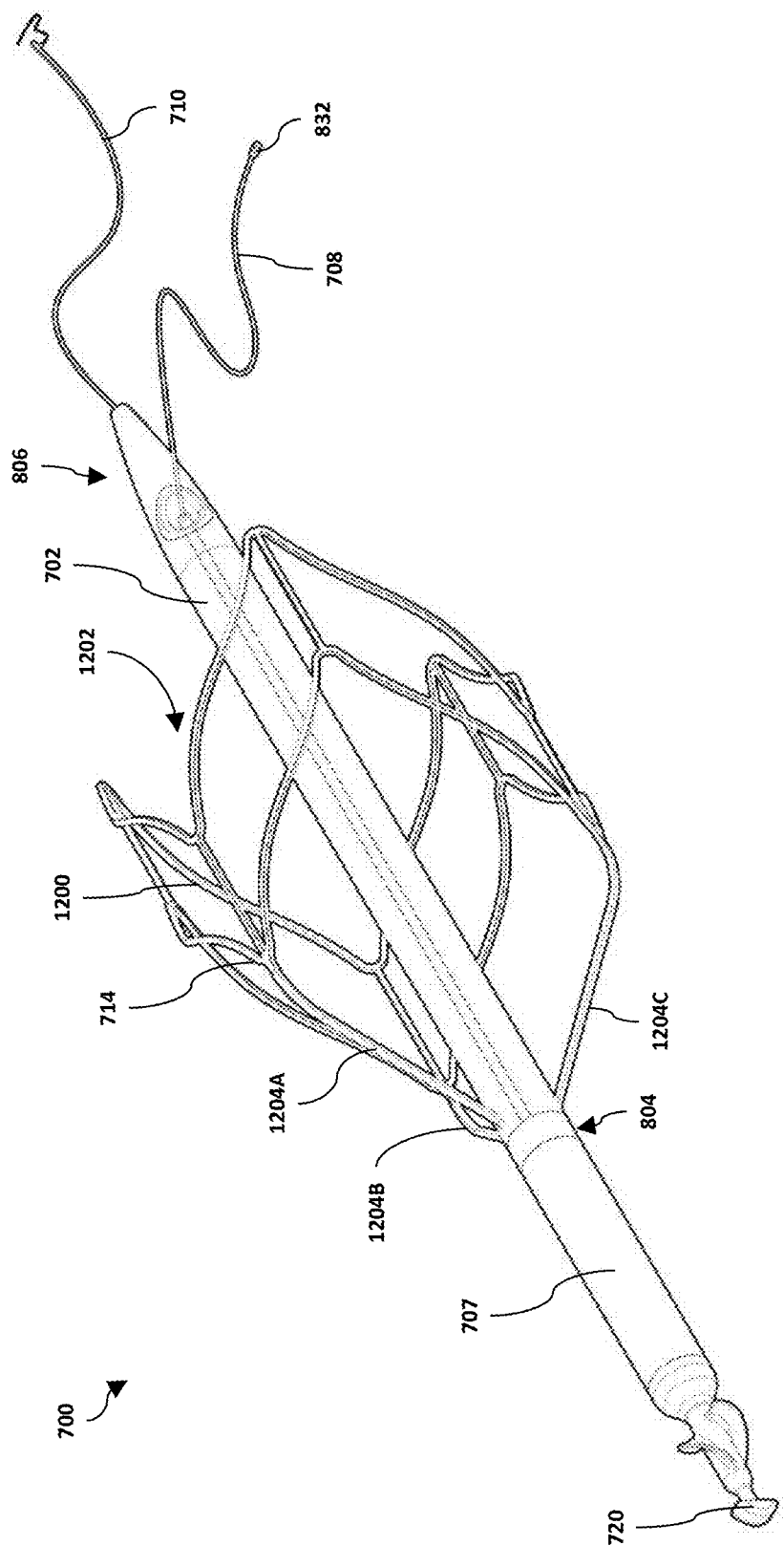

As illustrated in FIGS. 12A-B, the anchor 714 has a tubular wall 1200 that defines a central opening 1202 and includes at least one anchor arm, three anchor arms 1204A-C as illustrated, that converge to and link the tubular wall 1200 to the introducer unit 702, positioning the introducer unit 702 at least partially within the central opening 1202. In use, the relative sliding movement between the elongated operable element 708 of the pump unit 706 and the introducer unit 702 moves the pump element 707 closer to or away from the proximal end portion 804 of the introducer unit 702, such that the pump element 707 may be assembled to and unassembled from the introducer unit 702, outside of central opening 1202, while the anchor 714 is in any of the contracted position and the expanded position.

Figure 12C:
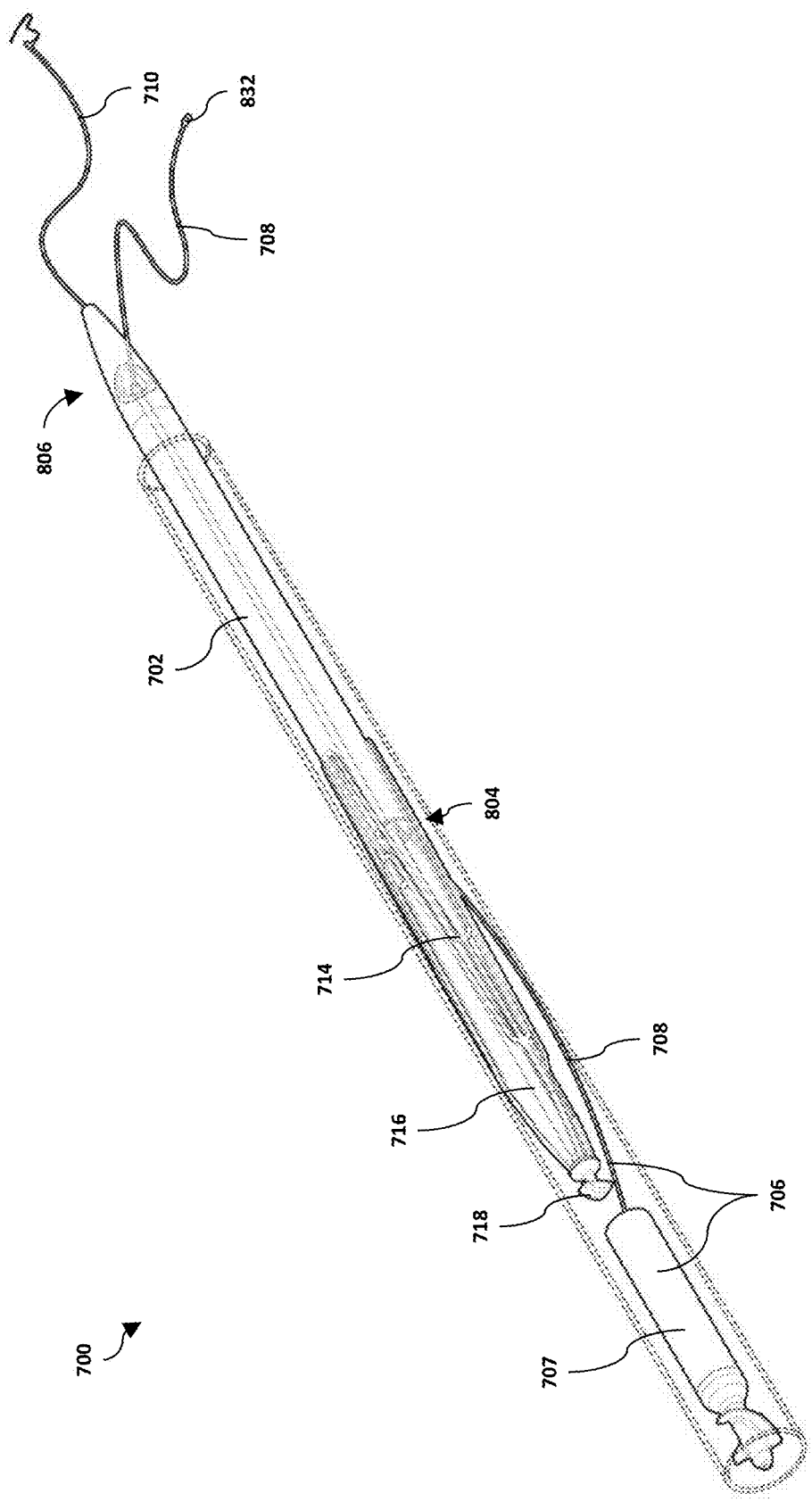
Figure 12D:
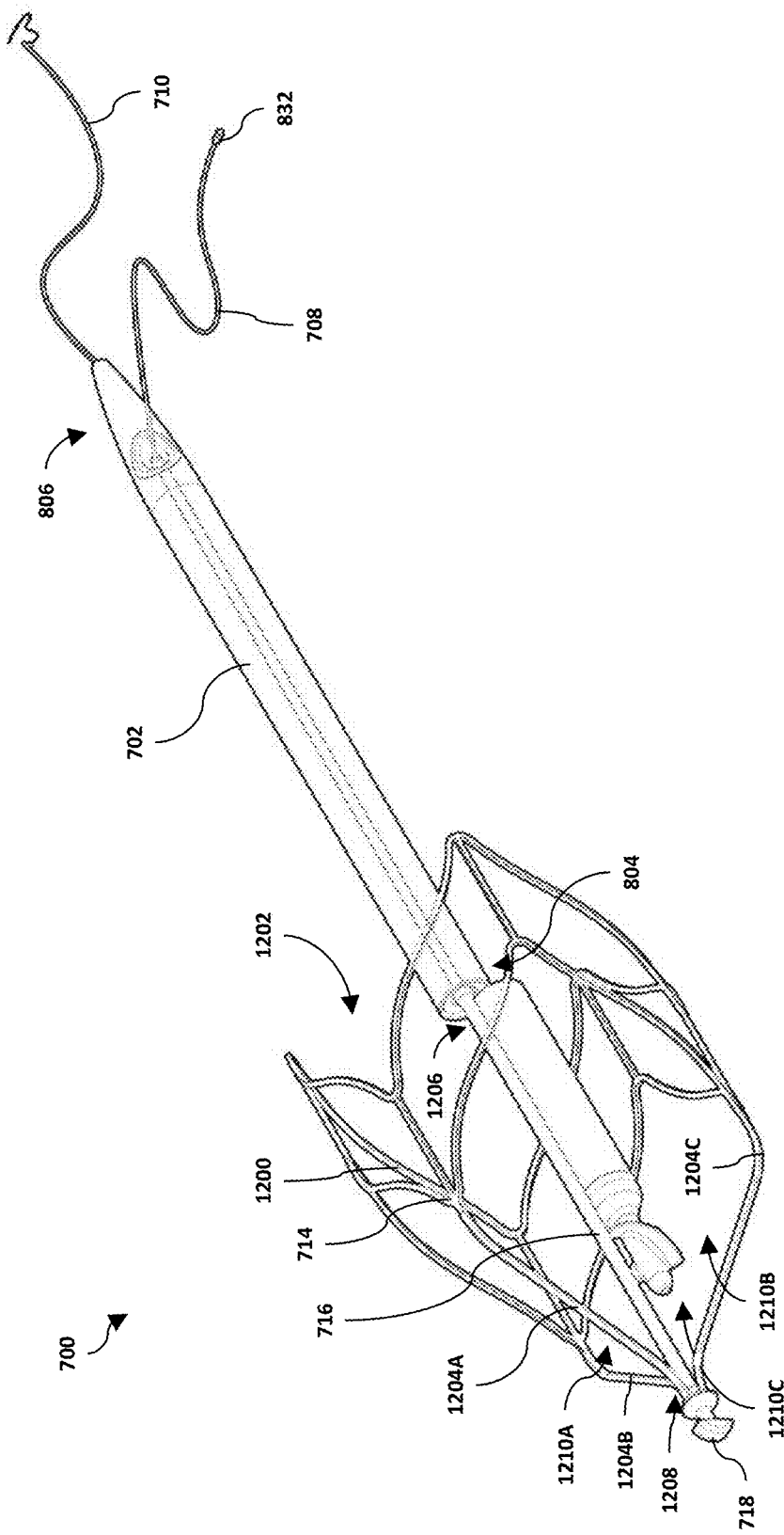

As illustrated in FIGS. 12C-D, the implantable medical device 700 is provided with an optional anchor rod 716 supporting the anchor 714, according to embodiments. The distal end portion 1206 of the anchor rod 716 is attached to the proximal end portion 804 of the introducer unit 702, while the proximal end portion 1208 of the anchor rod 716 is attached to at least one anchor arm, three anchor arms 1204A-C as illustrated. The anchor arms 1204A-C converge to and link the tubular wall 1200 to the anchor rod 716, positioning the anchor rod 716 at least partially within the central opening 1202.

As best illustrated in FIG. 12D, the anchor arms 1204A-C define corresponding radial openings 1210A-C therebetween. Although not readily apparent from FIGS. 12C-D, the elongated operable element 708 is routed through one of the radial openings 1210A-C, such that the pump element 707 passes therethrough when the elongated operable element 708 is slid relative to the introducer unit 702 to assemble the pump element 707 to and unassembled the pump element 707 from the introducer unit 702. When inside the central opening 1202, such as when assembled to the introducer unit 702, the pump element 707 is disposed about the anchor rod 716, as illustrated in FIG. 12D.

In use, the relative sliding movement between the elongated operable element 708 of the pump unit 706 and the introducer unit 702 moves the pump element 707 closer to or away from the proximal end portion 804 of the introducer unit 702, such that the pump element 707 may be assembled to and unassembled from the introducer unit 702, inside the central opening 1202, while the anchor 714 is in the expanded position. As such, the implantable medical device 700 may be arranged in the assembled configuration only when the anchor 714 is in the expanded configuration, whereas the implantable medical device 700 may be arranged in the unassembled configuration when the anchor 714 is in any of the contracted configuration and the expanded configuration.

The anchor 714 and the anchor rod 716 being generally similar to the anchor 112 and the anchor rod 114, respectively, the anchor 714 and the anchor rod 716 will not be further described herein for the sake of brevity. It will therefore be appreciated that a similar description applies to the anchor 714 and the anchor rod 716 as well as the anchor 112 and the anchor rod 114, respectively, with the necessary change(s), appreciable to the skilled addressee, having been made, if applicable.

FIGS. 12A-D further illustrate the implantable medical device 700 provided with the optional first capture element 718 associated with the introducer unit 702, such as with the anchor rod 716 as illustrated in FIGS. 12C-D, and an optional second capture element 720 associated with the pump unit 706, such as with the anchor rod 716 as illustrated in FIGS. 12A-B, according to embodiments. Either or both of the first and second capture elements 718, 720 may be provided to the implantable medical device 700. For example, the first capture element 718 may be provided to the introducer unit 702, while the second capture element 720 may be simultaneously provided to the pump unit 706. The first and second capture elements 718, 720 may be separately capturable from each other or may be capturable together by a tool in vivo, such as a snare and the like, in order to pull or maintain in place the introducer unit 702 and the pump element 706 in a lumen of body conduit(s).

The first capture element 718 may be captured intraluminally in use by a tool, such as a snare and the like, which may then be pulled to move intraluminally the implantable medical device 700 as a whole.

The second capture element 720, when provided to the pump element 707, for example, may be captured intraluminally in use by a tool, such as a snare and the like, which may then be pulled to arrange the implantable medical device 700 from the assembled configuration to the unassembled configuration. The elongated operable element 708 may be pushed simultaneously toward the introducer element 702 to help or assist such configurational arrangement. Depending on its stiffness, however, pushing on the elongated operable element 708 may be sufficient to arrange the implantable medical device 700 from the assembled configuration to the unassembled configuration. In all cases, the configurational arrangement may take place in the presence or absence of the anchor 714 and/or anchor rod 716.

When the securing mechanism 824 is present and secures the elongated operable element 708 in place to the introducer unit 702, maintaining the implantable medical device 700 in the assembled configuration, the implantable medical device 700 as a whole may be moved intraluminally by pulling on a snare capturing and attached to the second capture element 720.

Referring back to FIGS. 7 to 12A-D, the implantable medical device 700 may be provided with an optional guidewire 710, according to embodiments.

The guidewire 710 being generally similar to the guidewire 108, the guidewire 710 will not be further described herein for the sake of brevity. It will therefore be appreciated that a similar description applies to the guidewire 710 and the guidewire 108, with the necessary change(s), appreciable to the skilled addressee, having been made, if applicable.

Figure 13A:
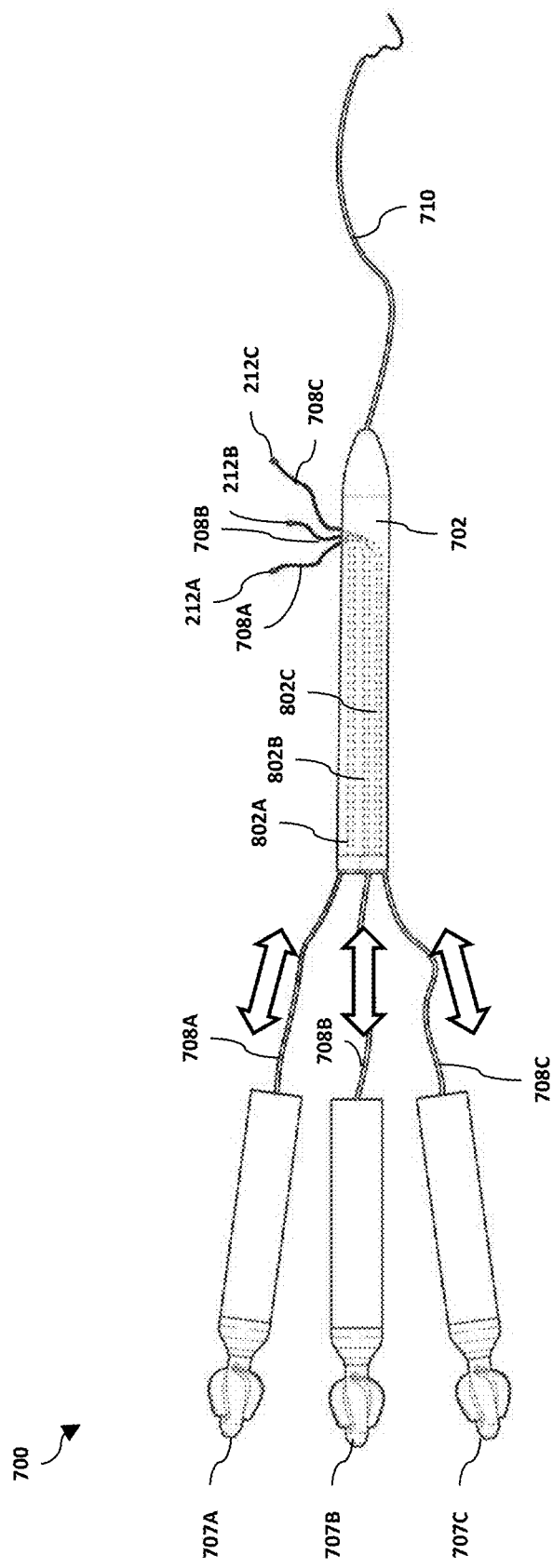
FIG. 13A-B is a perspective view of the implantable medical device of FIG. 7 provided with a plurality of slidable pump elements, in accordance with an embodiment.

FIG. 13A illustrates the implantable medical device 700 that includes an optional plurality of pump units 706, three pump units 706 as illustrated, provided as functional units 705, according to embodiments. Each pump units 706 has a respective one of pump elements 707A-C, provided as functional elements 704, and a respective one of elongated operable elements 708A-C operatively connected to corresponding pump elements 707A-C and operatively connectable to at least one controller, by a respective one of connectors 212A-C. The introducer unit 702 defines a corresponding optional plurality of longitudinal guide holes, three longitudinal guide holes 802A-C as illustrated (shown in dash lines as a way to see through the introducer unit 702), each slidably receiving a respective one of the elongated operable elements 708A-C therein. Alternatively, the introducer unit 702 may be provided with a single longitudinal guide hole 802 for slidably receiving all the elongated operable elements 708A-C therein.

As illustrated in FIG. 13A, each one of the elongated operable element 708A-C is slidably received in a respective one of the longitudinal guide holes 802A-C, and the relative slidable movement between the elongated operable elements 708A-C and the introducer unit 702 is represented by a double-headed arrow. The relative slidable movement between the elongated operable elements 708A-C and the introducer unit 702 to move the pump elements 707A-C causes the implantable medical device 700 to arrange or rearrange between an unassembled configuration where all the pump elements 707A-C are unassembled to the introducer unit 702 (also referred herein to as an "un-immobilized configuration" and an "undocked configuration"), an assembled configuration where all the pump elements 707A-C are assembled to the introducer unit 702 (also referred herein to as an "immobilized configuration" and a "docked configuration"), a partially unassembled configuration where one or two of the pump elements 707A-C are unassembled to the introducer unit 702 ("also referred herein to as a "partially un-immobilized configuration" and a "partially undocked configuration"), and a partially assembled configuration where one or two of the pump elements 707A-C are assembled to the introducer unit 702 ("also referred herein to as a "partially immobilized configuration" and a "partially docked configuration"). It will readily appreciate that the assembled, unassembled, partially unassembled, and partially assembled configurations are possible for any number of pumps 707 without departing from the scope of the present disclosure.

To arrange or rearrange between configurations, each one of the elongated operable elements 708A-C may be slid at a different time (e.g., one at a time) or all at a same time relative (i.e., simultaneously) to the introducer unit 702 to correspondingly move each one of the respective pump elements 707A-C at a different time or all at a same time.

Figure 13B:
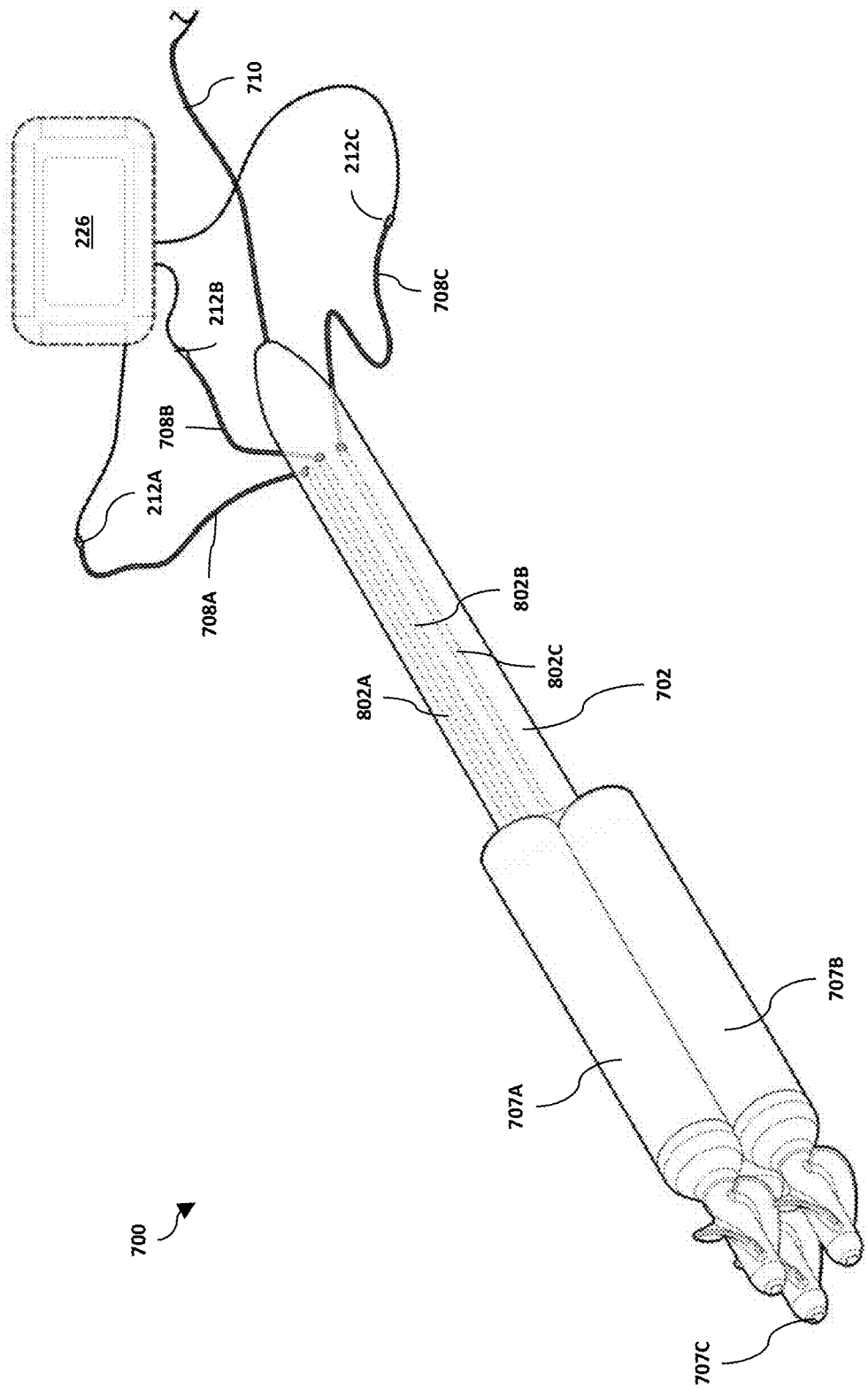

In the unassembled configuration, the introducer unit 702 and the pump elements 707A-C are slid away relative to each other such as to be physically separated by portions of the elongated operable elements 708A-C therebetween. In the unassembled configuration, as illustrated in FIG. 13B with the pump elements 707A-C contained in a sheath (shown In dash lines as an optional component of the implantable medical device 700), the pump elements 707A-C are longitudinally arranged one after the other and may or may not be exactly coaxial relative to each other and/or the introducer unit 702 (referred hereinafter to as a "one-after-the-other" arrangement). Such arrangement may also take place without a sheath, such as when the pump elements 707A-C are in a lumen of body conduit(s). As described for and illustrated in FIGS. 9A-B hereinbefore, when the implantable medical device 700 is in the unassembled configuration, a given portion of each one of the elongated operable elements 708A-C may serve as hinge to advantageously enable a respective one of the pump elements 707A-C to pass along an acute lumen angle or a tortuous lumen segment of body conduit(s).

In the assembled configuration, the introducer unit 702 and the pump elements 707A-C may contact and/or engage each other so as not to be necessarily separated by a portion of the elongated operable elements 708A-C therebetween. Particularly, the pump elements 707A-C may be positioned close enough to contact an/or engage the proximal end portion 804 of the introducer unit 702, while the distal end portion 816 of the elongated operable elements 708A-C is disposed on the distal end portion 806 of the introducer unit 702. In the assembled configuration, as illustrated in FIG. 13B, the pump elements 707A-C are transversally arranged next to each other (referred to hereinafter as a "next-to-each-other arrangement"). The pump elements 707A-C may also be longitudinally offset relative to each other for improving the outflow performance and characteristic thereof. The introducer unit 702 and the pump elements 707A-C may removably assemble together (i.e., the introducer unit 702 and the pump elements 707A-C may be assembled and unassembled) or may be non-removably assembled together (i.e., when assembled together, the introducer unit 702 and the pump elements 707A-C cannot be unassembled from each other) in various ways, as described hereinafter.

The proximal end portion 804 of the introducer unit 702 may be configured to contact and/or engage the pump units 706A-C, including the pump elements 707A-C and/or the proximal end portion 814 of the elongated operable elements 708A-C, for assembling the pump elements 707A-C to the proximal end portion 804 of the introducer unit 702. Particularly, the implantable medical device 700 may be provided with an optional plurality of first connectors 818 configured to removably or non-removably connect corresponding pump elements 707A-C and the introducer unit 702 together, as described hereinbefore. The implantable medical device 700 may also be provided with an optional plurality of second connector 820 configured to removably or non-removably connect corresponding elongated operable elements 708A-C and the introducer unit 702 together, as described hereinbefore. Further, in the assembled configuration, the pump units 706A-C may be coupled together via an interaction between (i) at least two of the pump elements 707A-C, (ii) at two of the elongated operable elements 708A-C, and/or (iii) at least one of the pump elements 707A-C and at least one of the elongated operable elements 708A-C.

In the assembled configuration, the pumps 707 A-C may be longitudinally offset relative to each other so that each one of the impeller end portions of the pump elements 707A-C are longitudinally positioned differently. The pumps 707 A-C may also not be arranged parallel relative to each other so that each one of the impeller end portions of the pump elements 707A-C are spaced apart by a greater distance than a distance between each one of the introducer unit contacting end portions of the pump elements 707A-C. Depending of the pump elements 707A-C, such positioning and spacing may improve the pumps' performance, including better fluid outflow and reduced fluid shear stress, which in the latter case may lead to hemolysis and/or thrombogenesis for blood.

As illustrated in FIG. 13B, in the assembled configuration, the pump elements 707A-C collectively have a transverse cross-sectional size, which may be averaged to a transverse cross-sectional size of a circle containing transverse cross-section portions of the pump elements 707A-C therein, that is greater than the transverse cross-sectional size of the introducer unit 702. This may be the case, for example, when each one of the pump elements 707A-C have a transverse cross-sectional size that is substantially the same as the transverse cross-sectional size of the introducer unit 702, as illustrated. Alternatively, the pump elements 707A-C in the assembled configuration may collectively have a transverse cross-sectional size, which is averaged as described before, that is equal or smaller than the transverse cross-sectional size of the introducer unit 702. This may be the case, for example, when each one of the pump elements 707A-C have a transverse cross-sectional size that is substantially smaller than the transverse cross-sectional size of the introducer unit 702.

The implantable medical device 700 of FIGS. 13A-B may also be provided with the optional tip 712 and optional locking mechanism 1100, the optional anchor 714, the optional anchor rod 716, at least one optional first capture elements 718 and/or at least one optional second capture elements 720, the optional guidewire 710, and the optional securing mechanism 824.

When provided, the anchor rod 716 is linked by at least one anchor arm thereof, such as the anchor arms 1204A-C, such that the introducer unit 702 is positioned at least partially within the central opening 1202 and/or each one of the pump elements 707A-C is slidably positionable within the central opening 1202. In this case, each one of the elongated operable elements 708A-C is routed through a respective one of the radial openings 1210A-C defined by the corresponding anchor arms 1204A-C, such that each one of the pump elements 707A-C may pass through a respective one of the radial openings 1210A-C when a corresponding one of the elongated operable elements 708A-C is slid relative to the introducer unit 702 to assemble the pump elements 707A-C to and unassembled the pump elements 707A-C from the introducer unit 702. When inside the central opening 1202, such as when assembled to the introducer unit 702, each one of the pump elements 707A-C is disposed about the anchor rod 716.

When present, the first capture element 718 is provided to the introducer unit 702, such as to the anchor rod 716. When present, the optional second capture element 720 may be provided to each one of the pump units 706A-C, such as to the pump elements 707A-C. Particularly, the second capture element 720 of each pump elements 707A-C may be captured intraluminally in use by a tool, such as a snare and the like, which may then be pulled to move intraluminally the pump elements 707A-C, separately from each other, away from the introducer unit 702 to arrange the implantable medical device 700 between the unassembled configuration, the assembled configuration, the partially unassembled configuration, and the partially assembled configuration.

When present, the securing mechanism 824 may be provided to the introducer unit 702 and/or each one of the elongated operable elements 708A-C. A single securing mechanism 824 may be provided to secure all the elongated operable elements 708A-C. Alternatively, a plurality of securing mechanisms 822 may be provided to secure a respective one of the elongated operable elements 708A-C. In this case, the securing mechanisms 822 may function independently from each other. When the securing mechanism 824 secures one or more of the elongated operable element 708A-C, the implantable medical device 700 as a whole may be moved intraluminally by pulling on a snare capturing and attached to the second capture element(s) 720 corresponding to the elongated operable element(s) 708A-C secured by the securing mechanism 824.

The implantable medical device 700 provided with the plurality of pump units 706 being similar to the implantable medical device 700 provided with a single pumping unit 706, the description of the implantable medical device 700 provided with the plurality of pump units 706 will not be further described herein for the sake of brevity. It will therefore be appreciated that the description of the implantable medical device 700 provided with a single pumping unit 706 applies to the implantable medical device 700 provided with the plurality of pump units 706A-C, with the necessary change(s), appreciable to the skilled addressee, having been made, if applicable.

As illustrated in FIG. 13 C, the implantable medical device 700 may be provided with at least one prolongation wire, three prolongation wires 1300A-C as illustrated, according to embodiments. Each one of the prolongation wires 1300A-C is slidably receivable in a respective one of the longitudinal guide holes 802A-C (or in a single longitudinal guide holes 802 as the case may be), similarly to the elongated operable elements 708A-C, and is removably attachable to a respective one of the elongated operable elements 708A-C, on the distal end portion 816 thereof. The prolongation wires 1300A-C may be slid for arranging the implantable medical device 700 between the unassembled configuration, the assembled configuration, the partially unassembled configuration, and the partially assembled configuration. The implantable medical device 700 provided with a single pumping unit 706 may similarly include a single prolongation wire 1300.

Each one of the prolongation wires 1300A-C may be provided with a respective stop element 834, as described for the elongated operable elements 708A-C. Each one of the prolongation wires 1300A-C may also be provided with a seal element configured to sealingly engage the distal opening 812 of the longitudinal guide holes 802A-C. Since the transverse cross-sectional size of the prolongation wires 1300A-C is smaller than the transverse cross-sectional size of the elongated operable elements 708A-C, a space is present in the longitudinal guide holes 802A-C when the prolongation wires 1300A-C are received therein. Fluid, such as blood, may leak through these spaces.

Figure 14A:
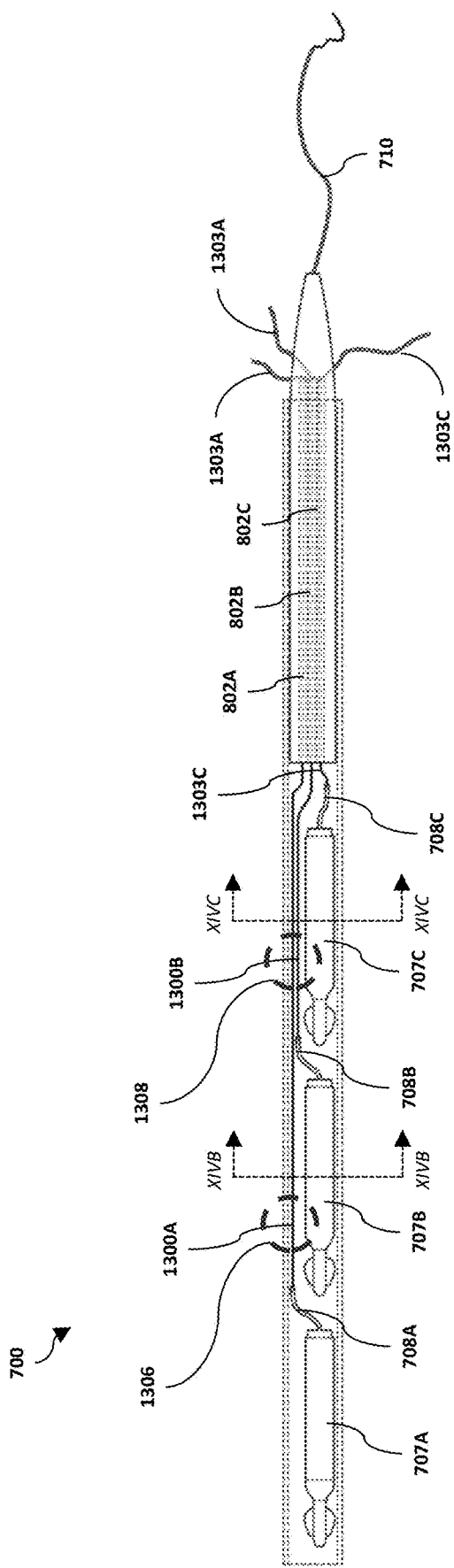
FIG. 14A is a longitudinal cross-section view of the implantable medical device of FIG. 7 contained in a sheath.

As illustrated in FIG. 14A, the implantable medical device 700 in the unassembled configuration is contained in a sheath (shown in dash lines as an optional component of the implantable medical device 700) with the pump elements 707A-C in the one-after-the-other arrangement. Each one of the prolongation wires 1300A-C is slidably received thought the introducer unit 702 and is removably attached to a respective one of the elongated operable elements 708A-C.

Still referring to FIG. 14A and as also illustrated in FIGS. 14B-E, the first prolongation wire 1300A associated with the first pump element 707A passes in a first space 1306 defined between the second pump element 707B and the sheath (or the lumen wall in absence of sheath) (FIGS. 14A, 14B). The first and second prolongation wires 1300A,B associated with the first and second pump elements 707A,B, respectively, both pass in a second space 1308 defined between the third pump element 707C and the sheath (or the lumen wall in absence of sheath) (FIGS. 14A, 14C).

Further, as best illustrated in FIGS. 14B-D, the transverse cross-sectional size of the prolongation wires 1300A,B (and also 1300C) is smaller than the transverse cross-sectional size of the elongated operable elements 708A-B (and 708C). This size difference advantageously enables the implantable medical device 700 equipped with the prolongation wires 1300A-B (and also 1300C as illustrated) running along the pump elements 707B,C to have a smaller transverse cross-sectional size (i.e., $d_1$), as compared to the transverse cross-sectional size (i.e., $d_2$) of the implantable medical device 700 having the elongated operable elements 708A,B running along the pump elements 707B,C (i.e., not equipped with the prolongation wires 1300A-B).

Indeed, the smaller transverse cross-sectional size of the prolongation wires, as compared to the transverse cross-sectional size of the elongated operable elements, advantageously enables using a sheath of relatively smaller diameter (as usually reported in FR unit) for implanting and explanting the implantable medical device 700. Such reduction in sheath size in turn enables the introduction, and navigation of the implantable medical device 700 in lumens of body conduits not necessarily amenable to the use of implantable medical devices.

Notably, the prolongation wires can have a comparatively smaller transverse cross-sectional size than the elongated operable elements because the prolongation wires are not configured to transmit electricity-they do not integrate an electrical conductor in their construction. It will be appreciated that any other ways of reducing the transverse cross-sectional size of an elongated structure capable of attaching the elongated control operable elements have the same advantages.

For comparison purpose with FIG. 14B, FIG. 14D illustrates the first elongated operable element 708A coming from the first pump element 707A that passes in the first space 1306 defined between the second pump element 707B and the sheath (or the lumen wall in absence of sheath). For comparison purpose with FIG. 14C, FIG. 14E illustrates the first and second elongated operable elements 708A-B coming from the first and second pump element 707A-B that pass in the second space 1308 defined between the third pump element 707C and the sheath (or the lumen wall in absence of sheath). As it can be readily observable, the sheath in FIGS. 14D-E needs to have a greater transverse cross-sectional size than the sheath in FIGS. 14B-C in order to accommodate the implantable medical device 700 due to the transverse cross-sectional size difference between the elongated operable elements and the prolongation wires.

Taken together, because they are intraluminally assemblable, the implantable medical devices advantageously have a reduced operating profile for introduction and navigation in a lumen of body conduit(s) while being able to intraluminally expand to a larger operative profile for performing a desired function and/or operation, such as a hemodynamic effect or a synergistic effect. For example, the implantable medical device in the unassembled configuration may have a reduced operating profile substantially corresponding to the one of the introducer unit and the functional unit having the larger transverse cross-sectional. When arranged in the assembled configuration, the implantable medical device may have a larger operating profile substantially corresponding to a transverse cross-sectional size of the introducer unit plus a fraction of the transverse cross-sectional size of the functional unit.

With reference now to FIGS. 15-19, an implantable medical device 1500 will be described, according to embodiments. The implantable medical device 1500 being generally similar to implantable medical device 700, only some features of the implantable medical device 1500 will be described hereinafter for the sake of brevity. It will therefore be appreciated that the description of the implantable medical device 700 applies to the implantable medical device 1500, with the necessary change(s), appreciable to the skilled addressee, having been made, if applicable.

Figure 16:
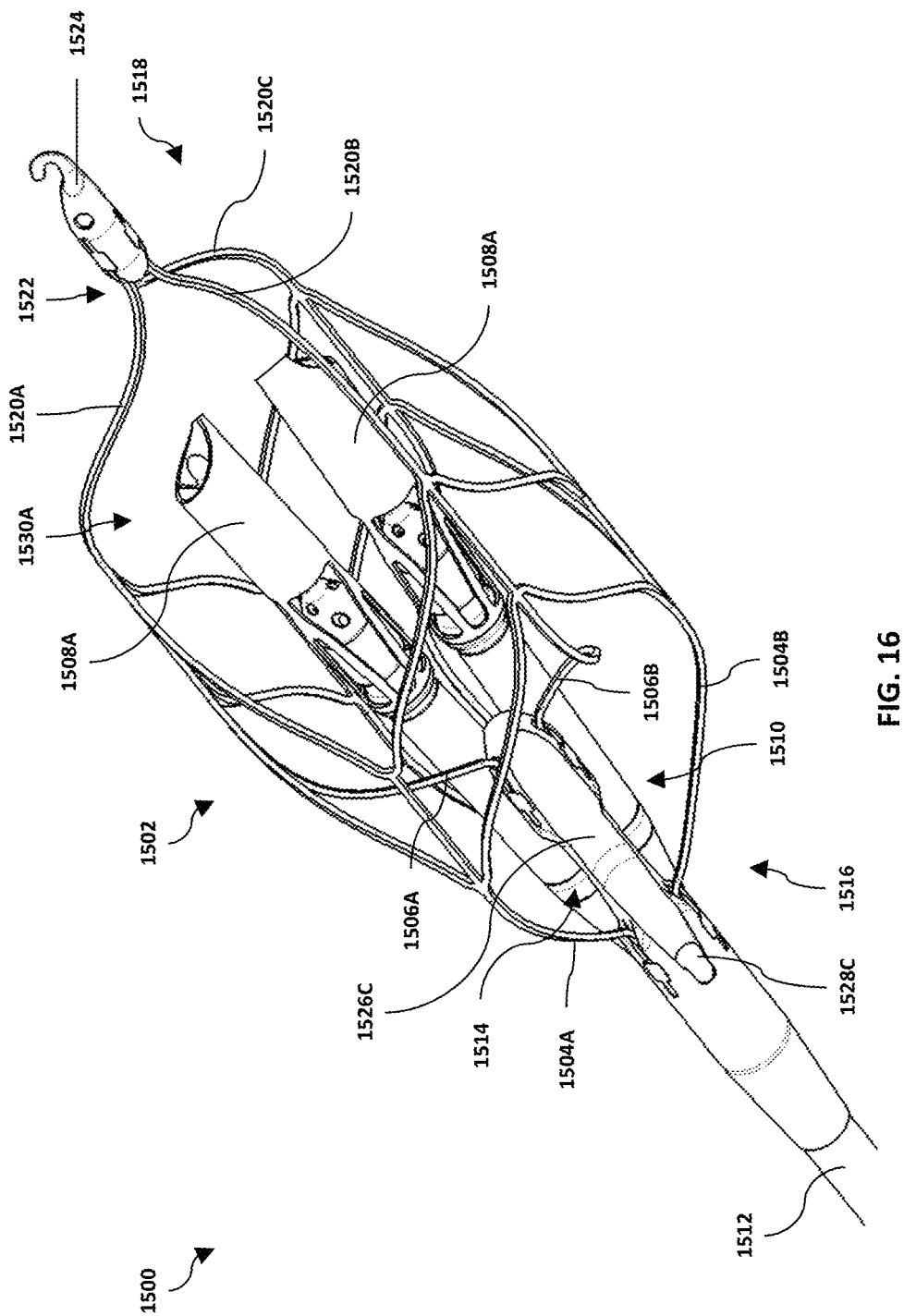
Figure 17:
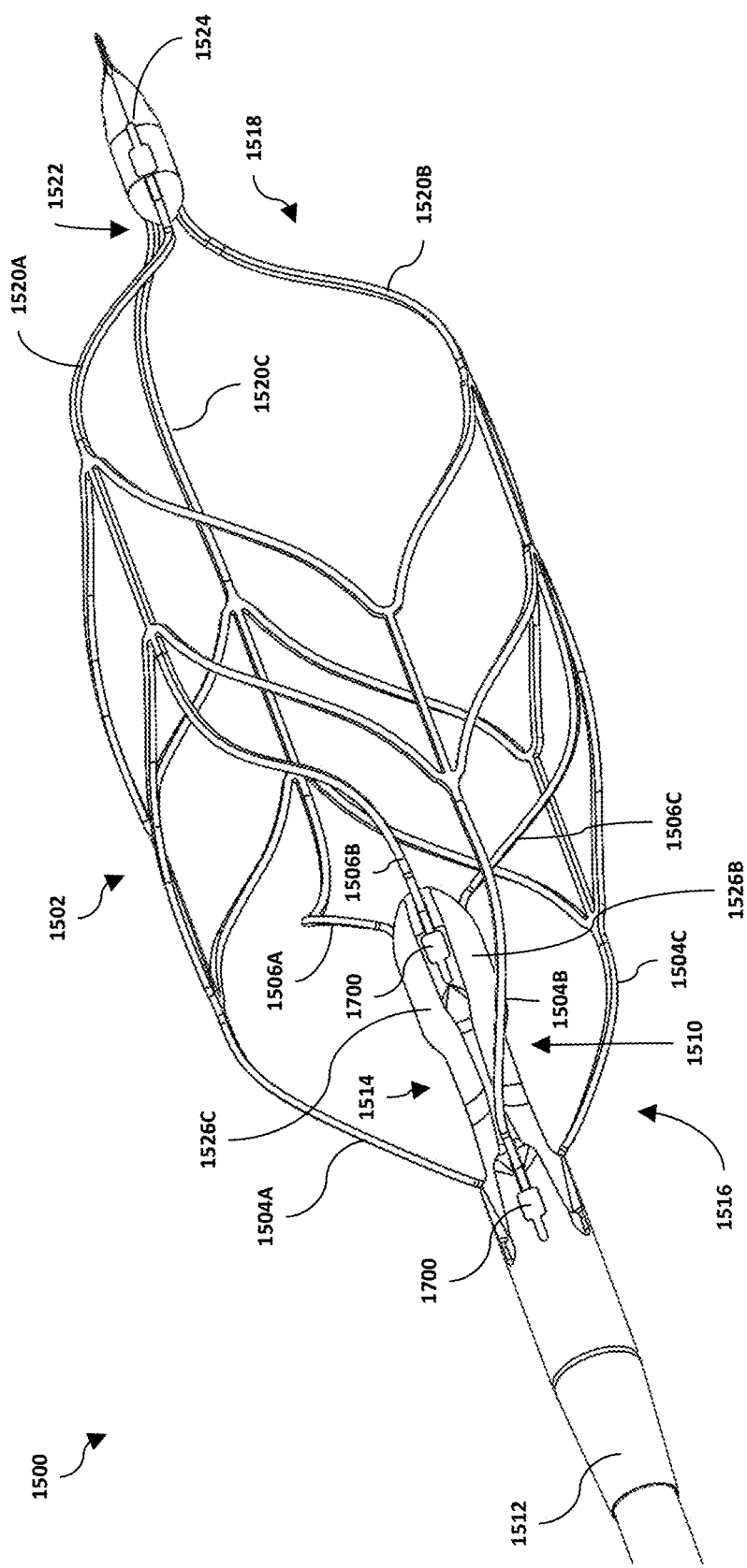
Figure 18:
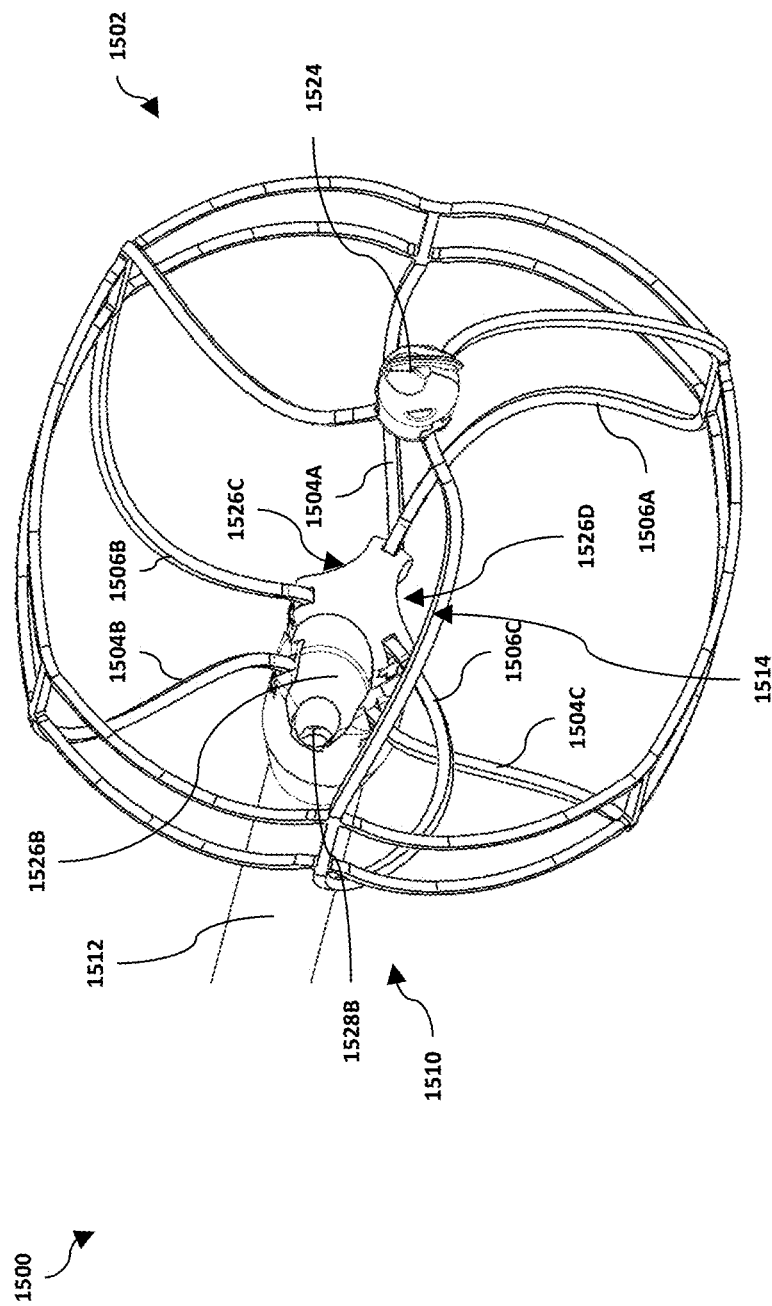
Figure 19:
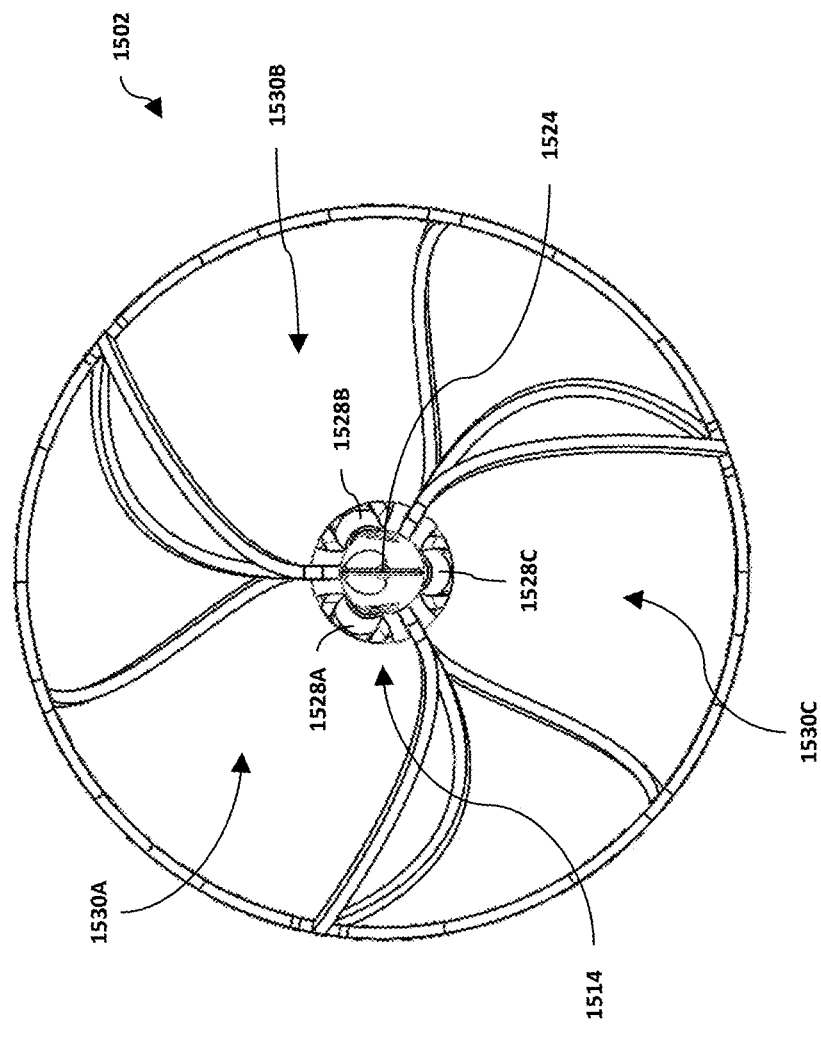

FIGS. 15-19 illustrate the implantable medical device 1500 provided with an optional anchor 1502 having at least one proximal anchor arms, three proximal anchor arms 1504A-C as illustrated, and at least one distal anchor arm, three distal anchor arms 1506A-C as illustrated, according to embodiments. In FIG. 15, the implantable medical device 1500 is provided with the pump units 1508A-B in the assembled configuration, and the pump unit 1508C is in the unassembled configuration; therefore, the implantable medical device 1500 is in the partially unassembled configuration and in the partially assembled configuration. In FIG. 16, the pump units 1508A-B are in the assembled configuration, and the pump unit 1508C is omitted for clarity reason. In FIGS. 17-19, the pump units 1508A-C are omitted for clarity reasons.

As illustrated in FIGS. 15-19, a proximal end portion 1510 of an introducer unit 1512 includes an optional protruding portion 1514 projecting distally therefrom and configured to attach the anchor 1502, according to embodiments. The protruding portion 1514 may be a component coupled to the introducer unit 1512 or may be a component integrally formed with the introducer unit 1512 so as to form a one-piece unit. Particularly, as best illustrated in FIGS. 15-18, each one of the proximal anchor arms 1504A-C links the protruding portion 1514 at a proximal location thereof, while each one of the distal anchor arms 1506A-C links the protruding portion 1514 at a distal location thereof. The proximal and distal anchor arms 1504A-C, 1506A-C may link the anchor 1504 anywhere on the introducer unit 1512.

The longitudinal linking at two spaced apart locations along the protruding portion 1514 advantageously gives anchoring stability to the implantable medical device 1500, either in the unassembled or assembled configuration, when anchored in a lumen of body conduit(s). Indeed, depending on the implantable medical device and the intraluminal implantation site, pivoting of the implantable medical device 1500 is reduced by the proximal and distal anchor arms 1504A-C, 1506A-C, as compared to an implantable medical device linked at a single location thereof to an anchor. In the latter case, the single location linking the anchor may act as a pivot point, such pivot point is reduced, if not illuminated, when two linking location are present. Generally, pivoting movements of intraluminally anchored implantable medical devices are to be avoided since such movements may damage or injury the lumen wall, specially upon contact of a moving part like a pump impeller not encased in a shroud.

With reference to FIG. 17, the linking of the proximal anchor arms 1504A-C and the distal anchor arms 1506A-C to the protruding portion 1514 may be a captive attachment, as illustrated in FIG. 17, according to embodiments. Particularly, each one of the proximal and distal anchor arms 1504A-C, 1506A-C have a respective attaching end portion trapped in a concavity by a cap 1700 capping the concavity. The attaching end portion is sized and shaped not to be removable from the concavity when capped by the cap 1700 and, along with the concavity, is not readily observable in FIG. 17 due to the presence of the cap 1700. Also, only caps 1700 of proximal and distal anchor arms 1504B, 1506B are shown on FIG. 17.

The captive attachment is advantageous when the proximal and distal anchor arms 1504A-C, 1506A-C as well as the protruding portion 1514 are made of one or more materials that are incompatible to be directly attached, secured, or coupled together. This is the case, for example, when the proximal and distal anchor arms 1504A-C, 1506A-C, as well as possibly the anchor 1502, are made of nitinol, while the protruding portion 1514 is made of stainless steel. Other incompatible materials are possible. Nitinol and stainless steel are generally not amenable to a direct attachment, securement, or coupling together, such as by welding, that would satisfy the stringent requirements of at least some implantable medical devices.

The cap may be secured to the protruding portion 1514 by various ways, including but not limited to welding, fusing, gluing, mechanical inter-engagement, and the like. When welded, the cap 1700 is made of a material that is compatible with the material of the protruding portion 1514. For example, both the cap 1700 and the protruding portion 1514 may be made of stainless steel, thereby alleviating the limitation associated with the proximal and distal anchor arms 1504A-C, 1506A-C being made of nitinol and the protruding portion 1514 being made of incompatible stainless steel for the purpose of a direct attachment, securement, or coupling.

The captive attachment of one or more attaching end portions of the proximal and distal anchor arms 1504A-C, 1506A-C is not to be limited to the protruding portion 1514 and may be implemented anywhere on the introducer unit 1512. Further, the implementation of the captive attachment is not to be limited to the interaction between the proximal and distal anchor arms 1504A-C, 1506A-C and the protruding portion 1514. The captive attachment may be implemented to any other component(s) of the implantable medical devices 1500 described herein. In any case, the captive attachment does not necessarily require materials that are incompatible to a direct attachment, securement, or coupling, depending on the manufacturing need, for example.

As illustrated in FIGS. 15-17, the anchor 1502 has a double tapered shape, which may be approximate to an oval, ovaloid or oblong shape, according to embodiments. A tapered proximal end portion 1516 of the anchor 1502 is formed by the linking of the proximal anchor arms 1504A-C that collectively converge toward the protruding portion 1514, while a tapered distal end portion 1518 of the anchor 1502 is formed by at least two distalmost anchor arms, distalmost anchor arms 1520A-C, collectively converging together toward a distalmost converging point 1522. The tapered distal end portion 1518 defined at least one radial opening, three radial openings 1530A-C as illustrated in FIG. 19, through which corresponding pump unit 1508A-C pass therethrough for assembling and unassembling, according to embodiments.

The double tapered shape enables the anchor 1502 to be converted from the expanded configuration to the contracted configuration from the tapered proximal end portion 1516 and the tapered distal end portion 1518 thereof. As described hereinbefore for the conversion of the anchors 112, 714, the introducer unit 1512 may be pulled while being in a sheath to initiate such a conversion from the tapered proximal end portion 1516. A tool, such as a snare, attached to the capture element 1524 (described hereinafter) may be pulled while being in a sheath to initiate such a conversion from the tapered distal end portion 1518.

As illustrated in FIGS. 15-19, an optional capture element 1524, which may correspond to the first capture element 718 of the implantable medical device 700, may be provided at the distalmost converging point 1522. Alternatively, the capture element 1524 may bring the distalmost anchor arms 1520A-C together and be attached thereto. The capture element 1524 may form at least partially the tapered distal end portion 1518 of the anchor 1502. As illustrated, the capture element 1524 is a hook capturable by a tool, such as a snare. Alternatively, the capture element may be a structure capable of being intraluminally captured.

As illustrated in FIGS. 16-18, the protruding portion 1514 is provided with at least one optional receiving surface 1526, three receiving surfaces 1526A-C as illustrated, and/or with at least one optional distal guide hole, three distal guide holes 1528A-C as best shown in FIG. 19, according to embodiments. Particularly, the protruding portion 1514 may be provided with a number of receiving surface(s) 1526 and with a number of distal guide holes 1528 corresponding to the number of pump unit(s) 1508. The protruding portion 1514 may be configured to removably or non-removably assemble and unassemble the pump units 1508A-C to the proximal end portion 1510 of the introducer unit 1512, or to facilitate the removable or non-removable assembling and unassembling of the pump units 1508A-C to the proximal end portion 1510 of an introducer unit 1512.

Each one of the receiving surfaces 1526A-C longitudinally extends at least partially along the protruding portion 1514 and may be equidistantly spaced apart for each other, as illustrated, or not. As such, when assembled the pump units 1508 are disposed about the protruding portion 1514. Also, the receiving surfaces 1526A-C may be concave to increase or improve its contact surface with the pump units 1508A-C when assembled thereto. Each one of the receiving surfaces 1526A-C may be configured to mitigate or prevent blood clotting between them and corresponding pump units 1508A-C when assembled thereto. For example, each one of the receiving surfaces 1526A-C may be sized and shaped to conform with or mate with a respective one of the pump units 1508A-C so as to substantially exclude the presence of blood between them and the corresponding pump units 1508A-C when assembled thereto. Alternatively or additionally, each one of the receiving surfaces 1526A-C may be provided with seal for providing a fluid thigh contact with the corresponding pump units 1508A-C when assembled thereto.

Each one of the receiving surfaces 1526A-C may be associated with a respective one of the distal guide holes 1528A-C, as further illustrated in FIGS. 16-18, or may not be associated with a respective one of the distal guide holes 1528A-C. Particularly, each one of the distal guide holes 1528A-C may be configured to removably or non-removably engage a proximal engaging portion 1532 of a respective one of the pump units 1508A-C when assembled thereto. For example, as illustrated in FIG. 15, the proximal engaging portion 1532 may include a pin connector coupled to a corresponding elongated operable element 1534 of the pump unit 1508C. In this case, the pin is sized and shaped to removably or non-removably engage the distal guide holes 1528C.

Contrary to having the receiving surfaces 1526A-C conforming or mating the pump units 1508A-C and/or providing a seal to the receiving surfaces 1526A-C for the purpose of mitigating or preventing blood clotting, the receiving surfaces 1526A-C and/or the distal guide holes 1528A-C may be configured to create a flow gap between the receiving surfaces 1526A-C and the pump units 1508A-C, when assembled thereto, that facilitates blood flow therebetween for the same purpose. Further, a fin or similar structure may be provided to direct or modify blood flow through the flow gap for mitigating or preventing blood clotting therein.

The optional anchor 1502 may be implemented to the implantable medical device 700, with the necessary change(s), appreciable to the skilled addressee, having been made, if applicable. The optional anchors 112, 714, with or without the optional anchor rods 114, 716, may be implemented to the introducer unit 1512 of the implantable medical device 1500.

Figure 20:
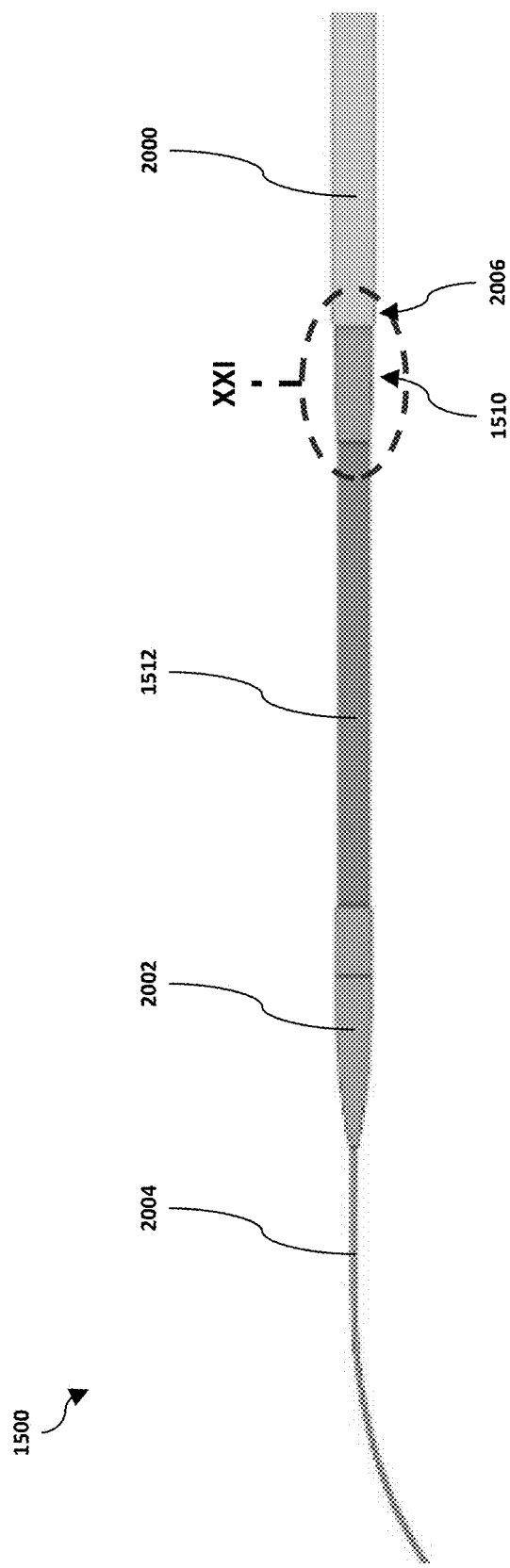
FIGS. 20-21 are plan views of the implantable medical device of FIG. 7 provided with sheath and removably engaged in the sheath for delivery, in accordance with an embodiment.
Figure 21:
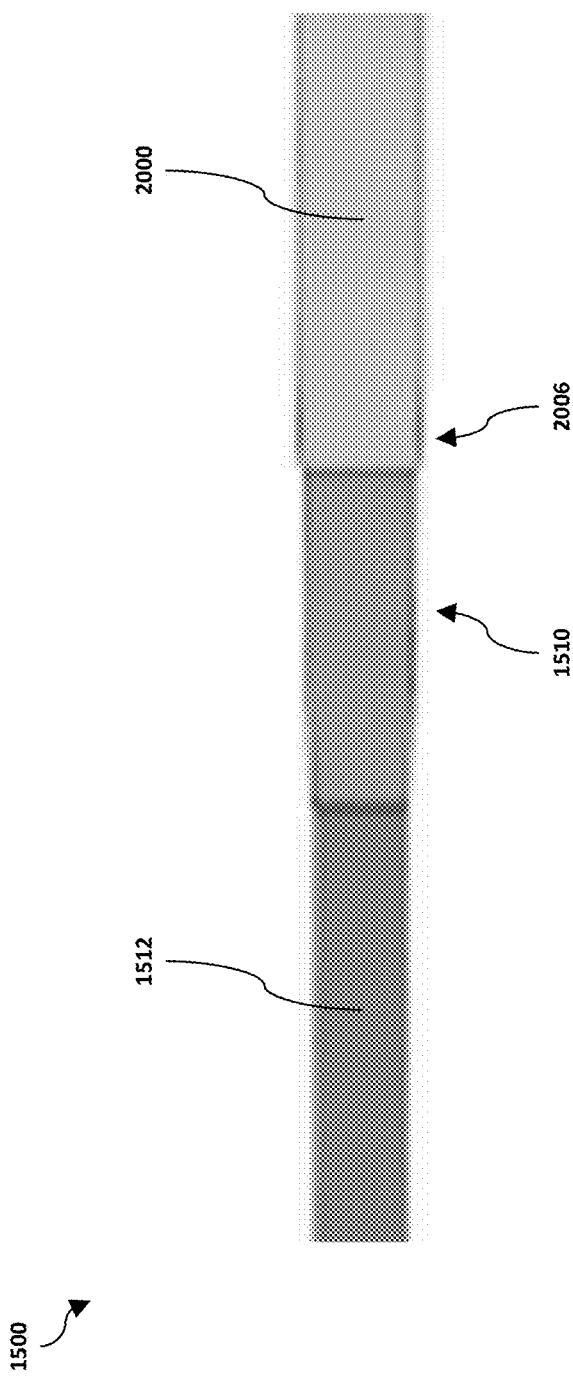

FIGS. 20-21 illustrate the implantable medical device 1500 provided with a sheath 2000 (also collectively referred to herein as a "medical device assembly") with which the introducer unit 1512 of the implantable medical device 1500 is releasably engageable, according to embodiments. FIG. 20 illustrates the implantable medical device 1500 provided with a tip 2002, similar to the tips 110, 712, that is releasably attached to the introducer unit 1512, and a guidewire 2004, similar to the guidewires 108, 710, that is attached to the tip 2002. The introducer unit 1512 projects distally outwardly from the sheath 2000. The attachment between the guidewire 2004 and the tip 2002 may be removable or non-removable and/or rotatable or non-rotatable. The releasable interaction between the implantable medical device 1500, notably the introducer unit 1512, and the sheath 2000 allows the implantable medical device 1500 to be intraluminally deliverable while the sheath is introduced in a lumen of body conduit(s) for implanting the implantable medical device without leaving the sheath afterward as it is removed after the procedure.

As illustrated in FIG. 21, the proximal end portion 1510 of the introducer unit 1512 is releasably engageable in an engagement end portion 2006 of the sheath 2000, such that the introducer unit 1512 may be caused to exit the sheath 2000 to be delivered in a lumen of body conduit(s) and implanted at an intraluminal implantation site. The sheath 2000 may or may not contain the pump units 1508A-C therein. When contained in the sheath 2000, the pump units 1508A-C are in the one-after-the-other arrangement and the implantable medical device 1500 is in the unassembled configuration. When the pump units 1508A-C are not contained in the sheath 2000, are contained in the sheath 2000 and are slidably received in the introducer unit 1512. Prolongation wires 2502A-C, which are similar to the prolongation wires 1300A-C, are not shown in FIG. 21 since they are hidden by the introducer unit 1514 and the sheath 2002. The prolongation wires extend along the entire combined length of the sheath 2000 and the introducer unit 1512. The prolongation wires are attachable to the corresponding elongated operable elements of the pump units 1508A-C, which may be moved inside along the sheath 2000 upon pulling on the prolongation wires from the distal end portion of the introducer unit 1512.

As best illustrated in FIG. 21, the engagement end portion 2006 of the sheath 2000 has a tapered shape as described hereinbefore but may be generally less pronounced. In use, the engagement end portion 2006 of the sheath 2000 is the second taper encountered by intraluminal access, such as a percutaneous intraluminal access, after the taper of the tip 2002. Typically, such intraluminal access is dilated by the tip 2002 first, and is then further dilated by the engagement end portion 2006 as the implantable medical device 1500 and the sheath 2000 are advanced therethrough. Although a tip 2002 is illustrated in FIG. 20, it may not necessarily be the case as the distal end portion 2008 of the introducer unit 1512 may have a tapered shape per se, as described hereinbefore.

The proximal end portion 1510 of the introducer unit 1512 may also sealingly engage the engagement end portion 2006 of the sheath 2000 to provide a fluid tight engagement therewith. The sealing engagement may be provided by the proximal end portion 1510 of the introducer unit 1512 being slightly oversized relative to the engagement end portion 2006 of the sheath 2000 so as to slightly dilate it. Alternatively, it may be a snug fit. The sealing engagement between the implantable medical device 1500 and the sheath 2000 may be advantageous in presence of blood which, inside the sheath 2000 and/or the implantable medical device 1500, as the case may be, may be a cause of malfunction.

Although the implantable medical device 1500 and the sheath 2000 are described and illustrated in FIGS. 20-21 as engaging at the level of the proximal end portion 1510 of the introducer unit 1512, such engagement may take place anywhere along the introducer unit 1512 of the implantable medical device 1500.

Figure 22:
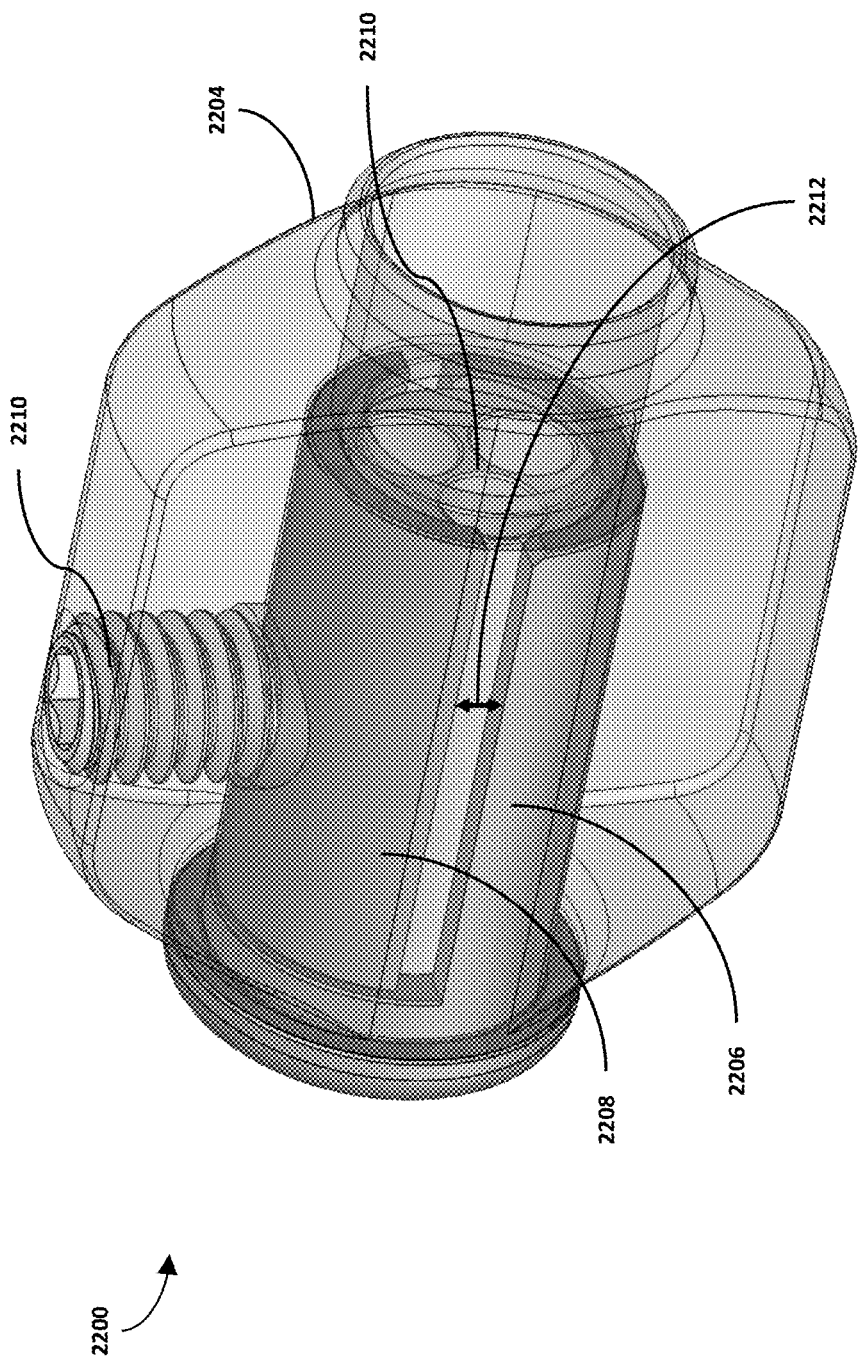
FIG. 22 is a perspective views of a compression securing mechanism for the implantable medical device of FIG. 7, in accordance with an embodiment.
Figure 24:
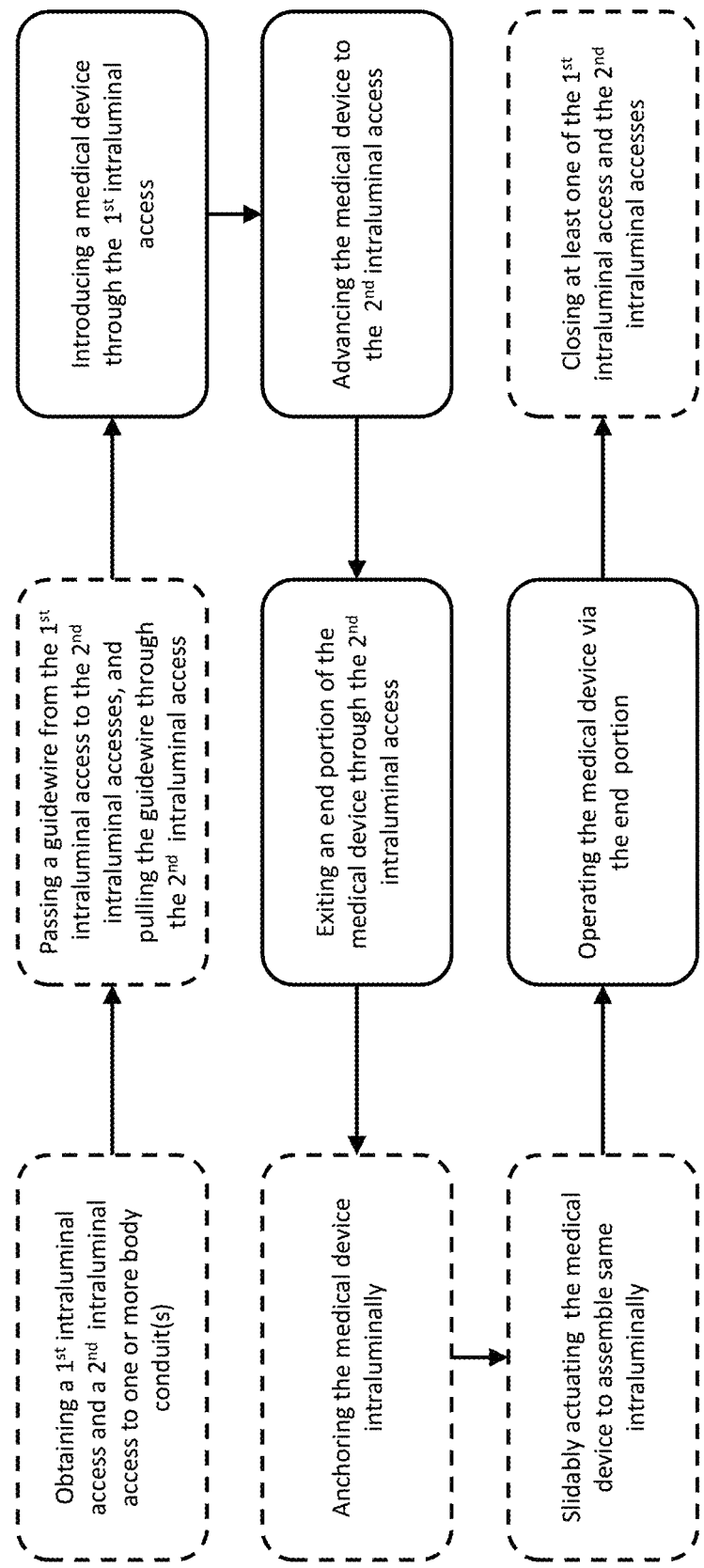
FIG. 24 is a schematic representation of a method of implanting the implantable medical devices of FIGS. 1 and 7, in accordance with a third aspect of the present technology.

FIG. 22 illustrates an optional compression securing mechanism 2200 as an embodiment of the securing mechanism 824 that may be provided to the implantable medical device 1500, as well as to the implantable medical device 700, for securing all the elongated operable elements of the pump units 1508A-C to the introducer unit 1512. The securing mechanism 2200 may be integrated anywhere on the implantable medical device 1500, such as on the proximal end portion 1510 of the introducer unit 1512 next to the tip 2002 so as to be operable when the implantable medical device 1500 is implanted.

The compression securing mechanism 2200 includes a casing 2204 enclosing a fixed compression element 2206, a movable compression element 2208, an actuator 2210 coupled to the movable compression element 2208 for moving the movable compression element 2208, and a sleeve 2210, which as illustrated has three passageway for slidably receiving the elongated operable elements of the pump units 1508A-C therein. The sleeve 2210 is disposed between and is compressible by the fixed and movable compression elements 2206, 2208. The sleeve 2210 is configured to prevent damaging the elongated operable elements when slid therein and also to sealingly engage the elongated operable elements for providing a fluid tight engagement therewith. As such, the sleeve 2210 may be made of polymer or elastomer. The fixed and movable compression elements 2206, 2208 may be sized and shaped to conform to the outer shape of the sleeve 2210.

As illustrated, the compression securing mechanism 2200 is in the unsecured conformation with the fixed and movable compression elements 2206, 2208 being spaced apart from each other by a space 2212. The compression securing mechanism 2200 is adjusted from the unsecured conformation to the secured conformation by operating the actuator 2210, which as illustrated is a set screw, to move the movable compression element 2208 toward the fixed compression element 2206 to compress the sleeve 2210, thereby reducing the space 2212. In the secured conformation, the sleeve 2210 frictionally engages the elongated operable elements.

The compression securing mechanism 2200 may be provided to the implantable medical device 100.

With reference now to FIGS. 23A-C and 24, a method of implanting 2400 the implantable medical devices 100 and 700 will be described, in accordance with a third aspect of the present disclosure.

The method of implanting 2400 includes:

At 2402, obtaining a first intraluminal access (also referred herein to as a first body conduit intraluminal access) and a second intraluminal access (also referred herein to as a second body conduit intraluminal access) to a lumen of a first body conduit and second body conduit, respectively, of a subject to be treated by the implantable medical devices 100 and 700, according to embodiments. The first intraluminal access may be located on the lower body of the subject, such as on a femoral artery of a subject. The second intraluminal access may be located on the upper body of the subject, such as on a subclavian/axillary artery of the subject. Each one of the first intraluminal access and the second intraluminal access may a percutaneous body conduit access obtained by medical procedure(s) known in the art (e.g., vis the Seldinger technique) or may be natural body conduit access(es), such as esophageal, tracheal, urethral, and/or rectal, which may require anesthesia or any other medical or surgical preparation. For example, the first intraluminal access may be a percutaneous body conduit access obtained by medical procedure(s), whereas the second intraluminal access may be a percutaneous body conduit access obtained by medical procedure(s) or be a natural access. Alternatively, the first intraluminal access and the second intraluminal access may be obtained and thus located on a same body conduit, which may have an acute angle or be tortuous in nature.

At 2404, optionally, the method may further include the passing the guidewire 108, 710 from the first intraluminal access to the second intraluminal access (optional items are represented by dash lines in FIG. 24), according to embodiments. Particularly, the guidewire 108, 710 may be passed between the first intraluminal access and the second intraluminal access by introducing the guidewire in the lumen of the first body conduit through the first intraluminal access, guiding the guidewire 108, 710 to the second intraluminal access, such as by capturing the distal end portion of the guidewire 108, 710, for example using a snare or any other appropriate tool, via the second intraluminal access, and exiting the guidewire through the second intraluminal access. Depending on the vascular morphology of the subject, the interconnection between the first body conduit and the second body conduit may have an acute angle, or any of the first body conduit and the second body conduit may be tortuous in nature, which altogether may be difficult to navigate for the implantable medical device 100, 700 (and some other medical device of this art as well). In such circumstances, the use of the guidewire 108, 710 may be a desirable to prevent or minimize trauma to the intima in the case of a blood vessel.

Referring back to 2404, optionally, the method may further include pulling the guidewire 108, 710 from the second intraluminal access so that (i) to introduce the implantable medical device 100, 700 in the lumen of the first body conduit through the first intraluminal access (optionally while concurrently pushing on the proximal end portion of the implantable medical device 100, 700), (ii) to advance the implantable medical device 100, 700 in the lumen of at least one of the first body conduit and the second body conduit to the second intraluminal access, and (iii) to exit the distal end portion of the implantable medical device 100, 700 through the second intraluminal access, according to embodiments.

At 2406, introducing the implantable medical device 100, 700, with the introducer unit 102 or introducer unit 702 first, in the lumen of the first body conduit through the first intraluminal access, according to embodiments. For example, a sheath (e.g., a delivery or implantation sheath) containing the implantable medical device 100, 700 therein may be pushed through the first intraluminal access. Alternatively, the implantable medical device 100, 700 may be introduced through the first intraluminal access without using a sheath by pushing on its proximal end portion.

At 2408, advancing the implantable medical device 100, 700 in the lumen of the first body conduit to the lumen of the second body conduit up to the second intraluminal access, according to embodiments. Particularly, the implantable medical device 100, 700 may be advanced by pushing on a sheath containing same therein or by pushing on the proximal end portion of the implantable medical device 100, 700.

At 2410, exiting the distal end portion of the implantable medical device 100, 700 through the second intraluminal access so that the implantable medical device 100, 700 is positioned partially inside the lumen of at least one of the first body conduit and the second body conduit, according to embodiments. As such, the pump element 106, 106A-C or the pump elements 707, 707A-C (or the functional unit, as the case may be) is/are positioned intraluminally, while the distal end portion of the introducer unit 102 or introducer unit 702 may be positioned partially extraluminally or extracorporeally. Also, exiting the second intraluminal access may cause hemostasis, either partially or totally, at the second intraluminal access. For example, the bulge 300, 400, 1000, 1100 of the introducer unit 102 or introducer unit 702 may engage the second intraluminal access in a fluid-thigh manner for doing so. Particularly, the implantable medical device 100, 700 may be caused to exit by pushing on a sheath containing same therein or by pushing on the proximal end portion of the implantable medical device 100, 700.

At 2412, optionally, the method may further include anchoring the implantable medical device 100, 700 by conversion of the anchor 112, 714 from the contracted configuration (e.g., as the anchor 112, 714 is configured when the implantable medical device 100, 700 is contained in a sheath during delivery and/or implantation of the implantable medical device 100, 700) to the expanded configuration to removably engage a lumen wall of any one of the first body conduit and the second body conduit, according to embodiments.

At 2414, optionally, specifically when the implantable medical device 700 is implanted, the method may further include slidably actuating any one of the elongated operable elements 708, 708A-C and the longitudinal guide holes 802, 802A-C relative to the other corresponding one of the elongated operable elements 708, 708A-C and the longitudinal guide holes 802, 708A-C to cause at least one of the following: (i) to introduce a corresponding one of the pump elements 707, 707A-C in the lumen of the first body conduit through the first intraluminal access, and (ii) to slidably assemble one of the pump elements 707, 707A-C with a corresponding one of the introducer units 702 intraluminally, according to embodiments. To advance or navigate in a lumen of a body conduit to implant the implantable medical device 700, for example, the method may further include preventing any one of the respective elongated operable elements 708, 708A-C from sliding in the corresponding one of the longitudinal guide holes 802, 802A-C as the corresponding pump elements 106, 707A-C are pulled by the corresponding guidewires 108, 710.

At 2416, operating the implantable medical device 100, 700 via its distal end portion that is positioned extraluminally or extracorporeally, according to embodiments. Particularly, the implantable medical device 100, 700 may be operated by operatively connecting the distal end portion, including the connector 212, 832 to a controller configured to operate the implantable medical device 100, 700. The tips 110, 712, when present, may also be removed to operatively connect the implantable medical device 100, 700 to the controller. Alternatively, the implantable medical device 100, 700 may be operated wirelessly.

At 2418, optionally, the method may further include the closing at least one of the first intraluminal access and the second intraluminal access when such access(es) is a percutaneous body conduit access obtained by medical procedure, according to embodiments.

With reference now to FIGS. 25A-J, an example of implantable medical device 1500 along with a method of implanting the same in a blood vessel will be described, according to embodiments.

Figure 25A:
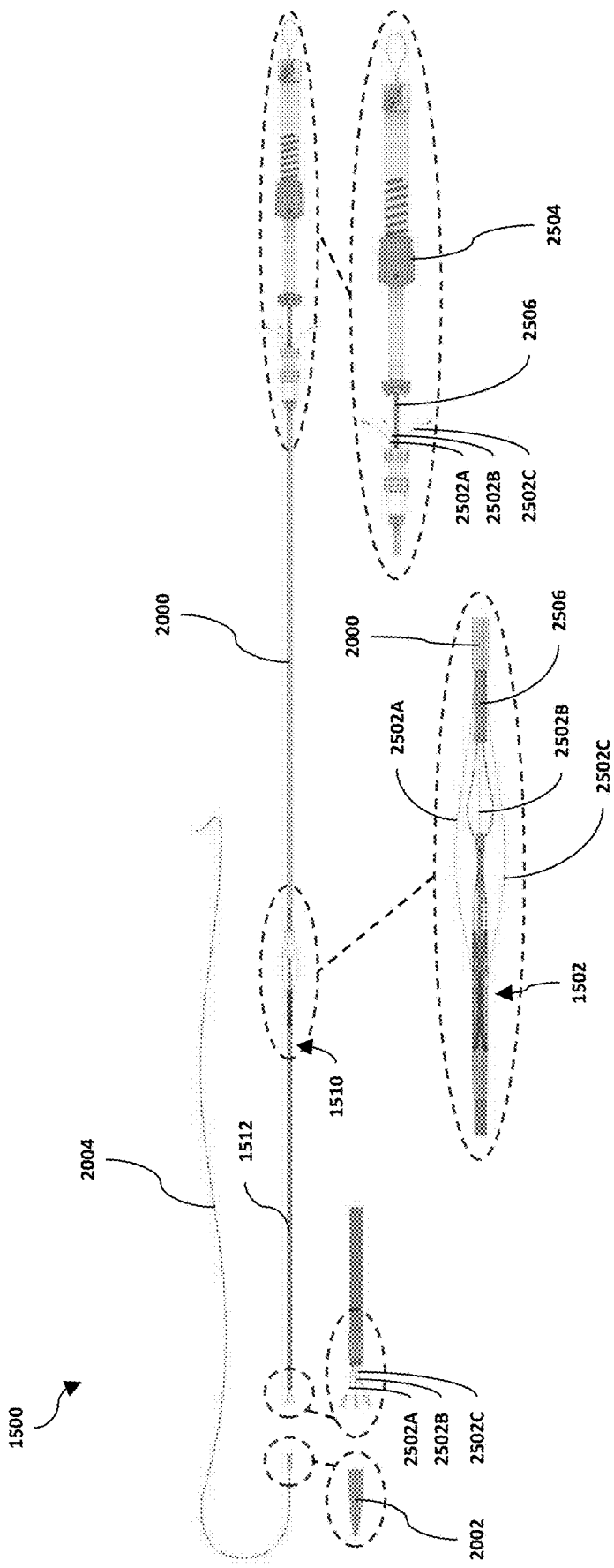
FIGS. 25A-J is a schematic representation of a method of implanting the implantable medical device of FIG. 7, in accordance with a third aspect of the present technology.

FIG. 25A illustrates an example of an implantable medical device 1500 provided with a guidewire 2004 attached to the tip 2002 of a tapered shape that is detached from the introducer unit 1512 such that distal end portions of prolongation wires 2502A-C are visible. The prolongation wires 2502A-C correspond to the prolongation wires 1300A-C. The distal end portions of the prolongation wires 2502A-C project outwardly from a distal cavity of the introducer unit 1512. The distal cavity is located under the tip 2002 when attached to the introducer unit 1512. The prolongation wires 2502A-C are slidably received in the distal cavity and the introducer unit 1512, pass through the three radial openings of the anchor 1502, which is next the proximal end portion 1510 of the introducer unit 1512, and run in the sheath 2000 up to a handle 2504 thereof.

A capture element provided to the anchor 1502 may be removably attached to a rod 2506. The handle 2504 is manipulable by an operator for slidably moving the rod 2506 in the sheath 2000, causing the introducer unit 1512 to be pushed outside the sheath 2000 and/or, when attached to the rod 2506, to be pulled inside the sheath 2000.

Figure 25B:
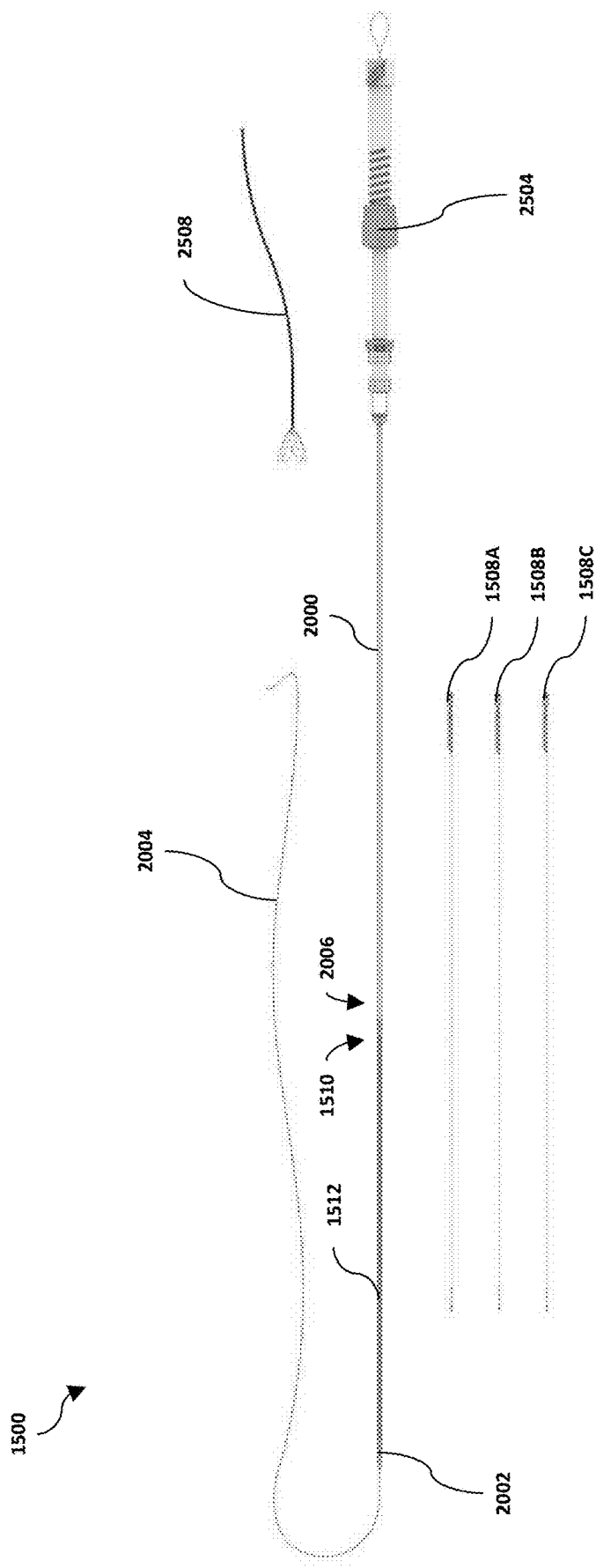

FIG. 25B illustrates the example of the implantable medical device 1500 with the tip 2002 attached to the introducer unit 1512, and the proximal end portion 1510 of the introducer unit 1512 removably engaged in the engagement end portion 2006 of the sheath 2000, so as the implantable medical device 1500 is ready for implantation. Also illustrated are pump units 1508A-C to be removably attached to the corresponding prolongation wires 2502A-C for being pulled inside the sheath 2000. Further illustrated, is an optional snare 2508 that may be used to capture the guidewire 2004.

Figure 25C:
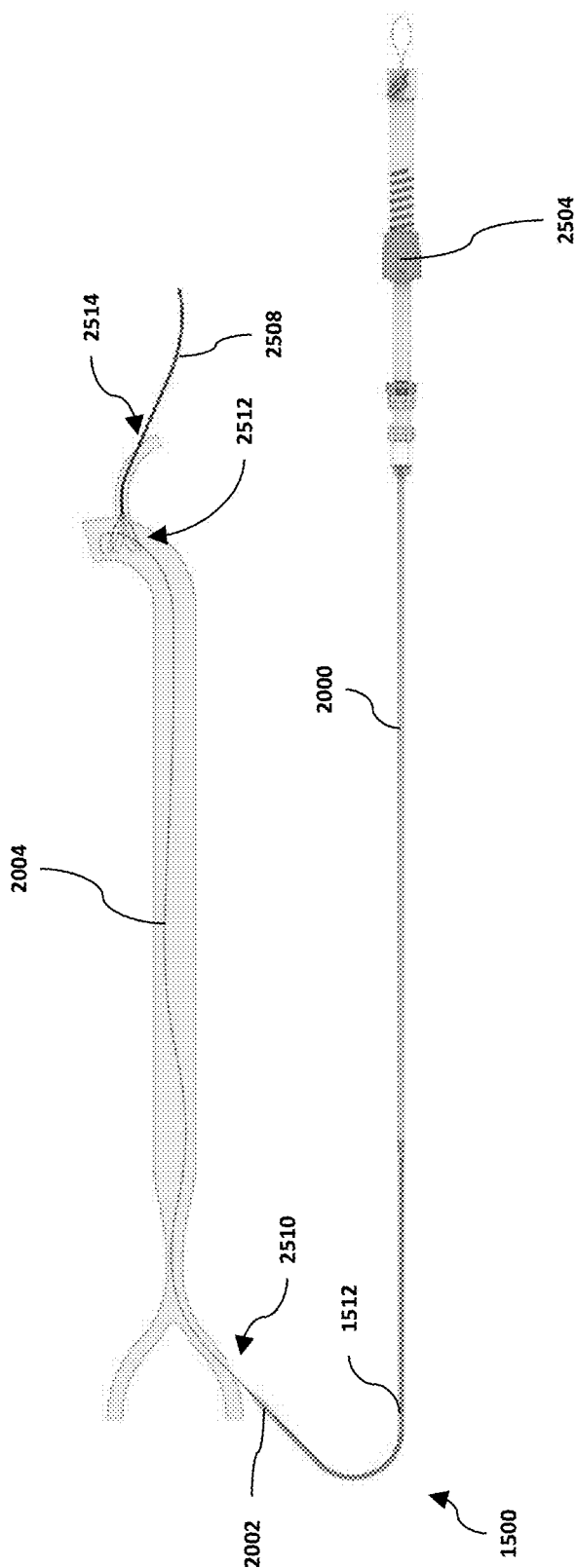

As for the method of implanting, FIG. 25C refers to introducing, such as by pushing, the guidewire 2004 of the implantable medical device 1500 in a first intraluminal access 2510, such as a first percutaneous arterial or venous intraluminal access; routing the guidewire 2004 to an intermediate location 2512 in a lumen of a blood vessel (also referred to herein as "intermediate intraluminal location"); introducing, such as by pushing, the snare 2508 in a second intraluminal access 2514, such as a second percutaneous arterial or venous intraluminal access; routing the snare to the intermediate location 2512; and capturing the guidewire 2004 with the snare 2508. The routing of the snare 2508 may be performed before, during, or after the routing of the guidewire 2004.

Figure 25D:
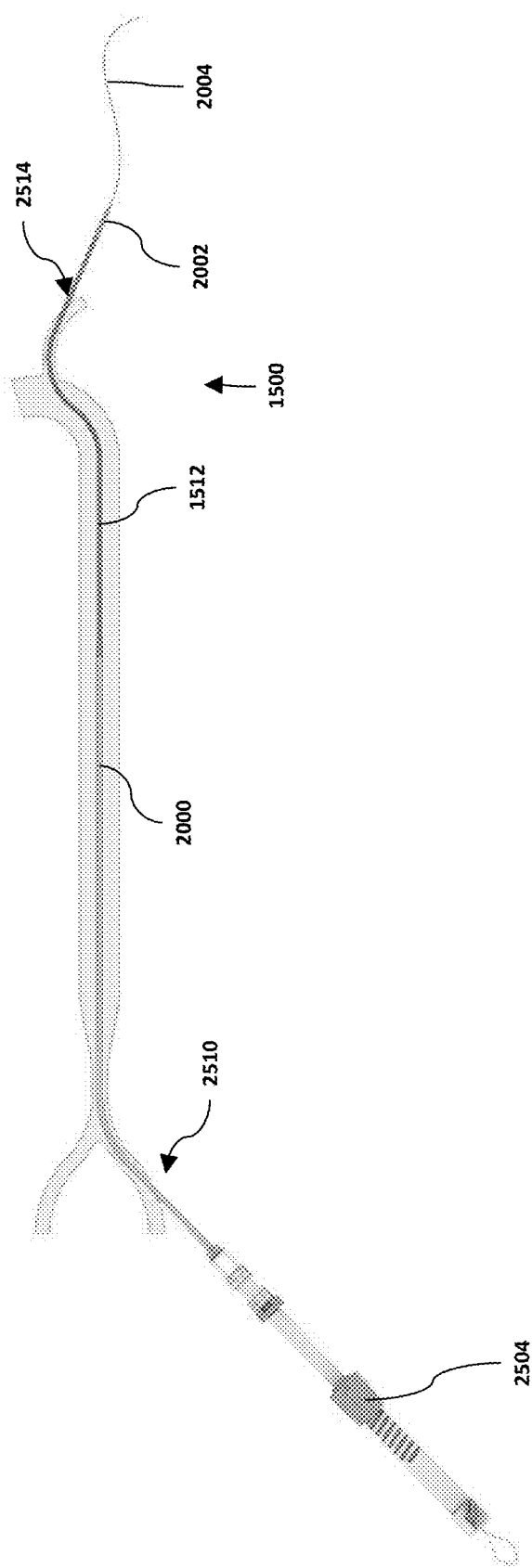

FIG. 25D refers to pulling the snare 2508 through the second intraluminal access 2514 for moving or navigating the implantable medical device 1500 along a lumen of blood vessel(s) up to the second intraluminal access 2514; optionally passing or externalizing at least partially the distal end portion of the introducer unit 1512 through the second intraluminal access 2514; and optionally detaching the snare 2508 from the guidewire 2004. The first and second intraluminal accesses may optionally be made by performing or obtaining a second intraluminal access 2514 that has a diameter smaller than the diameter of the first intraluminal access 2510 in which the implantable medical device 1500 is initially introduced. This way the distal end portion of the introducer unit 1512, being of a tapered shape, sealingly engages in a fluid thigh manner the second intraluminal access 2514 when partially passed or externalized therethrough and at least partially achieve hemostasis.

Figure 25E:
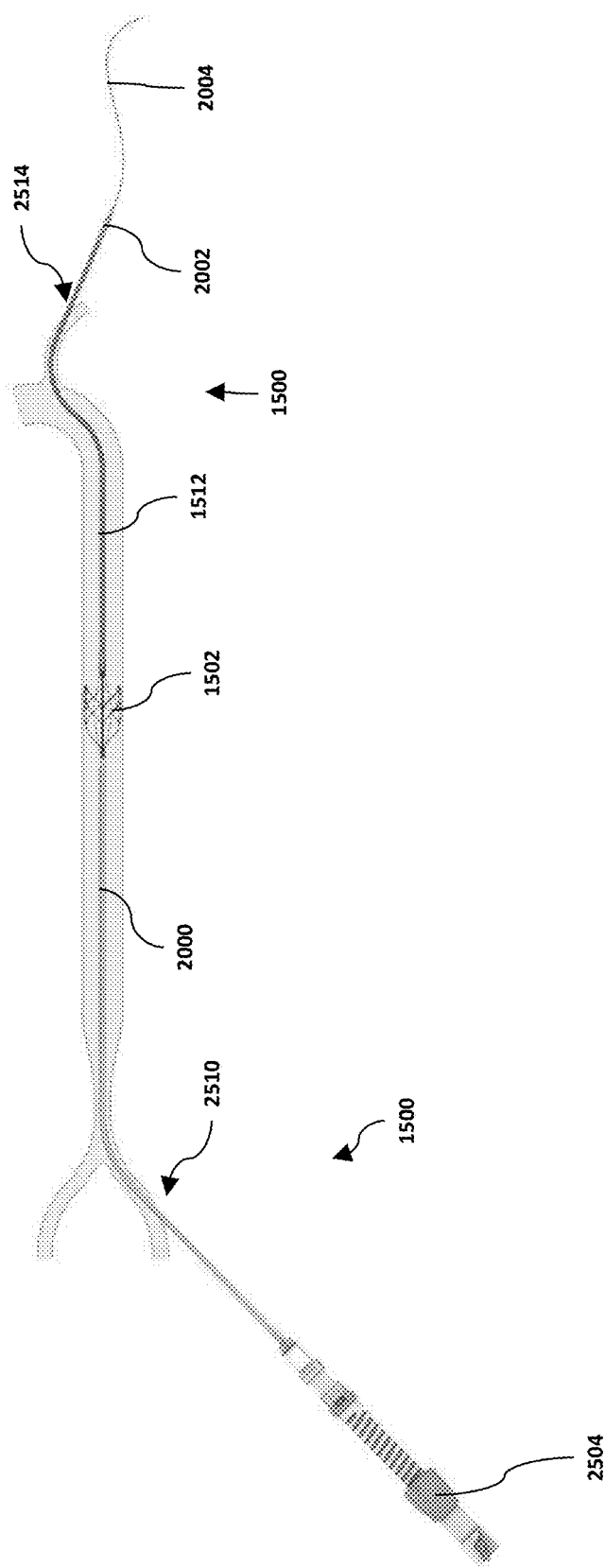

FIG. 25E refers to optionally manipulating the handle 2504 of the implantable medical device 1500 to anchor the implantable medical device 1500 at an intraluminal implantation site.

Figure 25F:
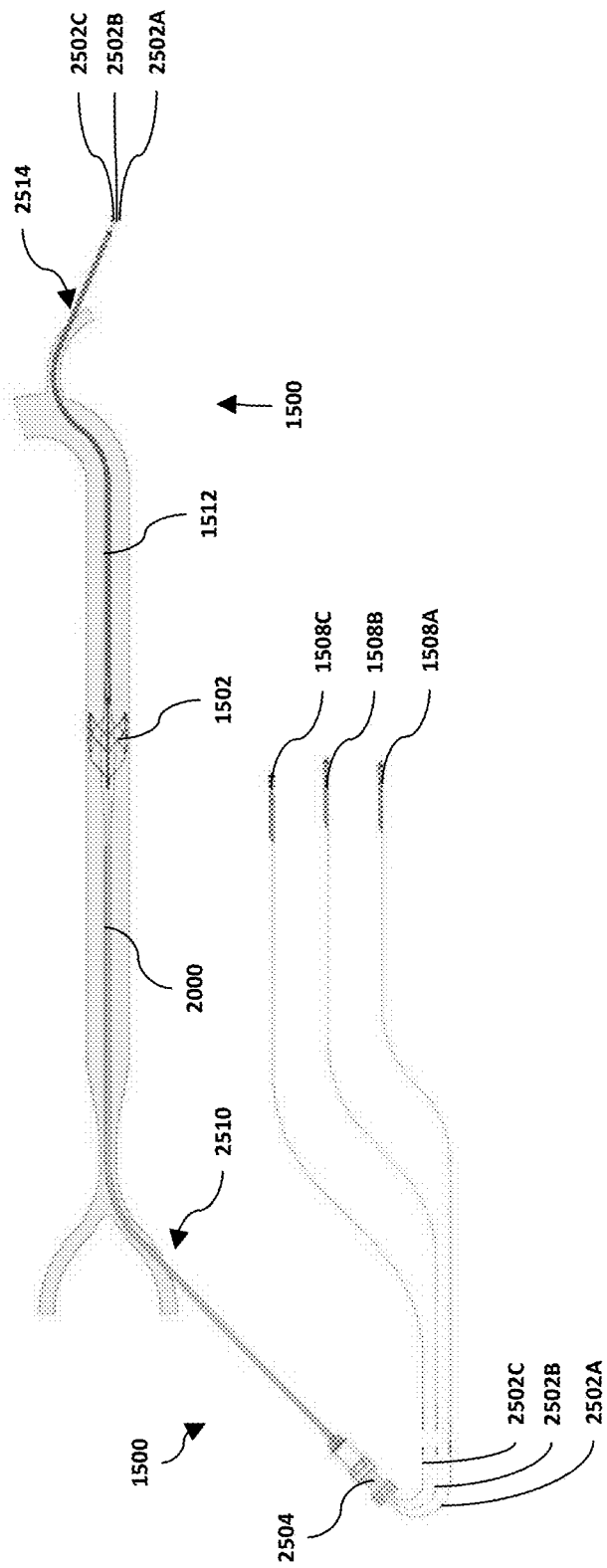
Figure 25G:
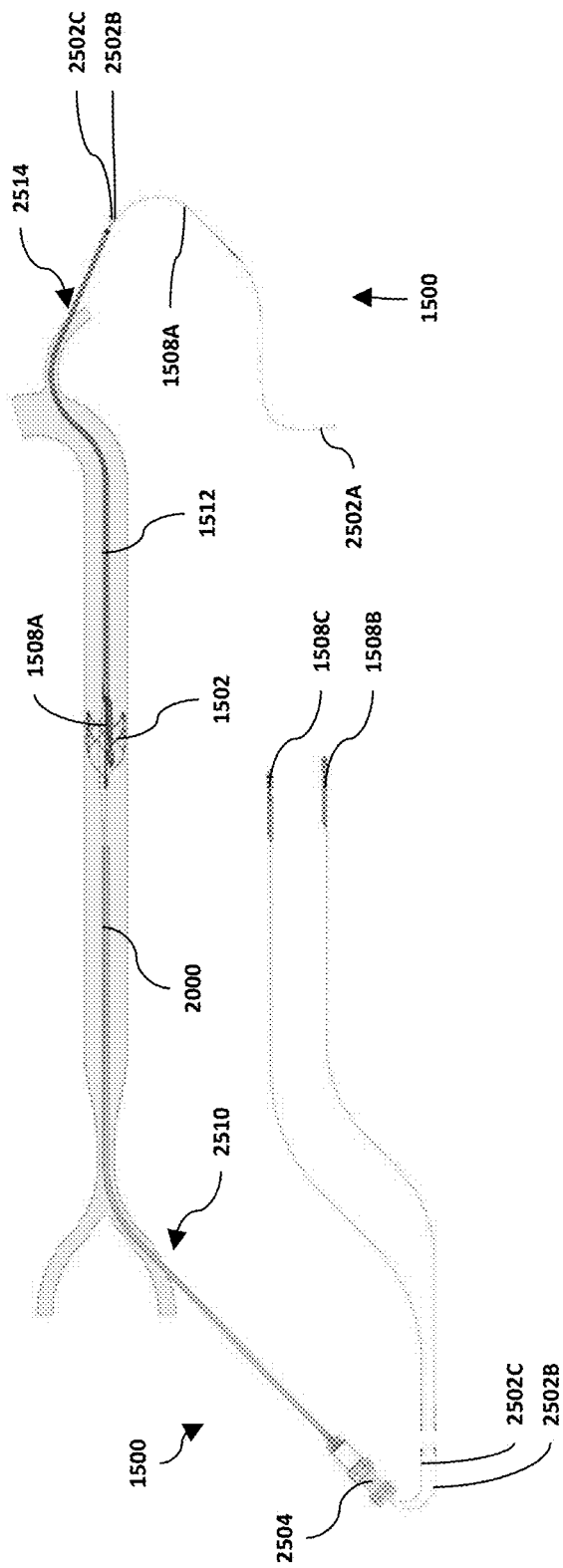
Figure 25H:
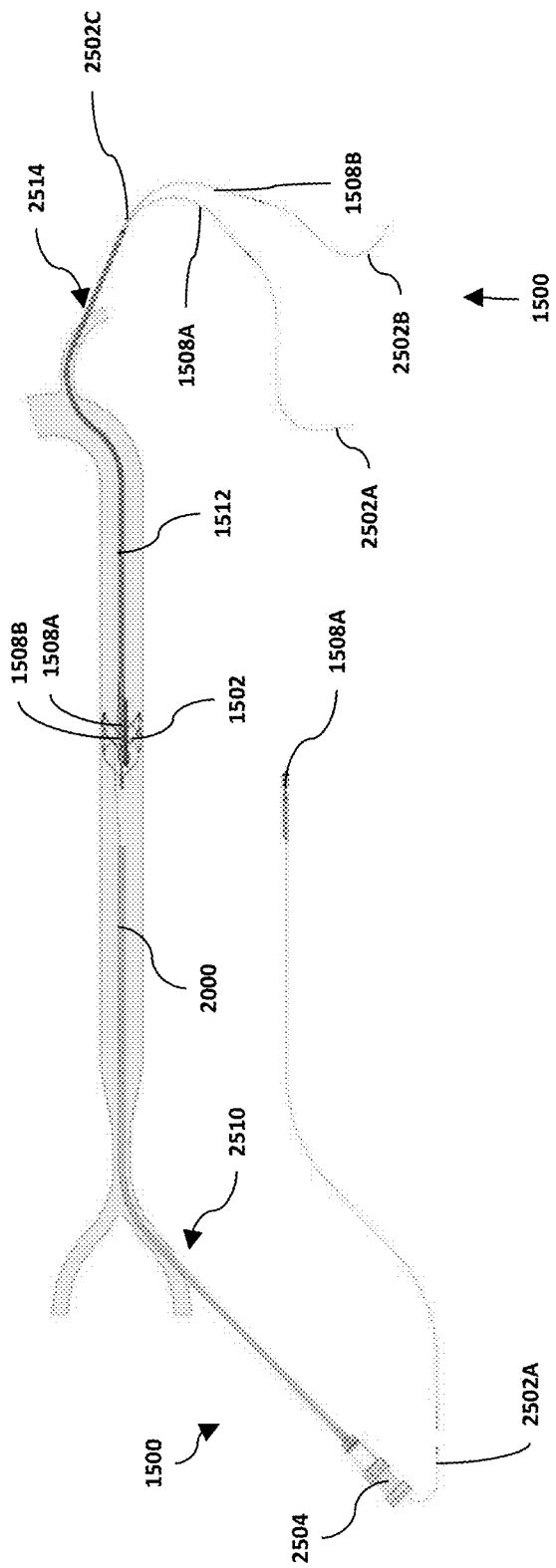

FIG. 25F-H refers to optionally attaching one or more prolongation wires 2502A-C to corresponding pump units 1508A-C, for example to respective elongated operable element(s) thereof, if not already attached thereto; pulling on the prolongation wires 2504A through the second intraluminal access 2514 to move the pump units 1508A inside the sheath 2000 up to the intraluminal implantation site, and eventually assembling the pump unit 1508A to the introducer unit 1512; pulling on the prolongation wires 2504B through the second intraluminal access 2514 to move the pump units 1508B inside the sheath 2000 up to the intraluminal implantation site, and eventually assembling the pump unit 1508B to the introducer unit 1512; pulling on the prolongation wires 2504C through the second intraluminal access 2514 to move the pump units 1508C inside the sheath 2000 up to the intraluminal implantation site, and eventually assembling the pump unit 1508C to the introducer unit 1512. One or more pump units 1508A-C may be positioned inside or outside the sheath 2000 and/or before or after the first intraluminal access 2510 before being moved by pulling on the corresponding prolongation wires 2502A-C.

Figure 25I:
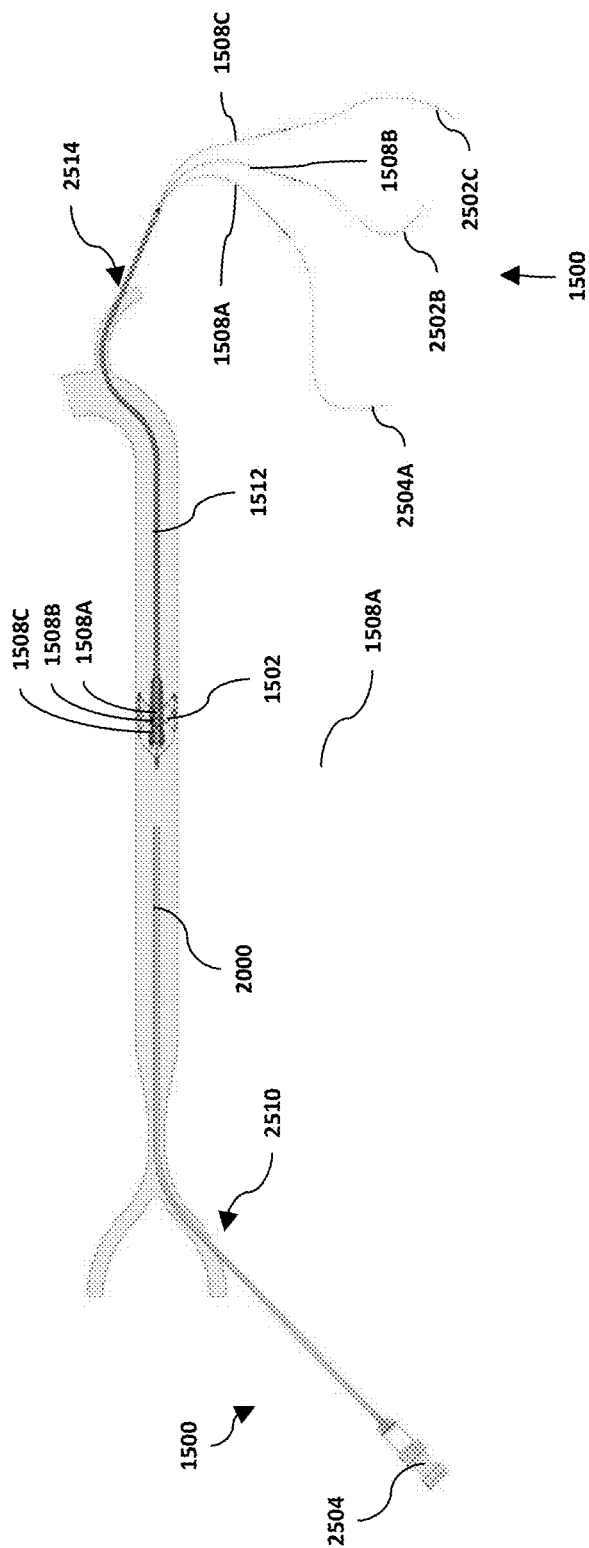

FIG. 25I refers to optionally detaching the implantable medical unit 1500 from the sheath 2000, such as from the rod 2506, if attached thereto.

Figure 25J:
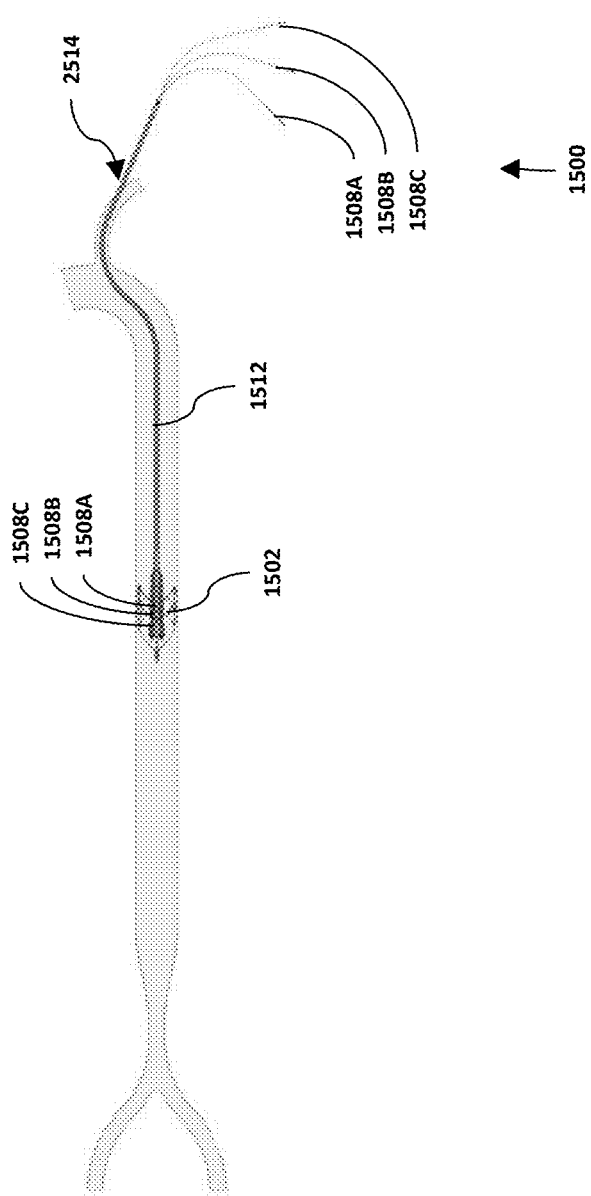

FIG. 25J refers to optionally removing the sheath 2000 from the blood vessel through the first intraluminal access 2510, and optionally closing the first intraluminal access 2510.

The method of implanting may further include optionally connecting the distal end portion of one or more pump units 1508A-C, for example the respective elongated operable element thereof, to one or more corresponding controllers and optionally operating the pump units 1508A-C.

It will appreciate that reference to the implantable medical device 1500 and components thereof for describing the method of implanting 2500 is only made as example since the method of implanting 2500 may be implemented with any suitable implantable medical device.

Figure 26:
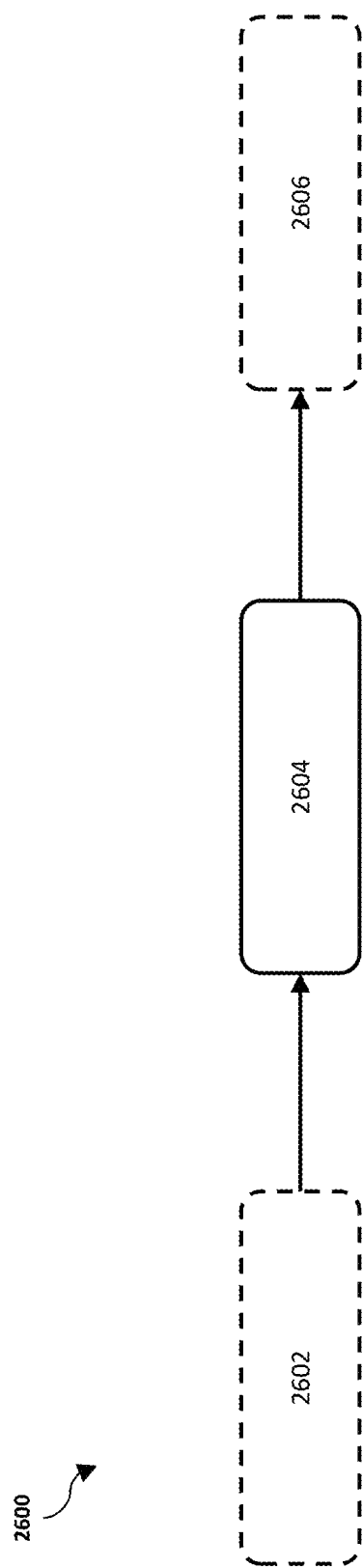
FIG. 26 is a schematic representation of a method of implanting a pump unit, in accordance with a third aspect of the present technology.

With reference now to FIG. 26, a method of implanting 2600 a pump unit will be described, according to embodiments. The pump unit includes a pump element and an elongated operable element operatively coupled to the pump element for operating the pump element through the elongated operable element by a controller connectable to the elongated operable element. The pump unit may include a tapered portion oriented toward the elongated operable element so that when pulled by the elongated operable element thought an intraluminal access, the tapered portion dilates the intraluminal access while passing therethrough. The method of implanting 2600 includes (Optional elements of the method of implanting 2600 are represented by dash lines in FIG. 26):

At 2602, optionally obtaining a first intraluminal access, such as a first percutaneous arterial or venous intraluminal access, and a second intraluminal access, such as a second percutaneous arterial or venous intraluminal access.

At 2604, navigating an elongated operable element, such as a pump cable or a pump driveshaft, of the pump unit from the first intraluminal access to the second intraluminal access to position the pump element inside a lumen of a blood vessel and a portion of the elongated operable element close to or at least partially thought the second intraluminal access.

Navigating the elongated operable element may include, optionally introducing the elongated operable element through the first intraluminal access and optionally routing the elongated operable element to an intermediate location in a lumen of a blood vessel; optionally introducing a snare through the second intraluminal access, optionally routing the snare to the intermediate location, optionally capturing the elongated operable element with the snare, optionally pulling the snare to externalize the elongated operable element through the second intraluminal access, and/or optionally pulling the elongated operable element, with or without the snare, to position the pump element at an intraluminal implantation site inside a lumen of body conduit(s).

At 2606, optionally connecting the elongated operable element to a controller and optionally operating the fluid displacement portion.

Figure 27:
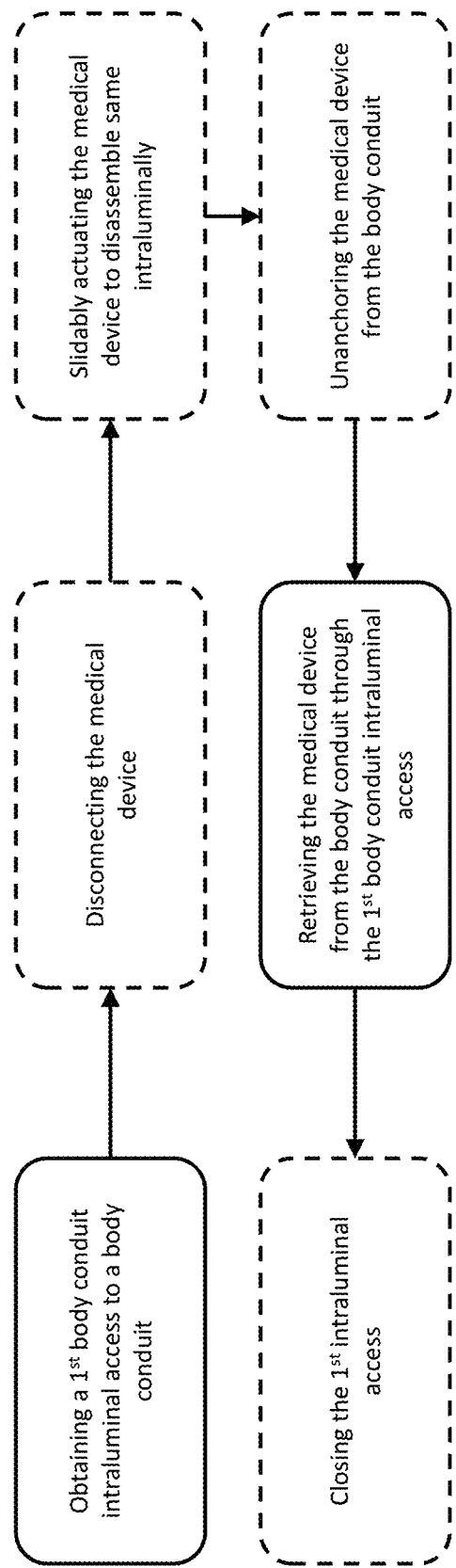
FIG. 27 is a schematic representation of a method of explanting the implantable medical devices of FIGS. 1 and 7, in accordance with a fourth aspect of the present technology.

With reference now to FIG. 27, a method of explanting 2700 the implantable medical device 100, 700 will be described, in accordance with a fourth aspect of the present disclosure. The implantable medical device 100, 700 to be explanted is implanted in a body conduit of a subject in such a way that the pump element 106, 106A-B or the pump elements 707, 707A-C is/are positioned in a lumen of a first body conduit, while the introducer unit 102 or the introducer unit 702 extends along the lumen of the first body conduit and also along a lumen of a second body conduit up to a second intraluminal access (also referred herein to as a second body conduit intraluminal access) where the introducer unit 102 or the introducer unit 702 is positioned partially therethrough. Therefore, the second intraluminal access is located on the distal side of the implantable medical device 100, 700 (i.e., toward the distal end portion of the implantable medical device 100, 700).

The method of explanting 2700 includes:

At 2702, obtaining a first intraluminal access (also referred herein to as a first body conduit intraluminal access) to the lumen of the first body conduit on a segment thereof that is located on a proximal side of the implantable medical device (i.e., toward the proximal end portion of the implantable medical device 100, 700), according to embodiments. The first intraluminal access may be located on the lower body of the subject, such as on a femoral artery of a subject. The second intraluminal access may be located on the upper body of the subject, such as on a subclavian/axillary artery of the subject. Each one of the first intraluminal access and the second intraluminal access may a percutaneous body conduit access obtained by medical procedure(s) known in the art (e.g., vis the Seldinger technique) or may be natural body conduit access(es), such as esophageal, tracheal, urethral, and/or rectal, which may require anesthesia or any other medical or surgical preparation. For example, the first intraluminal access may be a percutaneous body conduit access obtained by medical procedure(s), whereas the second intraluminal access may be a percutaneous body conduit access obtained by medical procedure(s) or be a natural access. Alternatively, the first intraluminal access and the second intraluminal access may be obtained and thus located on a same body conduit, which may have an acute angle or be tortuous in nature.

At 2704, optionally, disconnecting the distal end portion of the implantable medical device 100, 700 from a controller configured for operating the implantable medical device 100, 700 (optional items are represented by dash lines in FIG. 27), according to embodiments. Of course, this is not required when the implantable medical device is operated wirelessly.

At 2706, optionally, specifically when the implantable medical device 700 is explanted, the method may further include slidably actuating any one of the elongated operable elements 708, 708A-C and the longitudinal guide holes 802, 802A-C relative to the other corresponding one of the elongated operable elements 708, 708A-C and the longitudinal guide holes 802, 802A-C to slidably disassemble any one of the pump elements 707, 707A-C (or the functional unit(s), as the case may be) from the corresponding one of the introducer units 702 intraluminally, according to embodiments.

At 2708, optionally, the method may further include anchoring the implantable medical device 100, 700 by conversion of the anchor 112, 714 from the expanded configuration (since the implantable medical device 100, 700 is anchored) to the contracted configuration (e.g., when the implantable medical device 100, 700 is contained in a sheath) to removably engage a lumen wall of any one of the first body conduit and the second body conduit, according to embodiments.

At 2708, retrieving the implantable medical device 100, 700 from the first body conduit and the second body conduit through the first body conduit intraluminal access, according to embodiments. In some embodiments, the implantable medical device 100, 700 may be retrieved by introducing a sheath (e.g., a retrieval or explanation sheath) in the lumen of the first body conduit through the first intraluminal access, advancing the sheath therein next to the proximal end portion of the implantable medical device 100, 700, taking at least partially the implantable medical device 100, 700 in the sheath, and removing the sheath from the first intraluminal access. In some embodiments, the implantable medical device 100, 700 may be retrieved by capturing the capture element 116, 718, 720 of the implantable medical device 100, 700, for example using a snare or any other appropriate tool, via the first body conduit intraluminal, and pulling on the tool so that the implantable medical device 100, 700 is taken within the sheath.

Alternatively, the implantable medical device 100, 700 may be retrieved by pulling on its distal end portion through the second intraluminal access; in this case, the first intraluminal access is not required to be obtained, according to embodiments.

At 2810, optionally, the method may further include closing at least one of the first intraluminal access and the second intraluminal access when such access(se) is a percutaneous body conduit access obtained by medical procedure, according to embodiments. Typically, the first intraluminal access and the second intraluminal access are close after implantation.

The pump element(s) described and illustrated herein may be provided as endovascular/intravascular pump(s) that are percutaneously and/or transcatheterly implantable and percutaneously and/or transcatheterly explantable in a lumen of body conduit(s), such as blood vessel(s). The pump element(s) may be axial-flow pump(s), centrifugal pump(s), and/or positive-displacement pump(s). The pump element(s) may lack a shroud encasing a pump impeller, as illustrated herein. In this case, the pump element(s) may be positioned within an anchor of the implantable medical device(s) to protect in use a lumen wall from impeller-induced damages or injuries. Alternatively, the pump element(s) may be provided with a shroud.

In use, the pump element(s) may be operated to move any biological fluid, such as blood, in a direction producing a proximal fluid outflow relative to the implantable medical device(s) that or in an opposite direction producing a distal fluid outflow relative to the implantable medical device(s). In use, the pump elements may be operated continuously, intermittently or cyclically to mimic heart pulsatility. In use, the pump elements are capable of producing a hemodynamic effect in a lumen of blood vessel(s).

The functional units described and illustrated herein may or may not be required to be powered in use to achieve their intended purpose.

The functional units are not limited to pump unit(s) and may in fact include sensor unit(s), such as physiological sensor(s) for reporting at least one physiological readout, such as fluid pressure, fluid flow rate, fluid viscosity, fluid-dissolved molecules (e.g., $O_2$ level and/or $CO_2$ level(s)), fluid temperature, fluid pH, fluid metabolite concentration, etc.

The functional unit(s) may include occluder unit(s) for selectively occluding in use a blood vessel so that blood flow is redirected toward another blood vessel for selectively enhancing organ perfusion.

The functional unit(s) may include substance delivery unit(s) for intraluminally delivering at least one substance. In this case, the elongated operable element(s) may be provided with a tube configured to convey the substance to the substance delivery unit(s). The substance(s) delivered may be, for example, a medicament or another fluid (e.g., blood, blood plasma, saline, glucose solution, etc.).

The functional unit(s) may include fluid sampling unit(s) for intraluminally sampling a fluid or analyte.

When assemblable and/or unassemblable, each one of multiple functional units may be a same functional unit, such as the pump units described and illustrated herein. Alternatively, each one of multiple functional units may be a components of an implantable medical device. The components being intraluminally assemblable to intraluminally build a functional implantable medical device.

The functions associated with the functional units are not limited to a single same function. In fact, each one of multiple functional units may have a various function associated therewith. Therefore, when an implantable medical device is provided with multiple functional units, multiple corresponding functions may be associated with the implantable medical device. Such multiple functions may be any combination of the functions described hereinbefore for the sensor unit(s), occluder unit(s), substance delivery unit(s), and/or fluid sampling unit(s). The combination of such functions may have a synergistic effect.

The optional controller described and illustrated herein may be a computer, a power source (e.g., an electrical and/or a motorized source), and the like and combination thereof that is configured to operate the functional unit(s) and pump element(s). Although illustrated herein as being a connectable component that is physically separated from the implantable medical devices, the controller may be at least partially integrated to the implantable medical device so as to form an integral, one-piece device.

Each one of the first and second intraluminal accesses described and illustrated herein may be an intraluminal percutaneous arterial and/or venous access. Each one of the first and second intraluminal accesses may be located on a same blood vessel, or on separate or different blood vessels. Each one of the first and second intraluminal accesses may be located on an upper subject's body portion, a lower subject's body portion, a left subject's body portion, and/or a right subject's body portion. Each one of the first and second intraluminal accesses may be a femoral access and/or an axillary/subclavian access. Each one of the first and second intraluminal accesses may be a surgically made access and/or a naturally occurring access. The first and second intraluminal accesses may be made or obtained such that the diameter of one of the first and second intraluminal accesses is smaller than the diameter of the other one of the first and second intraluminal accesses. The body conduit may be naturally occurring or surgically made, such as by tunnelisation.

The invention claimed is:

1. An implantable medical device, comprising:
a functional unit;
an elongated operable element connectable to and extendable from the functional unit; and
an introducer unit having a proximal end portion, a distal end portion, and a longitudinal guide hole that extends at least partially between the proximal end portion and the distal end portion, the longitudinal guide hole being configured to slidably receive the elongated operable element therein for assembling in vivo the functional unit to the proximal end portion of the introducer unit by manipulation of the elongated operable element from the distal end portion when the elongated operable element is connected to the functional unit, the distal end portion being configured to atraumatically introduce the introducer unit in a lumen of a subject's body conduit for implanting the functional unit in the lumen of the subject's body conduit.

2. The implantable medical device according to claim 1, wherein the distal end portion of the introducer unit has a tapered shape.

3. The implantable medical device according to claim 2, wherein the distal end portion of the introducer unit is a tip configured to removably attach the remainder of the introducer unit.

4. The implantable medical device according to claim 3, wherein the introducer unit defines a distal cavity through which the elongated operable element is slidable.

5. The implantable medical device according to claim 4, wherein a distal end portion of the elongated operable element is enclosable inside the distal cavity when the elongated operable element is slidably received in the longitudinal guide hole, and when the tip is removably attached to the remainder of the introducer unit.

6. The implantable medical device according to claim 5, wherein the elongated operable element comprises: an electrical connector at the distal end portion thereof.

7. The implantable medical device according to claim 1, wherein the elongated operable element is configured to removably attach a prolongation wire, the elongated operable element and the prolongation wire being slidable in the longitudinal guide hole when removably attached together.

8. The implantable medical device according to claim 1, further comprising: a guidewire attached to the distal end portion of the introducer unit, the guidewire being configured to be routed in the lumen of the subject's body conduit and to be manipulated for moving the introducer unit in the lumen of the subject's body conduit.

9. The implantable medical device according to claim 1, further comprising: a capture element disposed to the proximal end portion of the functional unit, the capture element being configured to be captured by a tool in the lumen of the subject's body conduit for moving the functional unit in the lumen of the subject's body conduit.

10. The implantable medical device according to claim 1, wherein the elongated operable element is configured to electrically operate the functional unit therethrough.

11. The implantable medical device according to claim 10, wherein the elongated operable element is an electrical cable, and the functional unit is a pump unit that is electrically operable through the electrical cable by a controller.

12. A method of implanting an implantable medical device in a lumen of a subject's body conduit, the method comprising:
introducing the implantable medical device in the lumen of the subject's body conduit through a first percutaneous intraluminal access;
advancing the implantable medical device in the lumen of the subject's body conduit up to a second percutaneous intraluminal access;
externalizing an end portion of the implantable medical device through the second percutaneous intraluminal access; and
operating the implantable medical device in the lumen of the subject's body conduit from the end portion of the implantable medical device.

13. The method according to claim 12, further comprising: routing a guidewire between the first percutaneous intraluminal access and the second percutaneous intraluminal access, and pulling the guidewire through the second percutaneous intraluminal access to cause, when the guidewire is attached to the implantable medical device, at least one of the following: (i) introduction of the implantable medical device in the lumen of the subject's body conduit through the first percutaneous intraluminal access, (ii) advancement of the implantable medical device in the lumen of the subject's body conduit up to the second percutaneous intraluminal access, and (iii) externalization of the end portion of the implantable medical device through the second percutaneous intraluminal access.

14. The method according to claim 12, further comprising: manipulating the implantable medical device from the end portion thereof that is externalized through the second percutaneous intraluminal access to assemble the implantable medical device in the lumen of the subject's body conduit.

15. The method according to claim 14, wherein the implantable medical device is slidably assembled.

16. The method according to claim 15, wherein said manipulating the implantable medical device comprises: pulling an elongated operable element from the end portion of the implantable medical device to slidably assemble the implantable medical device.

17. The method according to claim 16, wherein said manipulating the implantable medical device comprises: pulling from the end portion of the implantable medical device a prolongation wire that is removably attached to the elongated operable element.

18. The method according to claim 17, further comprising: detaching the prolongation wire from the elongated operable element before said operating the implantable medical device.

19. The method according to claim 16, wherein said manipulating the implantable medical device comprises: removing a tip from the end portion of the implantable medical device for pulling the elongated operable element.

20. The method according to claim 16, wherein said operating comprises: electrically operating the implantable medical device through the elongated operable element.

21. The method according to claim 12, wherein said operating comprises: electrically operating the implantable medical device from the end portion thereof.

22. The method according to claim 21, wherein the implantable medical device comprises a transcatheterly implantable blood pump.

23. The method according to claim 12, further comprising: closing the first percutaneous intraluminal access.

* * * * *